(12) United States Patent
Sahoo et al.

(10) Patent No.: US 8,017,605 B2
(45) Date of Patent: Sep. 13, 2011

(54) P38 KINASE INHIBITING AGENTS

(75) Inventors: Soumya P. Sahoo, Old Bridge, NJ (US); Meng-Hsin Chen, Westfield, NJ (US); Kevin D. Dykstra, West Milford, NJ (US); Hiroo Koyama, Hoboken, NJ (US); Peter T. Meinke, Scotch Plains, NJ (US); Stephen J. O'Keefe, Mountainside, NJ (US); Ginger Xu-qiang Yang, Jersey City, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 160 days.

(21) Appl. No.: 12/481,614

(22) Filed: Jun. 10, 2009

(65) Prior Publication Data

US 2009/0325953 A1   Dec. 31, 2009

Related U.S. Application Data

(60) Provisional application No. 61/131,928, filed on Jun. 13, 2008.

(51) Int. Cl.
*A61K 31/437* (2006.01)
*A61K 31/519* (2006.01)
*A61K 31/5025* (2006.01)
*A61K 31/5377* (2006.01)
*C07D 471/04* (2006.01)
*A61P 11/06* (2006.01)
*A61P 19/00* (2006.01)

(52) U.S. Cl. ............ 514/234.2; 514/300; 514/303; 514/259.1; 514/248; 546/113; 546/121; 546/118; 544/281; 544/236; 544/127

(58) Field of Classification Search ............... 514/234.2, 514/300, 259.1, 303, 248; 546/113, 121, 546/118; 544/281, 236, 127
See application file for complete search history.

(56) References Cited

FOREIGN PATENT DOCUMENTS

| WO | 2004/031188 A | | 4/2004 |
|---|---|---|---|
| WO | 2005/028475 A | | 3/2005 |
| WO | 2007071965 | * | 6/2007 |
| WO | 2008/070507 A | | 6/2008 |

* cited by examiner

*Primary Examiner* — D Seaman
*Assistant Examiner* — Niloofar Rahmani
(74) *Attorney, Agent, or Firm* — Maria V. Marucci; Valerie J. Camara

(57) ABSTRACT

Compounds described by the chemical formula (I) or pharmaceutically acceptable salts thereof:

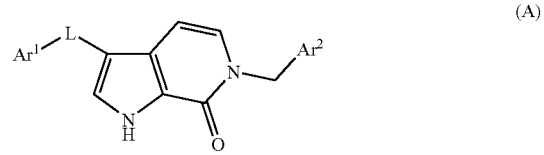

(A)

are inhibitors of p38 and are useful in the treatment of inflammation such as in the treatment of asthma, COPD, ARDS, rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

19 Claims, No Drawings

P38 KINASE INHIBITING AGENTS

CROSS REFERENCE TO RELATED APPLICATIONS

This application claims priority from U.S. Provisional Application Ser. No. 61/131,928 filed Jun. 13, 2008.

BACKGROUND OF THE INVENTION

The present invention relates to heterobicyclic compounds that inhibit the action of the p38 mitogen-activated protein kinase, a mammalian protein kinase that is involved in cell proliferation, cell response to stimuli, and cell death. In particular, this invention relates to heterobicyclic compounds that are selective and potent inhibitors of the p38 mitogen-activated protein kinase. This invention also relates to pharmaceutical compositions containing such heterobicyclic compounds that inhibit the p38 mitogen-activated protein kinase.

RELATED BACKGROUND

The Mitogen-Activated Protein (MAP) kinases are a family of proline-directed serine/threonine kinases that are activated by dual phosphorylation, and in turn phosphorylate their substrates on either Threonine-Proline or Serine-Proline sites.

MAP kinases are activated in response to a variety of signals including nutritional and osmotic stress, W light, growth factors, endotoxin and inflammatory cytokines. The p38 sub-group of MAP kinases (p38, also known as CSBP and RK) is a MAP kinase family of various isoforms, which is responsible for phosphorylating a large number of substrates, including transcription factors (e.g. ATF2, CHOP and MEF2C), other kinases (e.g. MAPKAP-2 and MAPKAP-3), tumor suppressors (e.g. p53) and translational regulators (e.g. 3EBP, PRAK).

A large number of chronic and acute conditions have been recognized to be associated with perturbation of the inflammatory response. A large number of cytokines participate in this response, including IL-1, IL-6, IL-8 and TNF. It appears that the expression, secretion and activity of these cytokines in the regulation of inflammation rely at least in part on the activation of p38. This kinase is activated by dual phosphorylation after stimulation by physiochemical stress, treatment with lipopolysaccharides or with pro-inflammatory cytokines such as IL-1, and TNF.

TNF and interleukins such as IL-1 and IL-8 affect a wide variety of cells and tissues and are important inflammatory mediators of a wide variety of disease states and conditions. TNF-α is a cytokine produced primarily by activated monocytes and macrophages. Excessive or unregulated TNF production has been implicated in mediating a number of diseases. Recent studies indicate that TNF has a causative role in the pathogenesis of rheumatoid arthritis. Additional studies demonstrate that inhibition of TNF has broad application in the treatment of inflammation, inflammatory bowel disease, multiple sclerosis and asthma. TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV-6), human herpesvirus-7 (HHV-7), human herpesvirus-8 (HHV-8), pseudorabies and rhinotracheitia, among others. I IL-8 is another pro-inflammatory cytokine, which is produced by mononuclear cells, fibroblasts, endothelial cells, and keratinocytes, and is associated with pathological conditions including inflammation.

IL-1 is produced by activated monocytes and macrophages and is involved in the inflammatory response. IL-1 plays a role in many pathophysiological responses including rheumatoid arthritis, fever and reduction of bone resorption.

TNF, IL-1 and IL-8 affect a wide variety of cells and tissues and are important inflammatory mediators of a wide variety of disease states and conditions. The inhibition of these cytokines by inhibition of the p38 kinase is of benefit in controlling, reducing and alleviating many of these disease states.

Within the past several years, p38 has been shown to comprise a group of MAP I kinases designated p38δ, p38γ, p38β, p38α Jiang, Y., et al., (A Biol Chem I (1996) 271:17920-17926) reported characterization of p38-β as a 372-amino acid protein closely related to p38-α. In comparing the activity of p38-α with that of p38-β, the authors state that while both are activated by proinflammatory cytokines and environmental stress, p38-β was preferentially activated by MAP kinase kinase-6 (MKK6) and preferentially activated transcription factor 2, thus suggesting that separate mechanisms for action may be associated with these forms. Kumar, S., et al., (Biochem Biophys Res Comm (1997) 235:533-538) and Stein, B., et al., (J Biol Chem (1997) 272: 19509-19517) reported a second isoform of p38-β-p38-β2, containing 364 amino acids with 73% identity to p38-α. All of these reports show evidence that p38-β is activated by proinflammatory cytokines and environmental stress, although the second reported p38-β isoform-p38-β2, appears to be preferentially expressed in the CNS, heart and skeletal muscle compared to the more ubiquitous tissue expression of p38-α. Furthermore, activated transcription factor-2 (ATF-2) was observed to be a better substrate for p38-β2 than for p38-α thus suggesting that separate mechanisms of action may be associated with these forms. The physiological role of p38-β1 has been called into question by the latter two reports since it cannot be found in human tissue and does not exhibit appreciable kinase activity with the substrates of p38-α.

The identification of p38-γ was reported by Li, Z., et al., (Biochem Biophys Res Comm (1996)228:334-340) and of p38-δ by Wang, X., et al., (J Biol Chem (1997) 272:23668-23674) and by Kumar, S., et al., (Biochem Biophys Res Comm (1997) 235:533-538). The data suggest that these two p38 isoforms (γ and δ) represent a unique subset of the MAPK family based on their tissue expression patterns, substrate utilization, response to direct and indirect stimuli, and susceptibility to kinase inhibitors. Various results with regard to differential response to drugs targeting the p38 family as between p38-α and either the putative p38-β1 or p38-β2, or both were reported by Jiang, Kumar, and Stein cited above as well as by Eyers, P. A., et al., (Chem and Biol (1995)5:321-328). An additional paper by Wang, Y., et al., (J Biol Chem (1998)273:2161-2168) suggests the significance of such differential effects. As pointed out by Wang et al., a number of stimuli, such as myocardial infarction, hypertension, valvular diseases, viral myocarditis, and dilated cardiomyopathy lead to an increase in cardiac workload and elevated mechanical stress on cardiomyocytes.

These are said to lead to an adaptive hypertrophic response, which, if not controlled, has decidedly negative consequences. Wang et al. cite previous studies which have shown that in ischemia reperfusion treated hearts, p38 MAPK activities are elevated in association with hypertrophy and programmed cell death. Wang et al. show in the cited paper that activation of p38-β activity results in hypertrophy, whereas activation of p38-α activity leads to myocyte apoptosis.

Thus, selective inhibition of p38-α activity as compared to p38-β activity will be of benefit in treating conditions associated with cardiac failure. These conditions I include congestive heart failure, cardiomyopathy, myocarditis, vasculitis, vascular restenosis, valvular disease, conditions associated with cardiopulmonary bypass, coronary artery bypass, grafts and vascular grafts. Further, to the extent that the α-isoform is toxic in other muscle cell types, α-selective inhibitors would be useful for conditions associated with cachexia attributed to TNF or other conditions such as cancer, infection, or autoimmune disease.

PCT applications W 098/06715, W 098/07425, W 098/28292 and WO 96/40143, describe the relationship of p38 kinase inhibitors with various disease states. As mentioned in these applications, inhibitors of p38 kinase are useful in treating a variety of diseases associated with chronic inflammation. These applications list rheumatoid arthritis, rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and isehemia, psoriasis, restenosis, cerebral I malaria, chronic pulmonary inflammatory disease, silicosis, pulmonary sarcosis, bone resorption diseases such as osteoporosis, graft-versus-host reaction, Crohn's Disease, ulcerative colitis including inflammatory bowel disease (IBD) and pyresis.

SUMMARY OF THE INVENTION

Compounds described by the chemical formula (A) or pharmaceutically acceptable salts thereof:

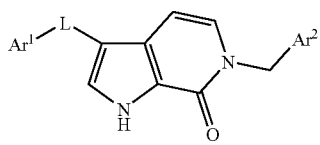

(A)

are inhibitors of p38 and are useful in the treatment of inflammation such as in the treatment of asthma, COPD, ARDS, rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

DETAILED DESCRIPTION OF THE INVENTION

In one embodiment, the present invention provides p38 inhibitor compounds of the chemical formula (A):

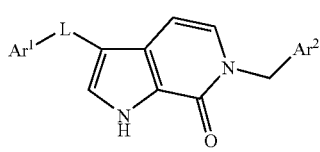

(A)

or a pharmaceutically acceptable salt thereof, wherein:
L is selected from the group consisting of:
 (a) —C(O)—,
 (b) —CH(OH)—,
 (c) —CH(NR$^3$R$^4$)—,
 (d) —C(=NOR$^3$)—,
 (e) —CH$_2$—, and
 (f) —S(O)$_n$—, wherein n is 0, 1 or 2;

Ar$^1$ is an optionally mono, di- or tri-substituted aromatic or heteroaromatic ring of 6 atoms, wherein the heteroaromatic ring may contain 1, 2 or 3 heteroatoms selected from N, S and O, wherein the substituents are independently selected from the group consisting of:
 (a) halo,
 (b) —C$_{1-4}$alkyl,
 (c) —O—C$_{1-4}$alkyl,
 (d) —CF$_3$,
 (e) —NH$_2$,
 (f) —NH—CH$_3$,
 (g) —CN,
 (h) —C(O)NH$_2$, and
 (i) —S(O)$_n$—CH$_3$;

Ar$^2$ is an optionally mono, di- or tri-substituted fused 5,6 bi-cyclic heterocyclic ring selected from the group consisting of;

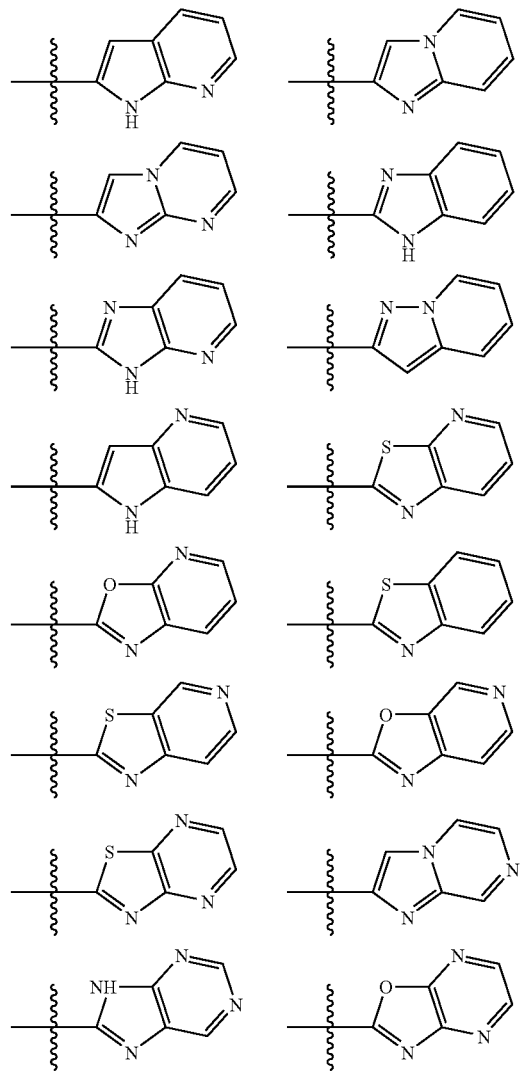

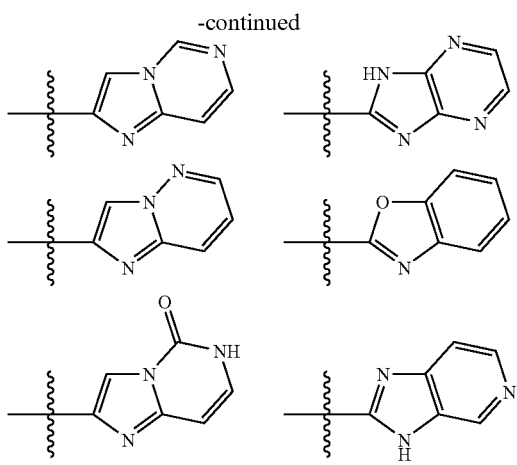

or N-oxide thereof wherein the substituents are independently selected from the group consisting of
(a) halo,
(b) —$C_{1-4}$alkyl,
(c) —O—$C_{1-4}$alkyl,
(d) —$CF_3$,
(e) —$NH_2$, and
(f) —$NH_2$—$CH_3$,
(g) —$NH_2$—$CH_2CF_3$,
(h) —C(O)-morpholinyl,
(i) —C(O)—$NR^1R^2$,
(j) —C(O)OH,
(k) —CN,
(l) a 5 or 6 membered heteroaromatic or heterocyclic ring containing 1, 2 or 3 hetero atoms selected from the group consisting of S, O and N;

$R^1$, $R^2$, $R^3$ and $R^4$ are independently selected from the group consisting of
(a) hydrogen, and
(b) $C_{1-4}$alkyl,
or $R^1$ and $R^2$ or $R^3$ and $R^4$ may be joined together to from a 5 or 6 membered saturated ring, said ring optionally containing a heteroatom selected from S, N and O.

Within this embodiment there is a genus wherein L is selected from the group consisting of
(a) —C(O)—, and
(b) —$CH_2$—;

Within this genus there is a sub-genus wherein L is —C(O)—.

Within this embodiment there is a genus wherein $Ar^1$ is an optionally mono, di- or tri-substituted aromatic or heteroaromatic ring of 6 atoms, wherein the heteroaromatic ring may contain 1, 2 or 3 heteroatoms selected from N, S and O, wherein the substituents are independently selected from the group consisting of:
(a) halo,
(b) —$C_{1-4}$alkyl, and
(c) —O—$C_{1-4}$alkyl, Within this genus there is a sub-genus wherein $Ar^1$ is an optionally mono, di- or tri-substituted phenyl or pyridyl, wherein the substituents are independently selected from the group consisting of:
(a) fluoro,
(b) chloro, and
(c) —$CH_3$.

Within this embodiment there is a genus wherein in choice (l) of $Ar^2$, the 5 or 6 membered heteroaromatic or heterocyclic ring containing 1, 2 or 3 hetero atoms selected from the group consisting of S, O and N is selected from the group consisting of:
(a) pyridinyl,
(b) pyridazinyl,
(c) pyrimidinyl,
(d) pyrazinyl,
(e) thiazolyl,
(f) thiophenyl,
(g) pyrrolyl,
(h) oxazolyl,
(i) pyrrolidinyl,
(j) piperidinyl,
(k) piperazinyl, and
(l) morpholinyl.

Within this embodiment there is a genus wherein $Ar^2$ is an optionally mono, di- or tri-substituted fused 5,6 bi-cyclic heterocyclic ring selected from the group consisting of:

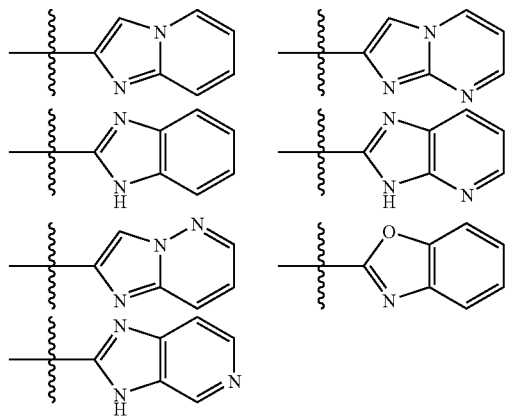

or N-oxide thereof, wherein the substituents are independently selected from the group consisting of
(a) halo,
(b) —$C_{1-4}$alkyl,
(c) —O—$C_{1-4}$alkyl,
(d) —$CF_3$,
(e) —C(O)-morpholinyl,
(f) —C(O)—$NR^1R^2$, and
(g) —C(O)OH.

Within this genus there is a sub-genus wherein $Ar^2$ is an optionally mono, di- or tri-substituted fused 5,6 bi-cyclic heterocyclic ring selected from the group consisting of:

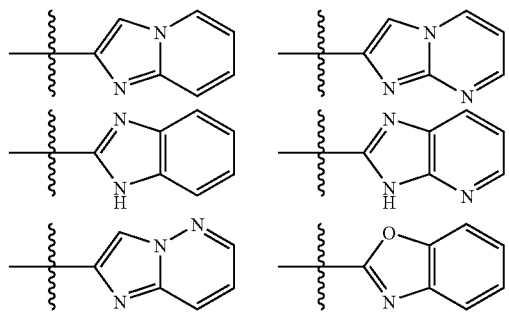

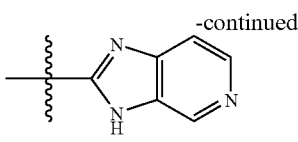

or N-oxide thereof wherein the substituents are independently selected from the group consisting of
(a) halo,
(b) —CH$_3$,
(c) —O—CH$_3$, and
(d) —CF$_3$.

Within this embodiment there is a genus wherein R$^1$, R$^2$, R$^3$ and R$^4$ are independently selected from the group consisting of
(a) hydrogen, and
(b) methyl, or R$^1$ and R$^2$ or R$^3$ and R$^4$ may be joined together to from a 5 or 6 membered saturated ring, said ring optionally containing a heteroatom selected from S, N and O.

Within the embodiment there is a genus of compounds of Formula (I)

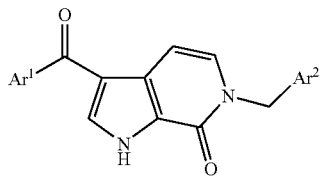

(I)

or a pharmaceutically acceptable salt thereof, wherein:

Ar$^1$ is an optionally mono, di- or tri-substituted aromatic or heteroaromatic ring of 6 atoms, wherein the heteroaromatic ring may contain 1, 2 or 3 heteroatoms selected from N, S and O, wherein the substituents are independently selected from the group consisting of
(a) halo,
(b) —C$_{1-4}$alkyl, and
(c) —O—C$_{1-4}$alkyl, Ar$^2$ is an optionally mono, di- or tri-substituted fused 5,6 bi-cyclic heterocyclic ring selected from the group consisting of

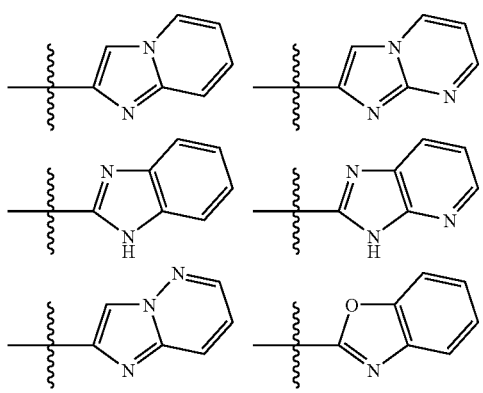

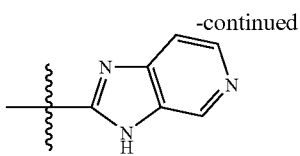

or N-oxide thereof, wherein the substituents are independently selected from the group consisting of
(a) halo,
(b) —C$_{1-4}$alkyl,
(c) —O—C$_{1-4}$alkyl,
(d) —CF$_3$,
(e) —C(O)-morpholinyl,
(f) —C(O)—NR$^1$R$^2$, and
(g) —C(O)OH; and R$^1$ and R$^2$ are independently selected from the group consisting of
(a) hydrogen, and
(b) C$_{1-4}$alkyl, or R$^1$ and R$^2$ may be joined together to from a 5 or 6 membered saturated ring, said ring optionally containing a heteroatom selected from S, N and O.

Within this genus there is a sub-genus wherein
Ar$^1$ is an optionally mono, di- or tri-substituted phenyl or pyridyl, wherein the substituents are independently selected from the group consisting of:
(a) fluoro
(b) chloro, and
(c) —CH$_3$;

Ar$^2$ is an optionally mono, di- or tri-substituted fused 5,6 bi-cyclic heterocyclic ring selected from the group consisting of

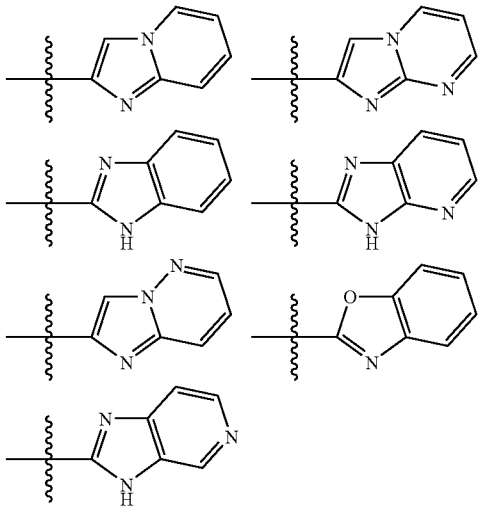

or N-oxide thereof, wherein the substituents are independently selected from the group consisting of
(a) halo,
(b) —CH$_3$,
(c) —O—CH$_3$,
(d) —C(O)—NR$^1$R$^2$, and
(e) —CF$_3$, and R$^1$ and R$^2$ are independently selected from the group consisting of
(a) hydrogen, and
(b) methyl, or $R^1$ and $R^2$ may be joined together to from a 5 or 6 membered saturated ring, said ring optionally containing a heteroatom selected from S, N and O.

As discussed above, the p38 sub-group of MAP kinases is a MAP kinase family of various isoforms (including p38δ, p38γ, p38β, p38α), which is responsible for phosphorylating a large number of downstream substrates. Data suggests that two p38 isoforms (α and β) represent a unique subset of the MAPK family based on their tissue expression patterns, substrate utilization, response to direct and indirect stimuli, and susceptibility to kinase inhibitors. Various results with regard to differential response to drugs targeting the p38 family as between p38-α and either the putative p38-β1 or p38-β2, or both were reported by Jiang, Kumar, and Stein supra, as well as by Eyers, P. A., et al., [Chem and Biol (1995)5:321-328]. An additional paper by Wang, Y., et al., [J Biol Chem (1998) 273:2161-2168] suggests the significance of such differential effects of selectively inhibiting p38-α. Canonical inhibitors of p38-α inhibit phosphorylation of downstream substrates, including, but not limited to, MK2, MK3, ATF2, Mnk2a, MSK1, TAB1, CREB and HSP27. Based on these data, p38-α inhibitors that preferentially inhibit phosphorylation of one subset of these downstream substrates should exhibit an increased therapeutic index relative to canonical p38 inhibitors.

Accordingly, in one aspect, the invention is directed to compounds of Formula I which selectively inhibit p38-α in preference to p38-β and/or p38δ and/or p38γ. Within this aspect are compounds of Formula I, which inhibit p38-α in preference to p38-β and/or p38δ and/or p38γ, as measured by an in vitro kinase assay.

In a still further aspect, the invention is directed to compounds of Formula I which are potent inhibits p38-α and selectively inhibit phosphorylation of one or more of MK2, MK3, ATF2, Mnk2a, MSK1 and TAB1, in preference to the rest of these or other downstream substrates. For example, in one aspect, the invention is direct to compounds of Formula I which selectively inhibit phosphorylation of MK2 and MK3 in preference to MSK1, ATF2 or a peptide substrate. Within this aspect are compounds of Formula I, which are potent inhibitors of p38-α and selectively inhibit phosphorylation of MM2 in preference to a peptide substrate as measured by an in vitro kinase assay.

The term "acetal" means a functional group or molecule containing a CH bonded to two —OR groups. A "cyclic acetal" thus means a cyclic or ring structure containing an acetal group.

The term "alkyl" means carbon chains that have no double or triple bonds, and that may be linear or branched or combinations thereof. Thus, $C_1$-$C_6$ alkyl is defined to identify the group as having 1, 2, 3, 4, 5 or 6 carbons in an arrangement that is linear, branched, or a combination thereof Examples of alkyl groups include methyl, ethyl, propyl, n-propyl, isopropyl, butyl, sec- and tert-butyl, pentyl, hexyl, heptyl and the like. The term "$C_0$-$C_4$alkyl" includes alkyls containing 4, 3, 2, 1, or no carbon atoms. An alkyl with no carbon atoms is a hydrogen atom substituent when the alkyl is a terminus moiety. An alkyl with no carbon atoms is a direct bond when the alkyl is a bridging moiety.

The term "alkene" means linear or branched structures and combinations thereof, of the indicated number of carbon atoms, having at least one carbon-to-carbon double bond, wherein hydrogen may be replaced by an additional carbon-to-carbon double bond. $C_2$-$C_6$ alkene, for example, includes ethylene, propylene, 1-methylethylene, butylene and the like.

The term "alkynyl" means linear or branched structures and combinations thereof, of the indicated number of carbon atoms, having at least one carbon-to-carbon triple bond. Thus $C_2$-$C_6$ alkynyl is defined to identify the group as having 2, 3, 4, 5 or 6 carbon in a linear or branched arrangement, such that $C_2$-$C_6$ alkynyl specifically includes 2-hexynyl and 2-pentynyl.

The term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

The term "amine" unless specifically stated otherwise includes primary, secondary and tertiary amines.

The term "aryl," unless specifically stated otherwise, is intended to mean any stable monocyclic or fused bicyclic carbon ring of up to 7 members in each ring, wherein at least one ring is aromatic. Examples of such aryl elements include phenyl, naphthyl and tolyl.

The term "aryloxy" unless specifically stated otherwise includes multiple ring systems as well as single ring systems such as, for example, phenyl or naphthyl, connected through the oxy connecting atom to the connecting site.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalenyl, adamantanyl, indanyl, indenyl, fluorenyl, 1,2,3,4-tetrahydronaphthalenyl and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "cycloalkyloxy" unless specifically stated otherwise includes a cycloalkyl group connected to the oxy connecting atom.

The term "hetero," unless specifically stated otherwise, includes one or more O, S, or N atoms. For example, heterocycloalkyl and heteroaryl include ring systems that contain one or more O, S, or N atoms in the ring, including mixtures of such atoms. The hetero atoms replace ring carbon atoms.

Examples of heterocycloalkyl include azetidinyl, pyrrolidinyl, piperidinyl, piperazinyl, morpholinyl, tetrahydrofuranyl, imidazolinyl, cyclic acetals, cyclic ketals, pyrolidin-2-one, piperidin-2-one and thiomorpholinyl. As used herein, "heterocycloalkyl" includes bridged heterocycloalkyls having two or more heterocycloalkyl groups joined via adjacent or non-adjacent atoms.

The term "heteroaryl", as used herein except where noted, is intended to mean a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, pyridine, pyrimidine, pyrazine, thiophene, oxazole, thiazole, triazole, thiadiazole, oxadiazole, pyrrole, 1,2,4-oxadiazole, 1,3,4-oxadiazole, 1,2,4-thiadiazole, 1,3,4-thiadiazole, and 1,2,4-triazole.

Additional examples of heteroaryl include quinolinyl, pyrimidinyl, isoquinolinyl, pyridazinyl, quinoxalinyl, furyl, benzofuryl, dibenzofuryl, thienyl, benzothienyl, indolyl, indazolyl, isoxazolyl, isothiazolyl, imidazolyl, benzimidazolyl, thiadiazolyl, tetrazolyl.

The term "heteroaryloxy" unless specifically stated otherwise describes a heteroaryl group connected through an oxy connecting atom to the connecting site.

Examples of heteroaryl($C_{1-6}$)alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

Unless otherwise stated, the term "carbamoyl" is used to include —NHC(O)OC1-C4alkyl, and —OC(O)NHC1-C4alkyl.

The term "halogen" includes fluorine, chlorine, bromine and iodine atoms.

The term "ketal" means a functional group or molecule containing a carbon bonded to two —OR groups. A "cyclic ketal" thus means a cyclic or ring structure containing a ketal group.

The term "optionally substituted" is intended to include both substituted and unsubstituted. Thus, for example, optionally substituted aryl could represent a pentafluorophenyl or a phenyl ring. Further, the substitution can be made at any of the groups. For example, substituted aryl($C_{1-6}$)alkyl includes substitution on the aryl group as well as substitution on the alkyl group.

The term "oxide" of heteroaryl groups is used in the ordinary well-known chemical sense and include, for example, N-oxides of nitrogen heteroatoms.

Compounds described herein contain one or more double bonds and may thus give rise to cis/trans isomers as well as other conformational isomers. The present invention includes all such possible isomers as well as mixtures of such isomers.

Unless specifically stated otherwise or indicated by a bond symbol (dash or double dash), the connecting point to a recited group will be on the right-most stated group. That is, for example, a phenylalkyl group is connected to the main structure through the alkyl and the phenyl is a substituent on the alkyl.

The compounds of the present invention are useful in various pharmaceutically acceptable salt forms. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be mixtures of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, famaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

The compounds of the present invention may have asymmetric centers and occur as racemates, racemic mixtures, and as individual diastereomers. All such isomers, including optical isomers, being included in the present invention.

The invention described herein also includes a pharmaceutical composition which is comprised of a compound described by Formula (I), or a pharmaceutically acceptable salt thereof, in combination with a pharmaceutically acceptable carrier.

The invention described herein also includes a pharmaceutical composition which is comprised of a compound described by Formula (I), or a pharmaceutically acceptable salt thereof, in combination with a pharmaceutically acceptable carrier. The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) Leukotriene receptor antagonists, ii) Leukotriene biosynthesis inhibitors, iii) corticosteroids, iv) H1 receptor antagonists, v) beta 2 adrenoceptor agonists, vi) COX-2 selective inhibitors, vii) statins, viii) non-steroidal anti-inflammatory drugs ("NSAID"), and ix) M2/M3 antagonists.

The invention described herein also includes a method of treating arthritis which is comprised of administering to a mammalian patient in need of such treatment a compound described by Formula (I), or a pharmaceutically acceptable salt thereof, in an amount which is effective to treat arthritis. The invention described herein also includes a method of treating arthritis which is comprised of administering to a mammalian patient in need of such treatment a compound described by Formula (I), or a pharmaceutically acceptable salt thereof, in an amount which is effective to treat arthritis. The invention includes methods of treating arthritis by administering to a mammalian patient in need of such treatment a compound described by Formula (I), or a pharmaceutically acceptable salt thereof, in combination or in coadministration with a COX-2 inhibitor.

The invention described herein also includes a method of treating a cytokine mediated disease in a mammal, comprising administering to a mammalian patient in need of such treatment an amount of a compound described by Formula (I), or a pharmaceutically acceptable salt thereof, in an amount which is effective to treat said cytokine mediated disease.

Of particular interest is a method of treating inflammation in a mammalian patient in need of such treatment, which is comprised of administering to said patient an anti-inflammatory effective amount of a compound described by Formula (I), or a pharmaceutically acceptable salt thereof.

Another method which is of particular interest is a method of treating a cytokine mediated disease as described herein wherein the disease is osteoporosis.

Another method which is of particular interest is a method of treating a cytokine mediated disease as described herein wherein the disease is non-osteoporotic bone resorption.

Yet another method which is of particular interest is a method of treating a cytokine mediated disease as described herein wherein the disease is Crohn's disease.

This invention also relates to a method of treating arthritis in a mammal in need such treatment, which comprises administering to said mammal an amount of a compound of formula I which is effective for treating arthritis. Such method includes the treatment of rheumatoid and osteoarthritis.

When administered to a patient for the treatment of arthritis, the dosage used can be varied depending upon the type of arthritis, the age and general condition of the patient, the particular compound administered, the presence or level of toxicity or adverse effects experienced with the drug, and other factors. A representative example of a suitable dosage range is from as low as about 0.01 mg/kg to as high as about 100 mg/kg. However, the dosage administered is generally left to the discretion of the physician.

This invention also relates to a method of inhibiting the action of p38 in a mammal in need thereof, which comprises administering to said mammal an effective amount of a compound described by Formula (I), or a pharmaceutically acceptable salt thereof, to inhibit said action of p38, down to normal levels, or in some cases to subnormal levels, so as to ameliorate, prevent or treat the disease state.

The compounds of formula I can be used in the prophylactic or therapeutic treatment of disease states in mammals which are exacerbated or caused by excessive or unregulated cytokines, more specifically IL-1, IL-6, IL-8 or TNF.

Because the compounds of formula I inhibit cytokines, such as IL-1, IL-6, IL-8 and TNF, by inhibiting the action of p38 the compounds are useful for treating diseases in which cytokine presence or activity is implicated, such as pain, rheumatoid arthritis, rheumatoid spondylitis, osteoarthritis, gouty arthritis and other arthritic conditions.

The compounds described by Formula (I), or a pharmaceutically acceptable salt thereof, are also useful to treat other disease states mediated by excessive or unregulated TNF production or activity. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft v. host rejection, allograft rejection, fever, myalgia due to infection, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis, pyresis, AIDS and other viral infections, such as cytomegalovirus (CMV), influenza virus, and the herpes family of viruses such as Herpes Zoster or Simplex I and II.

The compounds described by Formula (I), or a pharmaceutically acceptable salt thereof, are also useful topically in the treatment of inflammation such as in the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

The compounds described by Formula (I), or a pharmaceutically acceptable salt thereof, are also useful in treating diseases such as chronic obstructive pulmonary disease and diseases characterized by excessive IL-8 activity. These disease states include psoriasis, inflammatory bowel disease, asthma, cardiac and renal reperfusion injury, adult respiratory distress syndrome, thrombosis and glomerulonephritis.

The invention thus includes a method of treating psoriasis, inflammatory bowel disease, asthma, cardiac and renal reperfusion injury, adult respiratory distress syndrome, thrombosis and glomerulonephritis, in a mammal in need of such treatment, which comprises administering to said mammal a compound described by Formula (I), or a pharmaceutically acceptable salt thereof, in an amount which is effective for treating said disease or condition.

The compounds described by Formula (I), or a pharmaceutically acceptable salt thereof, are also useful for treating Alzheimer's disease. The instant invention thus includes a method of treating Alzheimer's disease in a mammal in need of such treatment, which comprises administering to said mammal a compound of Formula (I), or a pharmaceutically acceptable salt thereof in an amount effective for treating said disease or condition.

When administered to a patient for the treatment of a disease in which a cytokine or cytokines are implicated, the dosage used can be varied depending upon the type of disease, the age and general condition of the patient, the particular compound administered, the presence or level of toxicity or adverse effects experienced with the drug, and other factors. A representative example of a suitable dosage range is from as low as about 0.01 mg/kg to as high as about 100 mg/kg. However, the dosage administered is generally left to the discretion of the physician.

The methods of treatment can be carried out by delivering the compound of formula I parenterally. The term 'parenteral' as used herein includes intravenous, intramuscular, or intraperitoneal administration. The subcutaneous and intramuscular forms of parenteral administration are generally advantageous The instant invention can also be carried out by delivering the compound of formula I subcutaneously, intranasally, intrarectally, transdermally or intravaginally.

The compounds of formula I may also be administered by inhalation. By 'inhalation' is meant intranasal and oral inhalation administration. Appropriate dosage forms for such administration, such as an aerosol formulation or a metered dose inhaler, may be prepared by convention techniques.

The invention also relates to a pharmaceutical composition comprising a compound of formula I and a pharmaceutically acceptable carrier. The compounds of formula I may also be included in pharmaceutical compositions in combination with a second therapeutically active compound.

The pharmaceutical carrier employed may be, for example, either a solid, liquid or gas. Examples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen.

Similarly, the carrier or diluent may include time delay material well known in the art, such as glyceryl monostearate or glyceryl distearate, alone or with a wax.

A wide variety of pharmaceutical dosage forms can be employed. If a solid dosage is used for oral administration, the preparation can be in the form of a tablet, hard gelatin capsule, troche or lozenge. The amount of solid carrier will vary widely, but generally will be from about 0.025 mg to about 1 g. When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution.

Topical dosage forms are also included. Examples of topical dosage forms are solids, liquids and semi-solids. Solids would include dusting powders, poultices and the like. Liquids include solutions, suspensions and emulsions. Semisolids include creams, ointments, gels and the like.

The amount of a compound of formula I used topically will, of course, vary with the compound chosen, the nature and severity of the condition, and can be varied in accordance with the discretion of the physician. A representative, topical, dose of a compound of formula I is from as low as about 0.01 mg to as high as about 2.0 g, administered one to four, or, advantageously, one to two times daily.

The active ingredient may comprise, for topical administration, from about 0.001% to about 10% w/w.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof Suspending agents such as natural gums, cellulose derivatives or inorganic materials such as silicas, and other ingredients such as lanolin may also be included.

For inhaled formulations, the dosage amount per administration is generally lower than that for an oral formulation such as a tablet or capsule. For example, a daily dose of the active compound administered via an inhaled formulation may range from 0.010 mg to 10 mg, and particularly from 0.010 mg to 2.5 mg. Single or multiple inhaled doses may be used per day, but a single inhaled dose is preferred.

For administration by inhalation, the salts of Compound I of the present invention are conveniently delivered in the form of an aerosol suitable for pulmonary drug delivery. These aerosol dosage forms include but are not limited to nebulized solutions and suspensions, metered-dose inhalers or dry powder inhalers. For nebulization the active ingredient(s) are typically formulated in an aqueous vehicle and administered by jet or electronic devices capable of generating a fine aerosol cloud. Metered-dose inhalers (MDI) use propellants such as hydrofluorocarbons to solubilize or suspend the active ingredient in a pressurized container capable of generating the disperse aerosol. For dry powder inhalation, the salts of Compound I are used alone or with excipients in conjunction with a delivery device capable for delivery of the active substance to the lung.

In one embodiment the medicinal preparation is adapted for use with a pressurized metered dose inhaler which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs) as the use of chlorofluorocarbons (known also as Freons or CFCs) is being phased out. In particular, 1,1,1,2-tetrafluoroethane (HFA 134a) and 1,1,1,2,3,3,3-heptafluoropropane (HEA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler. The inhalation composition suitable for use in DPIs typically comprises particles of the active ingredient and particles of a pharmaceutically acceptable carrier. The particle size of the active material may vary from about 0.1 μm to about 10 μm; however, for effective delivery to the distal lung, at least 95 percent of the active agents particles are 5 μm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Rotohaler, Diskhaler, and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder.

The present invention in one embodiment provides a composition for use in dry powder inhaler, which comprises montelukast acid and Compound X, and lactose for inhalation as a carrier, wherein said composition is adapted for simultaneous, sequential or separate administration of the active agents. The weight ratio of lactose to montelukast acid is from about 1:1 to about 30:1, and to Compound X is from about 20:1 to about 30:1. In one instance the weight ratio of lactose to montelukast acid is about 2:1 to about 25:1, and to Compound X is about 20:1 to about 25:1.

The present invention in one embodiment provides a composition for use in dry powder inhaler, which comprises montelukast acid and an inhaled corticosteroid, and lactose for inhalation as a carrier, wherein said composition is adapted for simultaneous, sequential or separate administration of the active agents. In such compositions the weight ratio of lactose to montelukast acid is generally from about 1:1 to about 30:1. In a composition where the inhaled corticosteroid is mometasone furoate, the weight ratio of lactose to mometasone furoate is from about 130:1 to about 4:1, and in one embodiment the ratio is from about 124:1 to about 60:1. In a composition where the inhaled corticosteroid is ciclesonide, the weight ratio of lactose to ciclesonide is about 350:1 to about 100:1.

The powder may also contain fine particles of an excipient material, which may for example be a material such as one of those mentioned above as being suitable for use as a carrier material, especially a crystalline sugar such as dextrose or lactose. The fine excipient material may be of the same or a different material from the carrier particles, where both are present. The particle size of the fine excipient material will generally not exceed 30 μm, and preferably does not exceed 20 μm. In some circumstances, for example, where any carrier particles and/or any fine excipient material present is of a material itself capable of inducing a sensation in the oropharyngeal region, the carrier particles and/or the fine excipient material can constitute the indicator material. For example, the carrier particles and/or any fine particle excipient may comprise mannitol.

The formulations described herein may also include one or more additives, in an amount from about 0.1% to about 10% by weight, and preferably from about 0.15% to 5%, most preferably from about 0.5% to about 2%. Additives may include, for example, magnesium stearate, leucine, lecithin, and sodium stearyl filmarate. When the additive is micronized leucine or lecithin, it is preferably provided in an amount from about 0.1% to about 10% by weight preferably about 0.5% to about 5%, preferably about 2%, of micronized leucine. Preferably, at least 95% by weight of the micronized leucine has a particle diameter of less than 150 microns, preferably less than 100 microns, and most preferably less than 50 microns. Preferably, the mass median diameter of the micronized leucine is less than 10 microns.

If magnesium stearate or sodium stearyl lumarate is used as the additive, it is preferably provided in an amount from about 0.05% to about 5%, preferably from about 0.15% to about 2%, most preferably from about 0.25 to about 0.5%.

Where reference is made to particle size of particles of the powder, it is to be understood, unless indicated to the contrary, that the particle size is the volume weighted particle size. The particle size may be calculated by a laser diffraction method. Where the particle also includes an indicator material on the surface of the particle, advantageously the particle size of the coated particles is also within the preferred size ranges indicated for the uncoated particles.

The dry powder pharmaceutical compositions in accordance with this invention may be prepared using standard methods. The pharmaceutically active agents, carrier particles, and other excipients, if any, may be intimately mixed using any suitable blending apparatus, such as a tumbling mixer. The particular components of the formulation can be admixed in any order. Pre-mixing of particular components may be found to be advantageous in certain circumstances. The powder mixture is then used to fill capsules, blisters, reservoirs, or other storage devices for use in conjunction with dry powder inhalers.

In a dry powder inhaler, the dose to be administered is stored in the form of a non-pressurized dry powder and, on actuation of the inhaler; the particles of the powder are inhaled by the patient. DPIs can be unit-dose devices in which the powder is contained in individual capsules, multiple-unit dose in which multiple capsules or blisters are used, and reservoir devices in which the powder is metered at dosing time from a storage container. Dry powder inhalers can be "passive" devices in which the patients breath is used to disperse the powder for delivery to the lungs, or "active" devices in which a mechanism other than breath actuation is used to disperse the powder. Examples of "passive" dry powder inhaler devices include the Spinhaler, Handihaler, Rotahaler, Diskhaler, Diskus, Turbuhaler, Clickhaler, etc. Examples of active inhalers include Nektar Pulmonary Inhaler (Nektar Therapeutics), Vectura Limited's Aspirair™ device, Microdose DPI (MicroDose), and Oriel DPI (Oriel). It should be appreciated, however, that the compositions of the present invention can be administered with either passive or active inhaler devices.

Assays

Protein Expression and Purification.

Murine p38 containing the FLAG epitope tag was expressed in *Drosophila* S2 cells under transcriptional control of a copper-inducible metallothionein promoter. Expression of recombinant p38 was induced by treating transfected cells with 1 mM CuSO4 for 4 hours. To generate active recombinant murine p38, CuSO4-treated S2 cells were stimulated 10 minutes prior to harvest with 400 mM NaCl, 2 mM Na3VO4, and 100 µg/L okadaic acid. Cell pellets were washed with phosphate-buffered saline, 2 mM Na3VO4, and lysed in 20 mM Tris HCl, pH 7.5, 120 mM NaCl, 1% Triton X-100, 2 mM EDTA, 20 mM NaF, 4 mM Na3VO4, 2 mM Prefabloc SC (Boehringer Mannheim). Cell lysates were centrifuged for 10 min at 13,000×g, and activated, recombinant murine p38 was immunoaffinity purified from the lysate by column chromatography through anti-FLAG M2 resin (Kodak) that had been equilibrated with lysis buffer. After loading the extract the resin was washed with 10 column volumes of lysis buffer, 10 column volumes buffer A (10 mM Tris HCl, pH 7.5, 500 mM NaCl, 20% glycerol) and 10 column volumes of buffer B (10 mM Tris HCl pH 7.5, 150 mM NaCl, 20% glycerol). The fusion protein was eluted in buffer B containing 100 µg/mL FLAG peptide (Kodak).

The N-terminal 115 amino acids of ATF-2 was expressed in *E. coli* as a fusion protein with glutathione-S-transferase. The fusion protein was purified over glutathione agarose according to standard procedures (Pharmacia).

p38 Kinase Assay.

p38 kinase assays were performed in a reaction volume of 100 µL in a 96-well plate, at 30° for 45-1200 min under the following conditions: 25 mM Hepes, pH 7.4, 10 mMmgCl2, 20 mM β-glycerolphosphate, 2 mM DTT, 5 µM ATP, 10 µCi [γ-33P]-ATP and ~2 µM GST-ATF2. Serial dilutions of compounds were added to each reaction in 2 µL DMSO. 2 µL of DMSO was added to the last row of each reaction plate as the no inhibitor control for each inhibitor titration. The reaction was terminated with an equal volume of a stop solution containing 100 mM EDTA and 15 mM sodium pyrophosphate. PVDF filter plates (MAIPNOB50, Millipore) were pre-wet with methanol and washed with the stop solution. 50 µL aliquots from a single reaction were applied to the filter under vacuum, and the filter was washed twice with 75 mM phosphoric acid. The filter plates were counted in a scintillation counter (Top Count, Packard) and the percent inhibition at each compound concentration is determined.

Alternatively, p38 kinase assays were performed in a reaction volume of 70 µL in a 384-well plate, at 30° for 45-1220 min under the following conditions: 50 mM Hepes, pH 7.4, 10 mM MgCl2, 1 mg/ml FA Free BSA, 1 mM DTT, 10 µM ATP, 10 µM p38 peptide [Caliper Life Sciences FL-Peptide 8 (5-FAM-IPTSPITTTYFFFKKK-COOH)] and 5.7 nM p38-α (Millipore), or 14.3 nM unactivated MAPKAP kinase-2, 0.18 nM p38-α (Millipore) and 2 uM RSK peptide [Caliper Life Sciences FL-Peptide 11 (5-FAM-KKLNRTLSVA-COOH)]. Serial dilutions of compounds were added to each reaction in 700 nL DMSO. 700 nL of DMSO was added to the control wells of the reaction plate as the no inhibitor control for each inhibitor titration. The reaction was terminated by the addition of 15 µL of a 100 mM EDTA. Product formation was analyzed using the Caliper LabChip 3000. The Separation buffer contained 100 mM HEPES pH 7.5, 0.015% Brij-35, 2.5% Coating Reagent #3 (Caliper Life Sciences) and 10 mM EDTA. Calculation of the substrate product ratios are performed using the HTS Well Analyzer software provided by Caliper Life Sciences and the percent inhibition at each compound concentration is determined.

TNF-α Release Assay.

Blood was obtained from healthy volunteers by venipuncture using sodium heparin as an anti-coagulant. Peripheral blood mononuclear cells (PBMCs) were isolated using Lymphocyte Separation Medium (ICN) according to manufacturers specifications. Isolated PBMCs were washed 3 times with HBSS and diluted to a density of 2×106 cells/mL in RPMI+ 5% autologous human serum. 50 µL of the serial dilutions of inhibitor were added to wells of a 96-well tissue culture plate followed by addition of 100 µL of PBMCs and then 50 µL of RPMI complete medium containing 400 ng/mL LPS. A control well of cells without compound but with LPS (maximal stimulation control) and one without compound and without LPS (background control) were included in each titration. The cells were incubated for 16 hours in a humidified incubator at 37° C., 5% $CO_2$. Supernatants were then harvested and TNF-α levels were quantified by immunoassay using commercial reagents (R&D, Inc).

The compounds of this invention demonstrated efficacy (IC50) in the above assays by results of less than 10 µM. Advantageous compounds had results less than 1 µM. Even more advantageous compounds had results less than 0.1 µM. Still more advantageous compounds had results in the assays of less than 0.01 µM. The follow are illustrative of the efficacy demonstrated by the specific Examples:

Structures of Compounds 1-29 and

In vitro Activities of Compounds 1-3, 5-25 and 27-29

| Compound | Example | Structure | IC$_{50}$ p38α *peptide [nM] | IC$_{50}$ hWB [nM] |
|---|---|---|---|---|
| 1 | 1 | 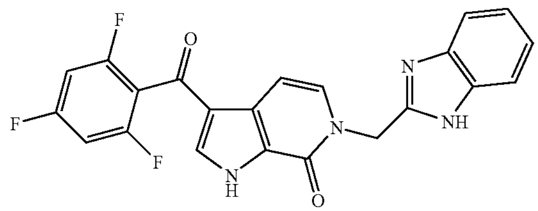 | 45 | 461 |
| 2 | 2 | 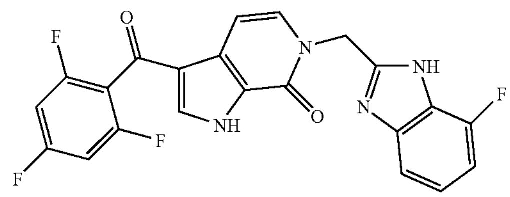 | 27 | 128 |
| 3 | 3 | 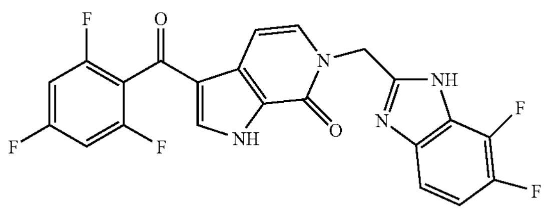 | 23 | 128 |
| 4 | 4 | 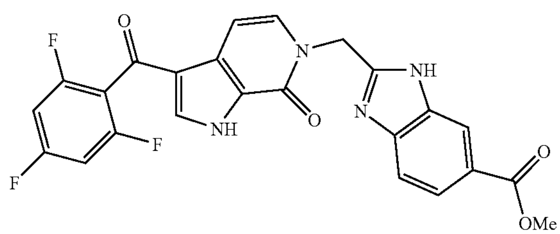 | | |
| 5 | 5 | 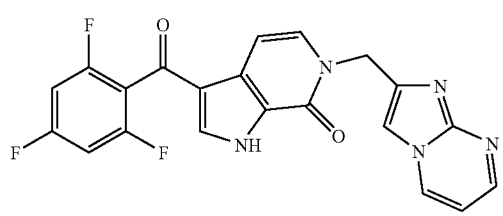 | 5.3 | 88 |
| 6 | 6 | 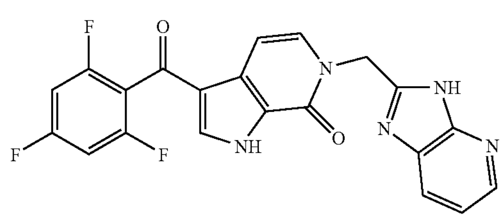 | 18 | 84 |
| 7 | 7 | 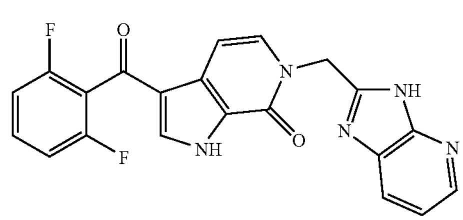 | 38 | 248 |

-continued

| Compound | Example | Structure | IC$_{50}$ p38α *peptide [nM] | IC$_{50}$ hWB [nM] |
| --- | --- | --- | --- | --- |
| 8 | 8 | 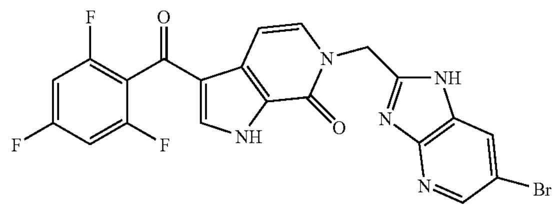 | 24 | 253 |
| 9 | 9 | 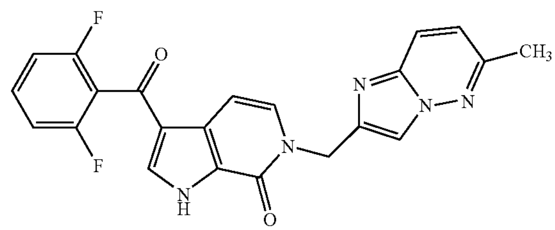 | 16 | 217 |
| 10 | 10 | 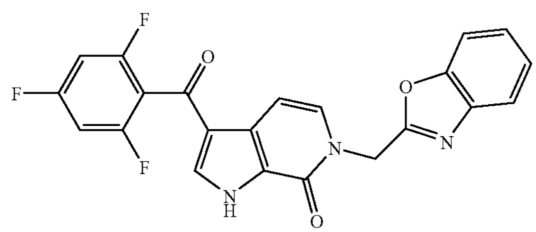 | 40 | 1368 |
| 11 | 11 | 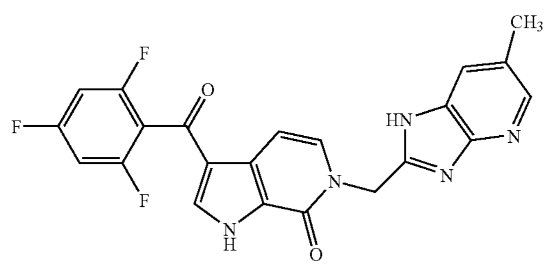 | 14 | 39 |
| 12 | 12 | 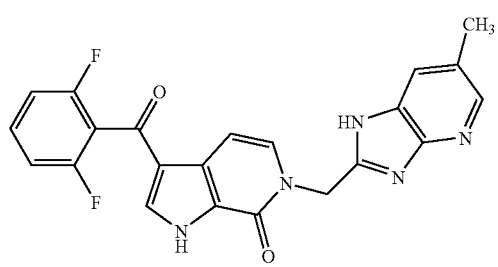 | 25 | 142 |
| 13 | 13 | 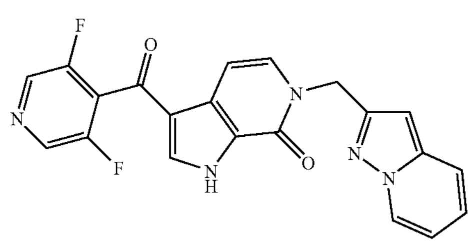 | 29 | 1518 |

-continued

| Compound | Example | Structure | IC$_{50}$ p38α *peptide [nM] | IC$_{50}$ hWB [nM] |
|---|---|---|---|---|
| 14 | 14 | 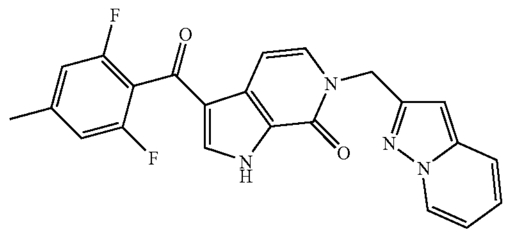 | 22 | 486 |
| 15 | 15 | 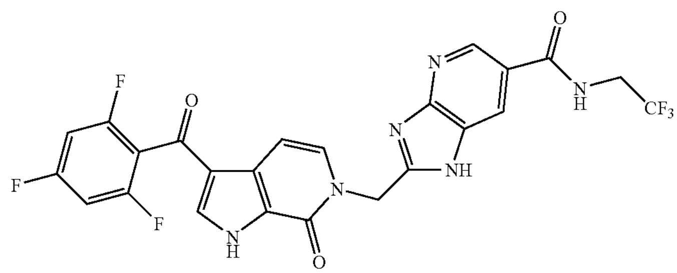 | 8.6 | 103 |
| 16 | 16 | 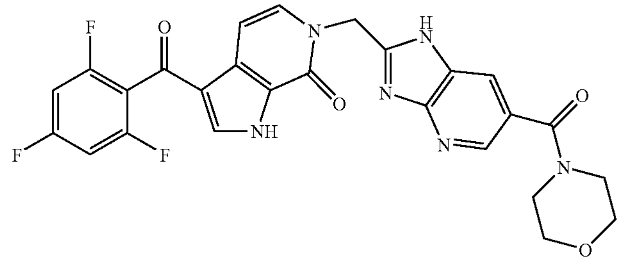 | 19 | 217 |
| 17 | 17 | 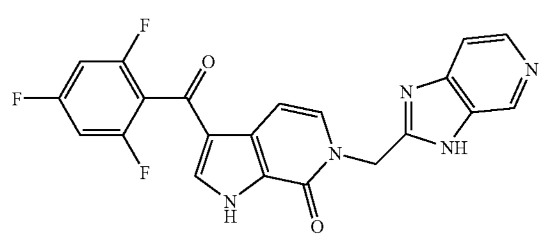 | 13 | |
| 18 | 18 | 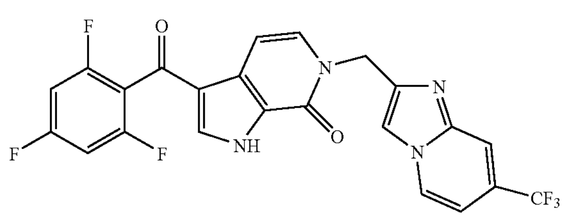 | 12 | 201 |
| 19 | 19 | 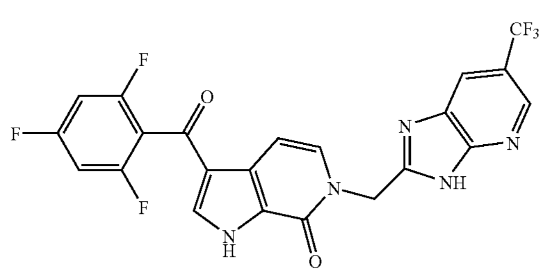 | 31 | 365 |

-continued

| Compound | Example | Structure | IC$_{50}$ p38α *peptide [nM] | IC$_{50}$ hWB [nM] |
|---|---|---|---|---|
| 20 | 20 | 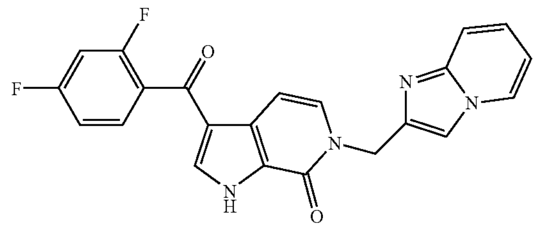 | 18 | 162 |
| 21 | 21 | 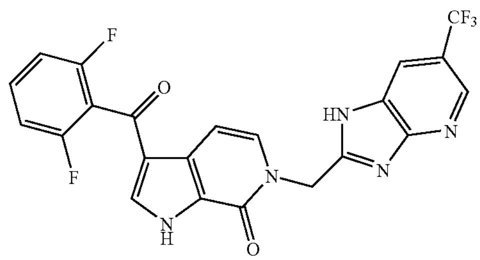 | 38 | 2060 |
| 22 | 22 | 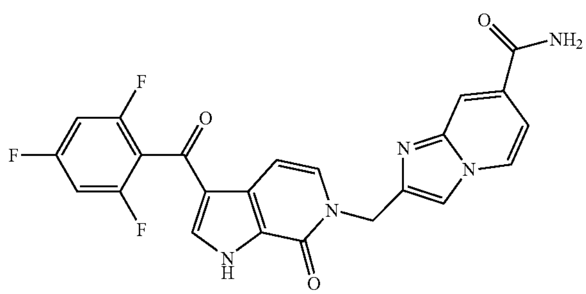 | 1.3 | |
| 23 | 23 | 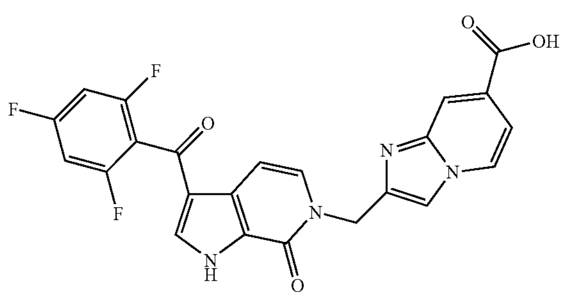 | 2.0 | |
| 24 | 24 | 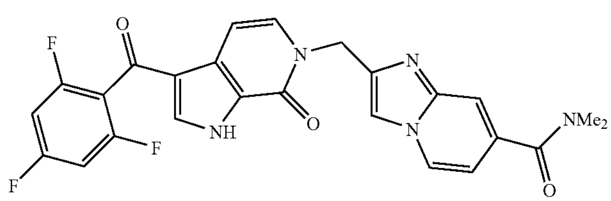 | 3.8 | 21 |
| 25 | 25 | 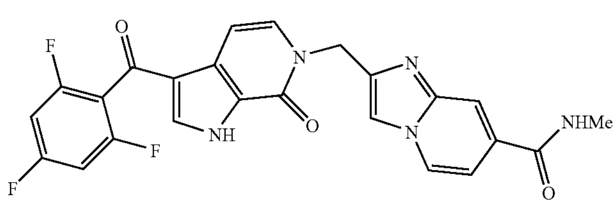 | 1.0 | |

| Compound | Example | Structure | IC₅₀ p38α *peptide [nM] | IC₅₀ hWB [nM] |
|---|---|---|---|---|
| 26 | 26 | 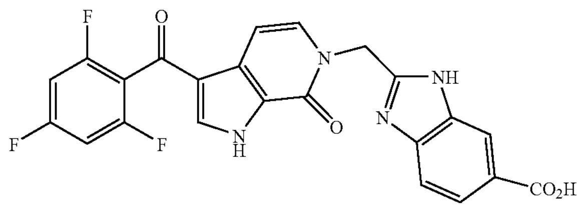 | | |
| 27 | 27 | 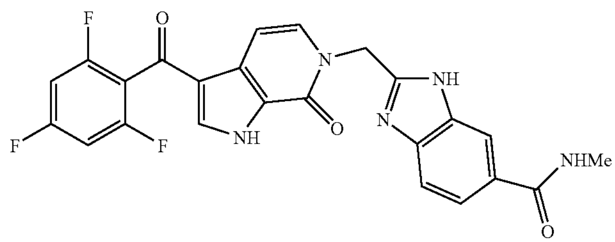 | 3.0 | |
| 28 | 28 | 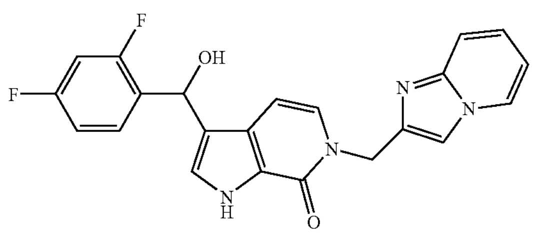 | 249 | |
| 29 | 29 | 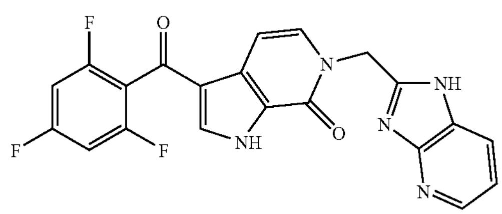 | 108 | 503 |

The abbreviations used herein are as follows unless specified otherwise:

| | |
|---|---|
| Bu | butyl |
| Bn | benzyl |
| BOC | t-butyloxycarbonyl |
| BOP | benzotriazol-1-yloxy tris/dimethylamino-phosphonium hexafluorophosphate |
| DCC | dicyclohexylcarbodiimide |
| DME | 1,2-dimethoxyethane |
| DMF | N,N-dimethylformamide |
| DMAP | 4-dimethylaminopyridine |
| EDC | 1-(3-dimethylaminopropyl_3-ethylcarbodi-imide hydrochloride |
| EtOAc | ethyl acetate |
| Eq. | equivalent(s) |
| HOBt, HOBT | hydroxybenztriazole |
| HPLC | high pressure liquid chromatography |
| LAH | lithium aluminum hydride |
| LCMS | liquid chromatography-mass spectrophotometer |
| LHMDS | lithium bis(trimethylsilyl)amide |
| MeOH | methanol |
| MHz | megahertz |
| MS(ES) | mass spectrophotometer-electon spray |
| NMP | N-methylpyrrolidinone |
| Ph | phenyl |
| Pr | propyl |
| TBAF | tetrabutylammonium fluoride |
| TEA | triethylamine |
| THF | tetrahydrofuran |
| TMEDA | N,N,N',N'-tetramethylethylenediamine |
| TLC | thin layer chromatography |
| Tetrakis | tetrakis(triphenylphosphine)palladium |

The present compounds can be prepared according to the general Schemes provided below as well as the procedures provided in the Intermediates and Examples. The following Schemes, Examples and Intermediates further describe, but do not limit, the scope of the invention. The substituents are the same as in the above Formulas except where defined otherwise or otherwise apparent to the ordinary skilled artisan.

The procedures described herein for synthesizing the compounds may include one or more steps of protecting group manipulations and of purification, such as, recrystallization, distillation, column chromatography, flash chromatography, thin-layer chromatography (TLC), radial chromatography and high-pressure chromatography (HPLC). The products can be characterized using various techniques well known in the chemical arts, including proton and carbon-13 nuclear magnetic resonance ($^1$H and $^{13}$C NMR), infrared and ultra-violet spectroscopy (IR and UV), X-ray crystallography, elemental analysis and HPLC and mass spectrometry (LC-MS). Methods of protecting group manipulation, purification, structure identification and quantification are well known to one skilled in the art of chemical synthesis.

It is understood that the functional groups present in compounds described in the Schemes below can be further manipulated, when appropriate, using the standard functional group transformation techniques available to those skilled in the art, to provide desired compounds described in this invention.

Other variations or modifications, which will be obvious to those skilled in the art, are within the scope and teachings of this invention. This invention is not to be limited except as set forth in the following claims.

Scheme 1

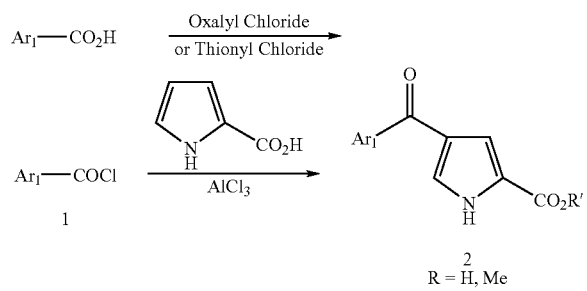

Compounds of Formula I can be synthesized as described in Scheme 1, 2 and 3. The appropriate acid chloride 1 can be prepared by the method know to those skilled in the art from the corresponding acid or commercially available material. Compound 2 can be readily synthesized from the compound 1 by any of several known procedure such as Friedel-Craft acylation with pyrrole-2-carboxylate.

Scheme 2

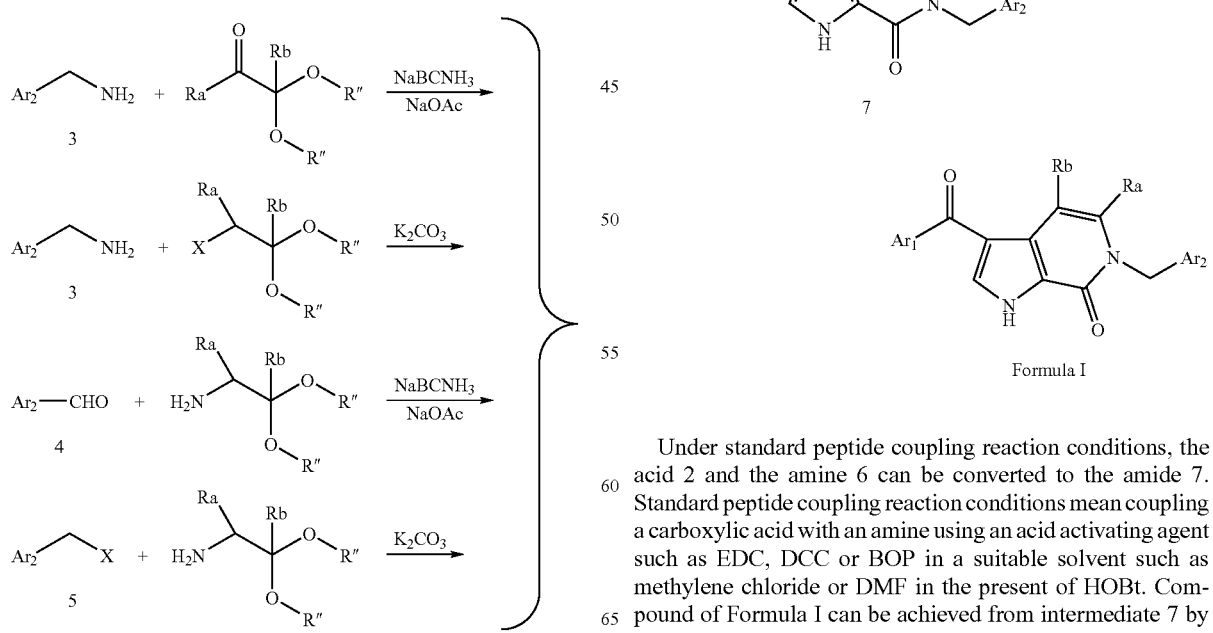

-continued

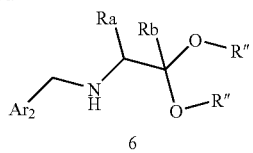

X = halides
R″ = Me, Et, CH$_2$

The compound 6 can be prepared from the appropriate aminomethyl heterocycle 3 using methods known in the art such as reductive alkylation or displacement reaction. Alternatively, the compound 6 can also be synthesized from the appropriate heterocyclic aldehyde 4 and halide 5 by using procedures similar to that described above.

Scheme 3

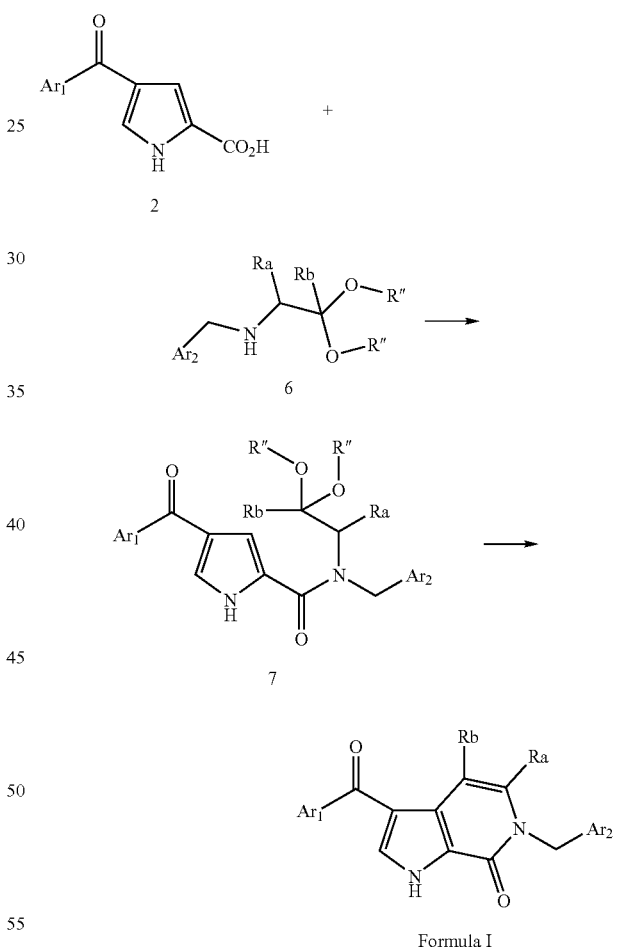

Under standard peptide coupling reaction conditions, the acid 2 and the amine 6 can be converted to the amide 7. Standard peptide coupling reaction conditions mean coupling a carboxylic acid with an amine using an acid activating agent such as EDC, DCC or BOP in a suitable solvent such as methylene chloride or DMF in the present of HOBt. Compound of Formula I can be achieved from intermediate 7 by employing an acid condition, such as methanesulfonic acid, pTSA and sulfuric acid.

Scheme 4

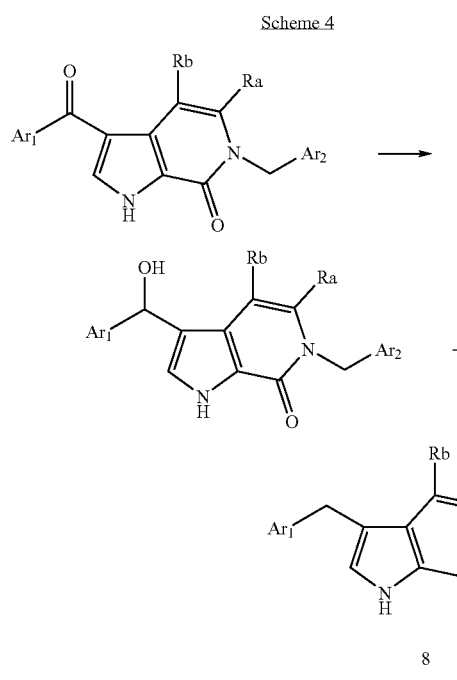

The keto functional group of compound of Formula I can further convert to des-keto and hydroxyl functional group through chemistry well known in the literature. For example the keto group can be reduced by sodium boronhydride to give hydroxyl moiety. The hydroxyl moiety can be further removed by hydrogenation in methanol with a catalytic amount of palladium on carbon. Alternatively, the de-keto compound 8 can be prepared one step by reaction with alkyl-silane in an acid condition.

Scheme 5

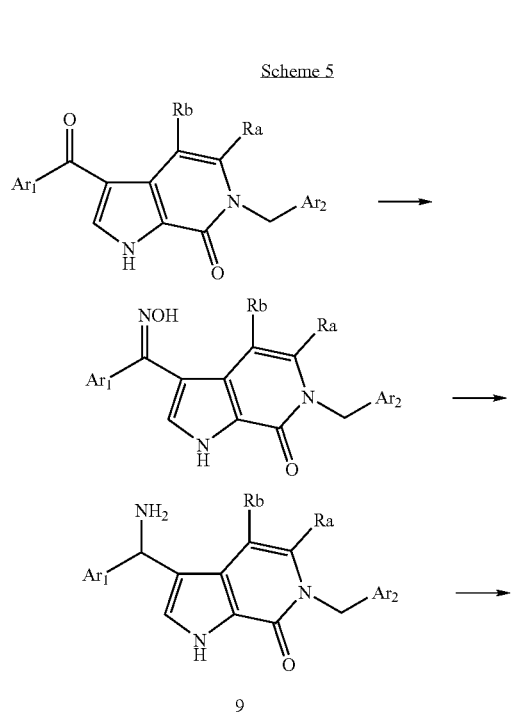

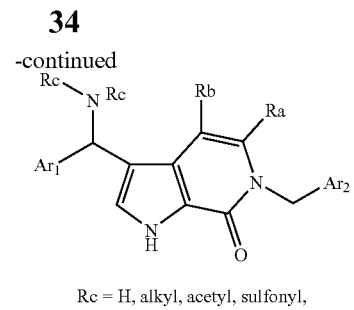

Rc = H, alkyl, acetyl, sulfonyl,

The keto functional group of compound of Formula I can also further convert to oxime and amine moiety by using the method known in the art. The resulting amine 9 can serve as a useful intermediate for further reaction such as acylation, sulfonylation and reductive alkylation.

Scheme 6

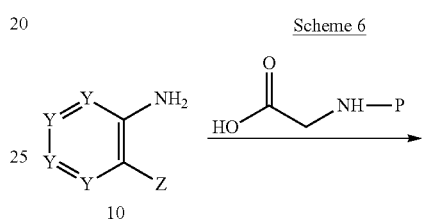

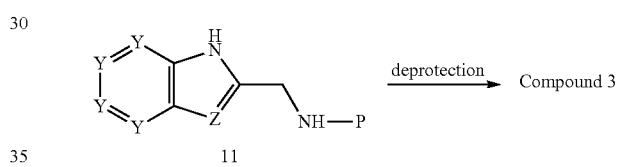

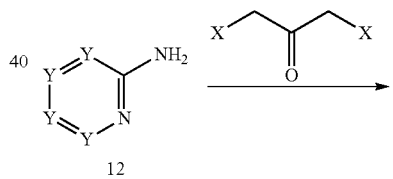

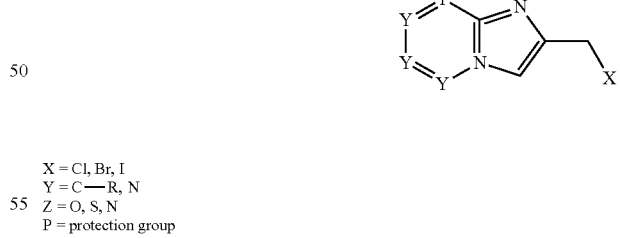

X = Cl, Br, I
Y = C—R, N
Z = O, S, N
P = protection group

Compound 3, 4, and 5 are commercially available or can be synthesized according to procedures known in the art. For example, compound 10 can react with glycine derivatives to give compound 11. The protection group can be removed using methods known in the art such as BOC group can be removed in acid conditions and benzyl group can be removed by hydrogenation. Compound 5 can be arrived from compound 12 and di-haloacetone according the procedure known in the art.

Scheme 7

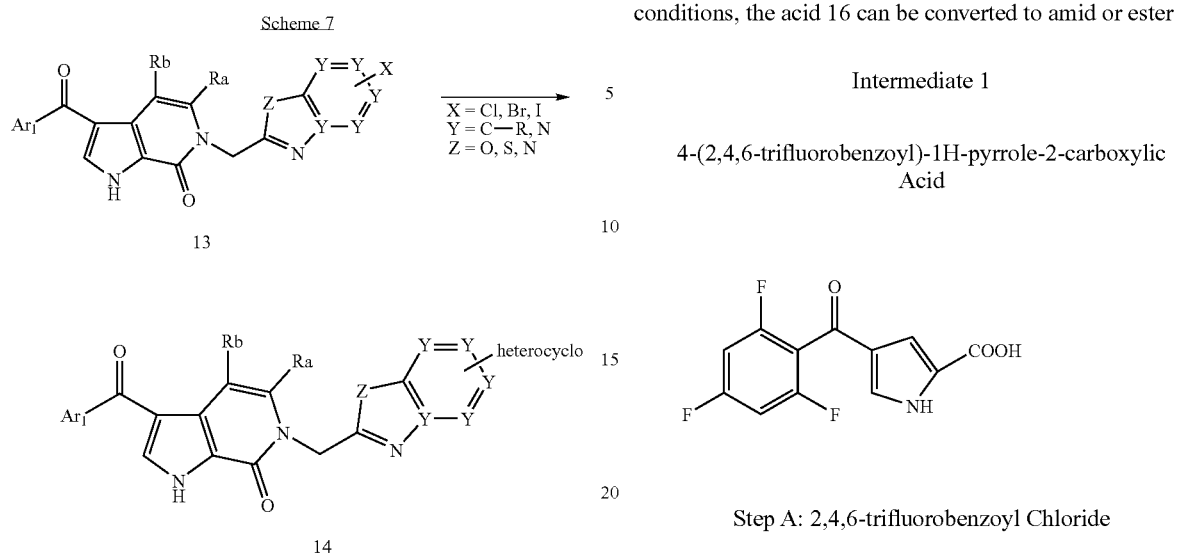

Compound 14 can be achieved from intermediate 13 by employing a variety of reaction conditions, such as standard Pd-mediated coupling using commercially available hertero-cyclic-tin or herterocyclic-boronic acids.

Scheme 8

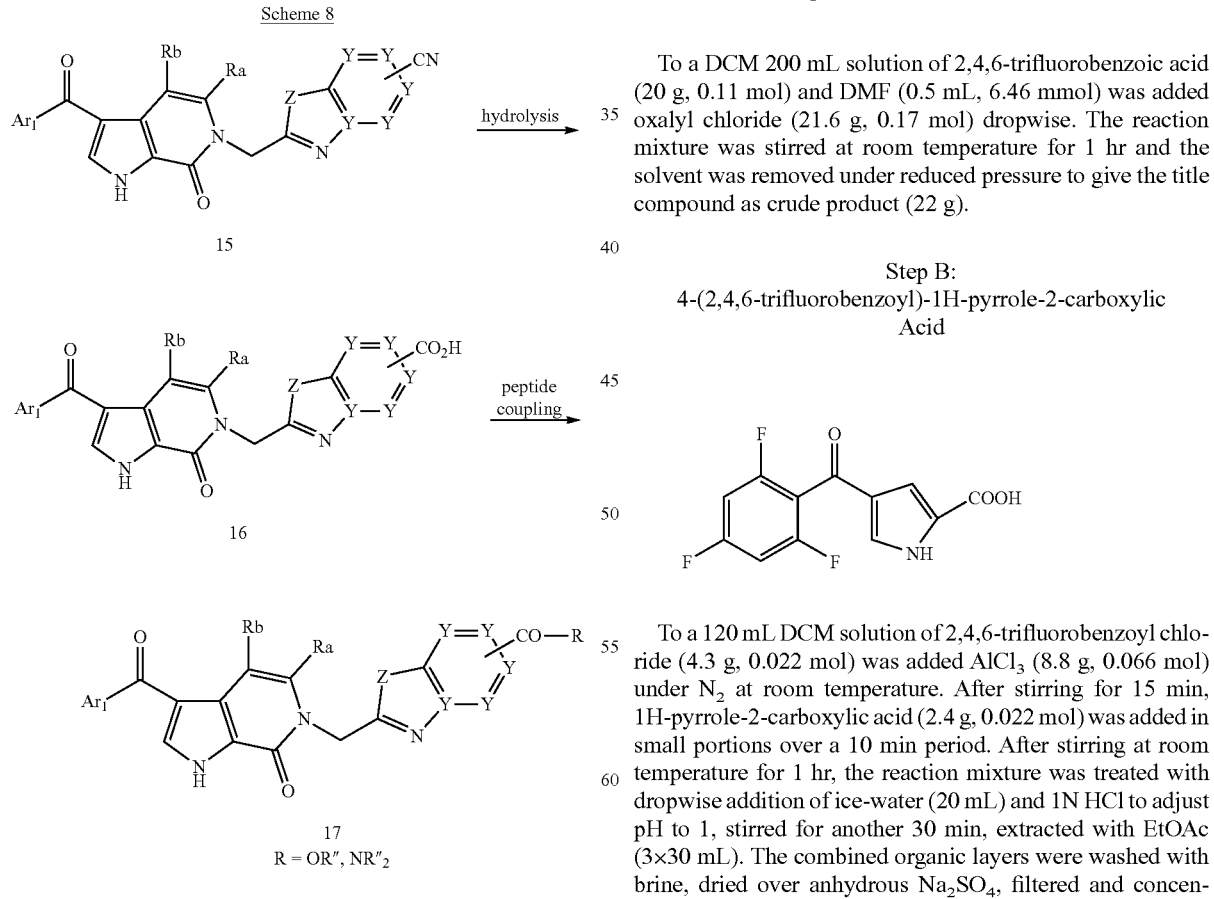

Hydrolysis of the nitrile 15 can be achieved by methods known to those skilled in the art to give the corresponding carboxylic acid 16. Under standard peptide coupling reaction conditions, the acid 16 can be converted to amid or ester 17.

Intermediate 1

4-(2,4,6-trifluorobenzoyl)-1H-pyrrole-2-carboxylic Acid

Step A: 2,4,6-trifluorobenzoyl Chloride

To a DCM 200 mL solution of 2,4,6-trifluorobenzoic acid (20 g, 0.11 mol) and DMF (0.5 mL, 6.46 mmol) was added oxalyl chloride (21.6 g, 0.17 mol) dropwise. The reaction mixture was stirred at room temperature for 1 hr and the solvent was removed under reduced pressure to give the title compound as crude product (22 g).

Step B: 4-(2,4,6-trifluorobenzoyl)-1H-pyrrole-2-carboxylic Acid

To a 120 mL DCM solution of 2,4,6-trifluorobenzoyl chloride (4.3 g, 0.022 mol) was added $AlCl_3$ (8.8 g, 0.066 mol) under $N_2$ at room temperature. After stirring for 15 min, 1H-pyrrole-2-carboxylic acid (2.4 g, 0.022 mol) was added in small portions over a 10 min period. After stirring at room temperature for 1 hr, the reaction mixture was treated with dropwise addition of ice-water (20 mL) and 1N HCl to adjust pH to 1, stirred for another 30 min, extracted with EtOAc (3×30 mL). The combined organic layers were washed with brine, dried over anhydrous $Na_2SO_4$, filtered and concentrated to give the title compound (5.8g, 97% yield). $^1$H-NMR (500 MHz, $CDCl_3$): δ 12.48 (br.s, 1H), 7.48 (s, 1H), 7.28-7.38 (m, 2H), 6.83 (s, 1H).

The following intermediates were prepared following the procedure for Intermediate 1, Steps A & B employing appropriately substituted carboxylic acids instead of 2,4,6-trifluorobenzoic acid.

Intermediate 2:
4-(2,6-difluorobenzoyl)-1H-pyrrole-2-carboxylic acid

Intermediate 3:
4-(2,4-difluorobenzoyl)-1H-pyrrole-2-carboxylic acid

Intermediate 4: 4-(3,5-difluoroisonicotinoyl)-1H-pyrrole-2-carboxylic acid

Intermediate 5

4-(2,6-difluoro-4-methylbenzoyl)-1H-pyrrole-2-carboxylic Acid

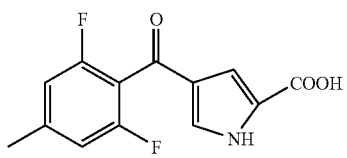

Step A: 1,3-difluoro-5-methylbenzene

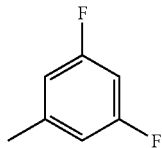

A mixture of 1-(bromomethyl)-3,5-difluorobenzene (50 g, 0.24 mol), 10% Pd/C (3 g) and sodium acetate (140 g, 1.7 mol) in anhydrous ether (250 mL) was stirred under hydrogen at atmospheric pressure for 24 hr. The mixture was filtered and the filtrate was dried over anhydrous Na$_2$SO$_4$, filtered and used directly in the next step. $^1$H-NMR (500 MHz, CDCl$_3$): δ 6.56 (d, 2H, J=6.0 Hz), 6.47 (t, 1H, J=9.0 Hz), 2.22 (s, 3H).

Step B: 2,6-difluoro-4-methylbenzaldehyde

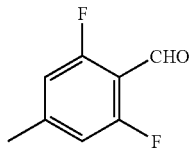

To a solution of 1,3-difluoro-5-methylbenzene (10.2 g, 80 mmol) in anhydrous ether (80 mL) was added n-BuLi (2.5 M solution in hexane, 48 ml, 120 mmol) over a 20 min period while the internal temperature was maintained at around −50° C. After stirring at that temperature for 1.5 hr, DMF (14.6 g, 200 mmol) was added over a 20 min period. After stirring at the same temperature for an additional 1.5 h, the reaction mixture was slowly poured into 1N aqueous sulfuric acid (300 mL) and extracted with ether three times. The combined organic layers were washed with brine, dried over anhydrous MgSO$_4$, filtered and concentrated to give the title compound (11.2 g, 90%). $^1$H-NMR (500 MHz, CDCl$_3$): δ 10.25 (s, 1H), 6.75 (d, 2H, J=9.9 Hz), 2.39 (s, 3H).

Step C: 2,6-difluoro-4-methylbenzoic Acid

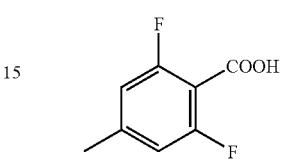

Silver oxide (43.8 g, 0.189 mol) was placed in a flask along with water (200 mL) and sodium hydroxide (33.7 g, 0.842 mol). To it was added 2,6-difluoro-4-methylbenzaldehyde (29.23 g, 0.187 mol) in small portions over a 30 min period. After a vigorous exothermic reaction, the color of the reaction mixture changed from black to gray. Resulting thick suspension was stirred for 1 hr, filtered through a Buchner funnel. The filtrate was acidified to pH 2 with concentrated HCl to give a suspension. The precipitate was collected by suction filtration, dissolved in ether and dried over anhydrous Na$_2$SO$_4$, filtered and concentrated to give white solid (17.0 g, 53%). $^1$H-NMR (500 MHz, d$^6$-DMSO): δ13.7 (br.s, 1H), 7.02 (d, 2H, J=9.3 Hz), 2.32 (s, 3H).

Step D: 4-(2,6-difluoro-4-methylbenzoyl)-1H-pyrrole-2-carboxylic Acid

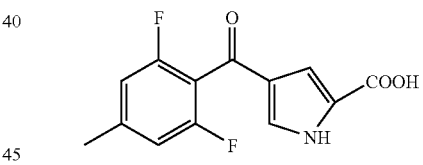

Title compound was synthesized following the procedure for Intermediate 1, Step A & B, employing 2,6-difluoro-4-methylbenzoic acid instead of 2,4,6-trifluorobenzoic acid. $^1$H-NMR (500 MHz, d$^6$-DMSO): δ 12.9 (br. s, 1H), 12.6 (s, 1H), 7.46 (s, 1H), 7.05 (d, 2H, J=8.8 Hz), 6.95 (s, 1H), 2.35 (s, 3H).

Intermediate 6

1-(4,5-difluoro-1H-benzimidazol-2-yl)methanamine di-hydrochloride

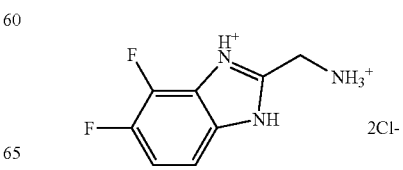

Step A: tert-butyl {2-[(2-amino-3,4-difluorophenyl)amino]-2-oxoethyl}carbamate

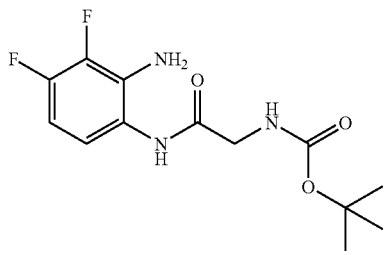

To a 130 mL DMF solution of [(tert-butoxycarbonyl)amino]acetic acid (14.1 g, 80.4 mmol) were added EDC (18.8 g, 96.2 mmol), HOBt (13.1 g, 96.2 mmol), 3,4-difluorobenzene-1,2-diamine (11.2 g, 77.7 mmol) and N,N-diisopropylethylamine (27.1 mL, 156 mmol). The reaction mixture was stirred at room temperature for 6 hr. The resulting suspension was filtered and the filtrate was diluted with EtOAc, washed with sat. ammonium chloride aq., sat. sodium bicarbonate aq. and brine, dried over anhydrous Na$_2$SO$_4$ filtered and concentrated to give the title compound as crude solid product (24 g). LC/MS: m/z 302(M+H).

Step B: tert-butyl [(4,5-difluoro-1H-benzimidazol-2-yl)methyl]carbamate

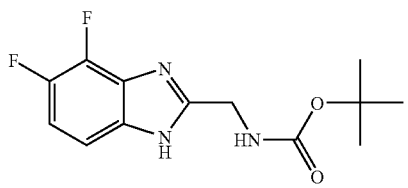

Crude product obtained in Step A was dissolved in glacial acetic acid (200 mL) and heated to 100° C. in an oil bath for 1 hr and cooled to room temperature. The mixture was diluted with EtOAc and washed with water, sat. sodium bicarbonate aq. and brine. The organic layer was separated, dried over anhydrous Na$_2$SO$_4$, filtered, concentrated and recrystallized from 2:1 EtOAc:hexanes (200 mL) to give the title compound (22 g). LC/MS: m/z 284(M+H).

Step C: 1-(4,5-difluoro-1H-benzimidazol-2-yl)methanamine di-hydrochloride

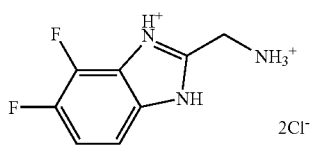

To a MeOH 144 mL solution of the product obtained in Step B (13.9 g, 48.9 mmol) was added acetyl chloride (16.6 g, 212 mmol) at room temperature. The reaction mixture (solution) was heated to 55° C. in an oil bath for 1 hr and then cooled to room temperature. Resulting suspension was cooled in an ice-water bath and the precipitate was collected by suction filtration and dried to give the title compound (12.5 g). LC/MS; m/z 184(M+H).

Intermediate 7 methyl 2-(aminomethyl)-1H-benzimidazole-5-carboxylate di-trifluoro Acetate

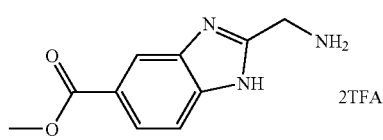

To a DCM 5 mL solution of methyl 2-{[(tert-butoxycarbonyl)amino]methyl}-1H-benzimidazole-5-carboxylate (710 mg, 2.33 mmol) was added trifluoroacetic acid (5 mL). After stirring at room temperature for 3 hr, the mixture was concentrated and recrysatllized from DCM to give the title compound (730 mg). LC/MS: m/z 206(M+H).

Intermediate 8

1-(6-methylimidazo[1,2-b]pyridazin-2-yl)methanamine

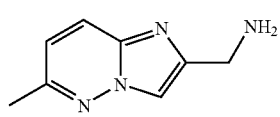

Step A: 2-(chloromethyl)-6-methylimidazo[1,2-b]pyridazine

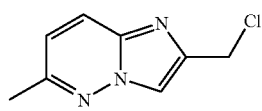

Starting with 3-chloro-6-methylpyridazine, the title compound was prepared following the literature procedure (Terme, T.; Galtier, C.; Maldonado, J.; Crozet, M. P.; Gueiffier, A.; Vanelle, P. *J. Heterocyclic Chem.* 2002, 39, 173).

Step B: 1-(6-methylimidazo[1,2-b]pyridazin-2-yl)methanamine

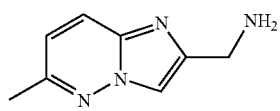

A mixture of 2-(chloromethyl)-6-methylimidazo[1,2-b]pyridazine (0.6 g, 3.3 mmol) and ammonium hydroxide (25%, 30 ml) was heated to 80° C. in a sealed tube for 1hr. The reaction mixture was concentrated under reduced pressure to give title compound as crude product. This material was used in the next step without further purification.

Intermediate 9

1-(6-methyl-3H-imidazo[4,5-b]pyridin-2-yl)methanamine

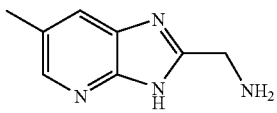

Starting with 5-methyl-3-nitropyridin-2-amine, the title compound was prepared following the literature procedure (Priepke, H.; Pfau, R; Gerlach, K.; Gillard, J.; Bauer, E.; Wienen, E.; Wolgang, H.; Sandra N. H. WO 2004056784, 2004).

Intermediate 10

2-(aminomethyl)-N-(2,2,2-trifluoroethyl)-3H-imidazo[4,5-b]pyridine-6-carboxamide

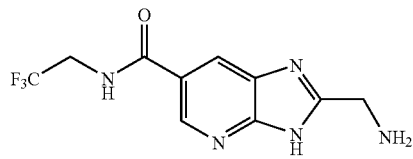

Step A: methyl 2-{[(tert-butoxycarbonyl)amino]methyl}-3H-imidazo[4,5-b]pyridine-6-carboxylate

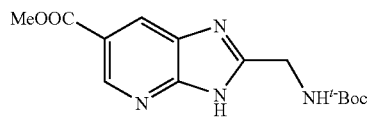

To a MeOH 25 mL solution of tert-butyl[(6-bromo-3H-imidazo[4,5-b]pyridin-2-yl)methyl]carbamate (Priepke, H.; Pfau, R; Gerlach, K.; Gillard, J.; Bauer, E.; Wienen, E.; Wolfgang, H.; Sandra N. H. WO 2004056784, 2004.) (1.2 g, 3.66 mmol) were added Et₃N (1.11 g, 11 mmol), Pd(dppf)Cl₂ (263 mg, 0.366 mmol). The reaction mixture was stirred at 80° C. under CO atmosphere (50 psi) for 24 hr. The reaction mixture was cooled to room temperature, filtered and the filtrate was concentrated, chromatographed on silica gel eluting with DCM: MeOH: TEA (50:1:0.01, v/v/v) to give the title compound (0.9 g, 82%).

Step B: 2-{[(tert-butoxycarbonyl)amino]methyl}-3H-imidazo[4,5-b]pyridine-6-carboxylic Acid

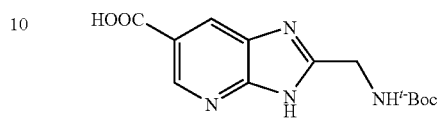

To a MeOH—H₂O (5:1) 72 mL solution of methyl 2-{[(tert-butoxycarbonyl)amino]methyl}-3H-imidazo[4,5-b]pyridine-6-carboxylate (11.0 g, 37.6 mmol) was added lithium hydroxide monohydrate (7.5 g, 179 mmol). After stirring at 60° C. for 4 hr, the reaction mixture was cooled to 0 acidified by 1N HCl to pH 5, concentrated and purified by Prep-HPLC (77×250 mm, JT BAKER C-18 RP column, 10μ particle size, linear gradient, 5% MeCN/H₂O+0.1% TFA to 35% MeCN/H₂O+0.1% TFA@200 mL/min) to give the title compound (7.5 g, 71%). MS (ESI): m/z 293(M+H). ¹H-NMR (400 MHz, d⁶-DMSO): δ 13.04 (br. s, 1H), 8.84 (s, 1H), 8.31 (s, 1H), 7.56 (s, 1H), 4.39 (s, 2H), 1.35 (s, 9H).

Step C: tert-butyl[(6-{[(2,2,2-trifluoroethyl)amino]carbonyl}-3H-imidazo[4,5-b]pyridin-2-yl)methyl]carbamate

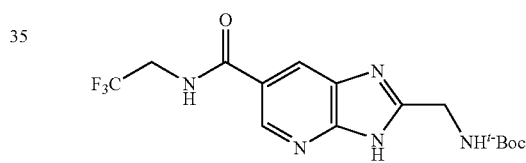

To a DMF 3 mL solution of 2-{[(tert-butoxycarbonyl)amino]methyl}-3H-imidazo[4,5-b]pyridine-6-carboxylic acid (293 mg, 1.0 mmol) were added HOBt (162 mg, 1.2 mmol), 2,2,2-trifluoroethanamine (130 mg, 1.5 mmol), DIPEA (388 mg, 3.0 mmol) and EDC (288 mg, 1.5 mmol). The reaction mixture was stirred at room temperature overnight and was partitioned between EtOAc and water. The organic layer was washed with brine twice, dried over anhydrous Na₂SO₄, and concentrated under reduced pressure. The residue was purified by prep TLC (MeOH/CH₂Cl₂=1/10, v/v) to give the title compound (0.26 g, 70%).

Step D: 2-(aminomethyl)-N-(2,2,2-trifluoroethyl)-3H-imidazo[4,5-b]pyridine-6-carboxamide

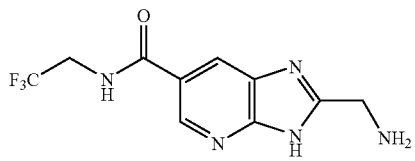

tert-butyl[(6-{[(2,2,2-trifluoroethyl)amino]carbonyl}-3H-imidazo[4,5-b]pyridin-2-yl)methyl]carbamate (0.657 g, 1.76 mmol) was treated with 4N HCl in dioxane (30 ml). The reaction mixture was stirred at room temperature overnight, concentrated under reduced pressure and co-evaporated with EtOAc twice to give title compound. This crude product was used in the next step without further purification.

Intermediate 11

1-[6-(morpholin-4-ylcarbonyl)-3H-imidazo[4,5-b]pyridin-2-yl]methanamine

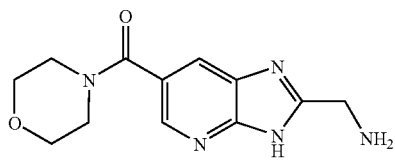

Intermediate 11 was prepared according to the procedure described for Intermediate 10, employing morpholine instead of 2,2,2-trifluoroethanamine.

The following intermediates were prepared according to the published procedures (Table A).

TABLE A

| Intermediate | Ar1 | Reference |
|---|---|---|
| 12 | imidazo[1,2-a]pyrimidin-2-ylmethanamine | WO2002 129195 A2 |
| 13 | 4-fluoro-1H-benzimidazol-2-ylmethanamine | WO02/08224 A1 |
| 14 | 3H-imidazo[4,5-b]pyridin-2-ylmethanamine | US2006/0252937 A1 |
| 15 | 6-bromo-3H-imidazo[4,5-b]pyridin-2-ylmethanamine | DE 10259407 A1 |
| 16 | 3H-imidazo[4,5-c]pyridin-2-ylmethanamine | EP 1847543 A1 |

Example 1

6-(1H-benzimidazol-2-ylmethyl)-3-(2,4,6-trifluorobenzoyl)-1,6-dihydro-7H-pyrrolo[2,3-c]pyridin-7-one

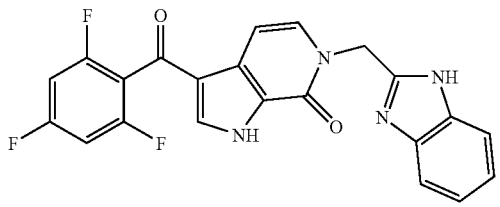

Step A: N-(1H-benzimidazol-2-ylmethyl)-2,2-dimethoxyethanamine

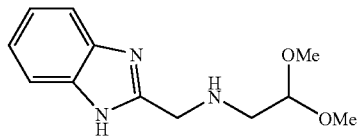

To a MeOH 150 mL suspension of 1-(1H-benzimidazol-2-yl)methanamine dihydrochloride (4.0 g, 18.2 mmol) were added dimethoxyacetaldehyde (1.89 g, 18.2 mmol, 60 wt. % solution in water), sodium acetate (7.45 g, 91 mmol) and sodium cyanoborohydride (9.09 mL, 9.09 mmol, 1.0 M THF solution). The reaction mixture was stirred at room temperature overnight, concentrated under reduced pressure and reconstituted in DCM (150 mL). The resulting suspension was filtered. The filtrate was concentrated and chromatographed on silica gel with a gradient solvent mixture (5% MeOH-DCM to 15% MeOH-DCM over 15 CV) to give the title compound as oil (3.1 g). LC/MS: m/z 205($M^+$-OMe). $^1$H-NMR (CDCl$_3$, 500 MHz) δ 3.02 (d, 1H), 3.36 (s, 6H), 4.40 (s, 211), 4.52 (t, 1H), 7.28-7.32 (m, 2H), 7.58-7.62 (m, 2H), 8.78-8.92 (br.s, 1H).

Step B: N-(1H-benzimidazol-2-ylmethyl)-N-(2,2-dimethoxyethyl)-4-(2,4,6-trifluorobenzoyl)-1H-pyrrole-2-carboxamide

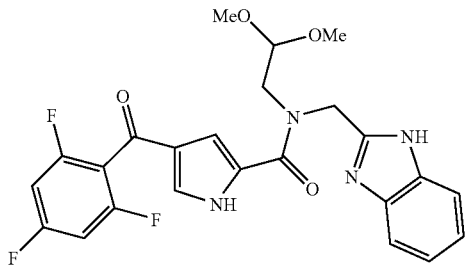

To a DMF 5 mL solution of product obtained in step A (693 mg, 2.95 mmol) were added 4-(2,4,6-trifluoro-benzoyl)-1H-pyrrole-2-carboxylic acid (793 mg, 2.95 mmol), EDC (678 mg, 3.53 mmol), HOBt (541 mg, 3.53 mmol) and triethylamine (0.821 mL, 5.89 mmol). The reaction mixture was stirred overnight at room temperature. Resulting suspension was filtered and diluted with EtOAc. The organic layer was washed with sat. ammonium chloride aq., sat. sodium bicarbonate aq. and brine. The organic layer was dried over anhydrous $Na_2SO_4$, filtered and concentrated to give the title compound as oil (930 mg). LC/MS: m/z 487(M+H). $^1$H-NMR (500 MHz, $CDCl_3$): δ 3.39 (s, 6H), 3.86 (br.s, 2H), 4.69 (d, 1H), 5.21 (s, 2H), 6.74 (t, 2H), 7.01 (br.s, 1H), 7.28 (s, 1H), 7.45 (dd, 2H), 7.65 (dd, 2H), 11.23 (s, 1H).

Step C: 6-(1H-benzimidazol-2-ylmethyl)-3-(2,4,6-trifluorobenzoyl)-1,6-dihydro-7H-pyrrolo[2,3-c]pyridin-7-one

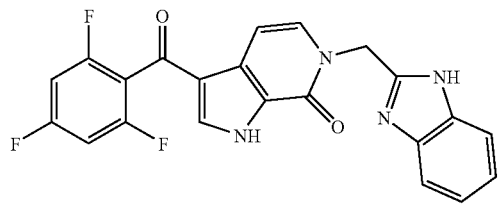

A methanesulofonic acid 1.5 mL solution of the product from Step B (910 mg, 1.87 mmol) was stirred at 95° C. in an oil bath for 25 min. The reaction mixture was cooled to room temperature, diluted with MeCN—$H_2O$ (2:3) mixture (3 mL). The resulting solution was purified by reverse phase HPLC (C-18 column) (eluent: gradient mixture of acetonitrile-water with 0.5% TFA) to give the title compound (414 mg). LC/MS: m/z 423(M+H). $^1$H-NMR ($d^6$-DMSO, 500 MHz): δ 5.59 (s, 2H), 7.06 (d, 1H), 7.35-7.39 (m, 4H), 7.61-7.68 (m, 3H), 7.93 (d, 1H), 13.14 (s, 1H).

Examples in Table 1 were prepared following the procedure for Example 1 employing appropriate $Ar^1$ and $Ar^2$ (Intermediates 1-16 and commercially available starting material).

TABLE 1-continued

| Example | Ar₁ | Ar₂ |
|---|---|---|
| 12 | 2,6-difluorophenyl | 6-methyl-3H-imidazo[4,5-b]pyridin-2-yl |
| 13 | 3,5-difluoropyridin-4-yl | pyrazolo[1,5-a]pyridin-2-yl |
| 14 | 2,6-difluoro-4-methylphenyl | pyrazolo[1,5-a]pyridin-2-yl |
| 15 | 2,4,5-trifluorophenyl | 2-{N-(2,2,2-trifluoroethyl)carboxamido}-3H-imidazo[4,5-b]pyridin-2-yl |
| 16 | 2,4,5-trifluorophenyl | 2-(morpholine-4-carbonyl)-3H-imidazo[4,5-b]pyridin-2-yl |
| 17 | 2,4,5-trifluorophenyl | 3H-imidazo[4,5-c]pyridin-2-yl |

Example 2

6-[(4-fluoro-1H-benzimidazol-2-yl)methyl]-3-(2,4,6-trifluorobenzoyl)-1,6-dihydro-7H-pyrrolo[2,3-c]pyridin-7-one LC/MS: m/z 441(M+H). ¹H-NMR (500 MHz, d⁶-DMSO): δ: 5.50 (s, 2H), 6.99-7.03 (m, 2H), 7.15 (m, 1H), 7.32-7.37 (m, 3H), 7.59 (d, 1H), 7.91 (d, 1H), 13.09 (s, 1H).

Example 3

6-[(4,5-difluoro-1H-benzimidazol-2-yl)methyl]-3-(2,4,6-trifluorobenzoyl)-1,6-dihydro-7H-pyrrolo[2,3-c]pyridin-7-one LC/MS: m/z 459(M+H). ¹H-NMR (500 MHz, d⁴-CD₃OD: d⁶-DMSO=3:1): δ 5.62 (s, 2H), 7.21-7.28 (m, 3H), 7.31-7.37 (m, 1H), 7.41 (dd, 1H), 7.65 (d, 1H), 7.88 (s, 1H).

Example 4 methyl 2-{[7-oxo-3-(2,4,6-trifluorobenzoyl)-1,7-dihydro-6H-pyrrolo[2,3-c]pyridin-6-yl]methyl}-1H-benzimidazole-6-carboxylate LC/MS: m/z 481 (M+H).

Example 5

6-(imidazo[1,2-a]pyrimidin-2-ylmethyl)-3-(2,4,6-trifluorobenzoyl)-1,6-dihydro-7H-pyrrolo[2,3-c]pyridin-7-one LC/MS: m/z 424(M+H). ¹H-NMR (500 MHz, d⁶-DMSO): δ 5.48 (s, 2H), 6.99 (t, 2H), 7.16 (dd, 1H), 7.35 (t, 2H), 7.57 (d, 1H), 7.86 (s, 1H), 7.88 (s, 1H), 8.27 (dd, 1H).

Example 6

6-(3H-imidazo[4,5-b]pyridin-2-ylmethyl)-3-(2,4,6-trifluorobenzoyl)-1,6-dihydro-7H-pyrrolo[2,3-c]pyridin-7-one LC/MS: m/z 424(M+H). ¹H-NMR (600 MHz, d⁶-DMSO): δ 5.55 (s, 2H), 7.01 (t, 2H), 7.22 (m, 2H), 7.52 (d, 1H), 7.74 (s, 1H), 7.91 (dd, 1H), 8.31 (dd, 1H).

Example 7

3-(2,6-difluorobenzoyl)-6-(3H-imidazo[4,5-b]pyridin-2-ylmethyl)-1,6-dihydro-7H-pyrrolo[2,3-c]pyridin-7-one LC/MS: m/z 406(M+H). ¹H-NMR (600 MHz, d⁶-DMSO): δ: 5.46 (s, 2H), 6.94 (d, 1H), 7.16 (dd, 1H), 7.24 (t, 2H), 7.55 (d, 1H), 7.58 (m, 1H), 7.74 (d, 1H), 7.85 (d, 1H), 8.26 (d, 1H).

Example 8

6-[(6-bromo-3H-imidazo[4,5-b]pyridin-2-yl)methyl]-3-(2,4,6-trifluorobenzoyl)-1,6-dihydro-7H-pyrrolo[2,3-c]pyridin-7-one LC/MS: m/z 504(M+H). ¹H-NMR (600 MHz, d⁶-DMSO): δ 5.50 (s, 2H), 7.02 (d, 1H), 7.35 (t, 2H), 7.61 (d, 1H), 7.91 (d, 1H), 8.22 (d, 1H), 8.36 (d, 1H).

Example 9

3-(2,6-difluorobenzoyl)-6-[(6-methylimidazo[1,2-b]pyridazin-2-yl)methyl]-1,6-dihydro-7H-pyrrolo[2,3-c]pyridin-7-one ¹H-NMR (CDCl₃, 500 MHz): δ 7.88 (br. s, 1H), 7.77 (d, 1H, J=9.4 Hz), 7.52 (s, 1H), 7.42 (m, 3H), 7.24 (d, 1H, J=7.1 Hz), 6.97 (m, 2H), 5.39 (s, 2H), 2.69 (s, 3H). LC/MS: m/z 420(M+H).

Example 10

6-(1,3-benzoxazol-2-ylmethyl)-3-(2,4,6-trifluorobenzoyl)-1,6-dihydro-7H-pyrrolo[2,3-c]pyridin-7-one ¹H-NMR (CDCl₃, 500 MHz): δ 7.68 (m, 1H), 7.54 (s, 1H), 7.50 (m, 1H) 7.32 (m, 4H), 6.78 (t, 2H), 5.52 (s, 2H). LC/MS: m/z 424(M+H).

Example 11

6-[(6-methyl-3H-imidazo[4,5-b]pyridin-2-yl)methyl]-3-(2,4,6-trifluorobenzoyl)-1,6-dihydro-7H-pyrrolo[2,3-c]pyridin-7-one ¹H-NMR (d⁴-CD₃OD, 500 MHz): δ 8.20 (s, 1H), 7.76 (m, 2H), 7.54 (d, 1H, J=7.3 Hz), 7.25 (d, 1H, J=7.1 Hz), 7.05 (m, 2H), 5.55 (s, 2H), 2.46 (s, 3H). LC/MS: m/z 438(M+H).

Example 12

3-(2,6-difluorobenzoyl)-6-[(6-methyl-3H-imidazo[4,5-b]pyridin-2-yl)methyl]-1,6-dihydro-7H-pyrrolo[2,3-c]pyridin-7-one $^1$H-NMR (d$^4$-CD$_3$OD, 500 MHz): δ 8.20 (s, 1H), 7.76 (s, 1H), 7.70 (s, 1H), 7.55 (m, 2H), 7.25 (d, 1H, J=7.0 Hz), 7.14 (m, 2H), 5.56 (s, 2H), 2.46 (s, 3H). LC/MS m/z 420(M+H).

Example 13

3-(3,5-difluoroisonicotinoyl)-6-pyrazolo[1,5-a]pyridin-2-ylmethyl)-1,6-dihydro-7H-pyrrolo[2,3-c]pyridin-7-one $^1$H-NMR (CDCl$_3$, 500 MHz): δ 8.60 (S, 1H), 8.45 (m, 1H), 7.82 (m, 1H), 7.48 (m, 2H), 7.20 (m, 2H), 6.82 (m, 1H), 6.49 (S, 1H), 5.49 (s, 2H). LC/MS: m/z 406(M+H).

Example 14

3-(2,6-difluoro-4-methylbenzoyl)-6-(pyrazolo[1,5-a]pyridin-2-ylmethyl)-1,6-dihydro-7H-pyrrolo[2,3-c]pyridin-7-one $^1$H-NMR (d$^4$-CD$_3$OD, 500 MHz): δ 8.47 (m, 1H), 7.63 (s, 1H), 7.58 (m, 1H), 7.45 (m, 1H), 7.19 (m, 2H), 6.97 (m, 2H), 6.85 (m, 1H), 6.44 (s, 1H), 5.50 (s, 2H), 2.42 (s, 3H). LC/MS: m/z 419(M+H).

Example 15

2-{[7-oxo-3-(2,4,6-trifluorobenzoyl)-1,7-dihydro-6H-pyrrolo[2,3-c]pyridin-6-yl]methyl}-N-(2,2,2-trifluoroethyl)-3H-imidazo[4,5-b]pyridine-6-carboxamide $^1$H-NMR (d$^4$-CD$_3$OD, 500 MHz): δ 8.86 (s, 1H), 8.39 (s, 1H), 7.77 (s, 1H), 7.58 (m, 1H), 7.27 (m, 1H), 7.05 (m, 2H), 5.60 (s, 2H), 4.23 (m, 2H). LC/MS: m/z 549(M+H).

Example 16

6-{[6-(morpholin-4-ylcarbonyl)-1H-imidazo[4,5-b]pyridin-2-yl]methyl}-3-(2,4,6-trifluorobenzoyl)-1,6-dihydro-7H-pyrrolo[2,3-c]pyridin-7-one $^1$H-NMR (d$^4$-CD$_3$OD, 500 MHz): δ 8.44 (d, 1H, J=1.8 Hz), 8.01 (d, 1H, J=1.8 Hz), 7.77 (s, 1H), 7.56 (d, 1H, J=7.3 Hz), 7.26 (d, 1H, J=7.1 Hz), 7.05 (m, 2H), 5.60 (s, 2H), 3.81-3.62 (m, 4H). LC/MS: m/z 537 (M+H).

Example 17

6-(3H-imidazo[4,5-c]pyridin-2-ylmethyl)-3-(2,4,6-trifluorobenzoyl)-1,6-dihydro-7H-pyrrolo[2,3-c]pyridin-7-one $^1$H-NMR (500 MHz, d$^6$-DMSO) δ: 5.50 (s, 2H), 6.90 (d, 1H), 7.36 (t, 2H), 7.49 (d, 1H), 7.58 (d, 1H), 7.87 (s, 1H), 8.24 (d, 1H), 8.80 (s, 1H). LC/MS: m/z 424(M+H).

Intermediate 17

2-(chloromethyl)imidazo[1,2-a]pyridine-7-carbonitrile hydrochloride

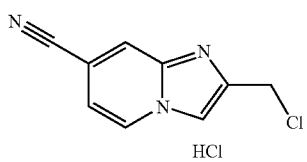

To an ethanol 50 mL solution of 2-amino-isonicotinonitrile (5.0 g, 42 mmol) was added 1,3-dichloroacetone (6.93 g, 54.6 mmol). The mixture was heated to reflux for 1.5 hr and cooled to room temperature to give a suspension. The precipitate was collected by suction filtration, washed with dichloromethane and dried to give the title compound (7.2 g). LC/MS: m/z 192(M+H).

Intermediate 18

2-(chloromethyl)-6-(trifluoromethyl)-3H-imidazo[4,5-b]pyridine

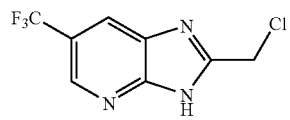

Step A: 3-nitro-5-(trifluoromethyl)pyridin-2-amine

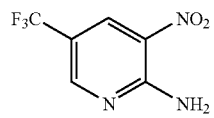

To a solution of 5-(trifluoromethyl)pyridine-2-amine (1.1 g, 6.79 mmol) dissolved in sulfuric acid (20 mL) at room temperature was added nitric acid (0.475 g, 6.79 mmol). After heating to 70° C. for 1 hr, the reaction mixture was cooled to room temperature and diluted with EtOAc and ice. The organic layer was separated, washed with sat. sodium bicarbonate aq. and brine, dried over anhydrous Na$_2$SO$_4$, filtered, concentrated under reduced pressure and chromatographed on silica gel eluting with a gradient solvent mixture (5% MeOH-DCM to 15% MeOH-DCM) to give the title compound (680 mg). LC/MS: m/z 208(M+H). $^1$H-NMR (500 MHz, CD$_3$OD): δ 8.60 (d, 1H), 8.67 (d, 1H).

Step B: 5-(trifluoromethyl)pyridine-2,3-diamine

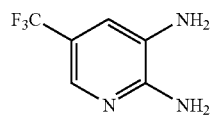

To a methanol 5 mL solution of 3-nitro-5-(trifluoromethyl)pyridin-2-amine (680 mg, 3.28 mmol) was added Raney nickel (240 mg charged as a wet slurry, washed 3× with 10 mL of H$_2$O). The mixture was hydrogenated in a Parr shaker at 50 psi at room temperature for 1 hr, purged with N$_2$ and filtered through a pad of celite. The celite pad was washed with methanol (5 mL×3). The filtrate was concentrated under reduced pressure to give the title compound (454 mg). LC/MS: m/z 178(M+H).

Step C: 2-(chloromethyl)-6-(trifluoromethyl)-3H-imidazo[4,5-b]pyridine

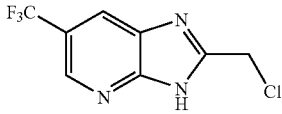

To a DCM 2 mL suspension of 5-(trifluoromethylpyridine-2,3-diamine (454 mg, 2.56 mmol) was added 2-Chloro-1,1,1-triethoxy-ethane (504 mg, 2.56 mmol). The mixture was heated to 100° C. for 20 min using a microwave reactor and resulting solid was suspended in 1:1 DCM:hexanes (5 mL) and gently sonicated. The precipitate was collected by suction filtration to give the title compound (324 mg). LC/MS: m/z 236(M+H). $^1$H-NMR (500 MHz, d$^6$-DMSO): δ4.98 (s, 2H), 8.42 (d, 1H), 8.72 (d, 1H).

Intermediate 19

2-(chloromethyl)-7-(trifluoromethyl)-imidazo[1,2-a]pyridine

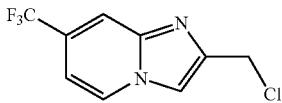

Following the procedure for Intermediate 17, title compound was prepared employing 4-(trifluoromethyl)pyridin-2-amine instead of 2-amino-isonicotinonitrile. LC/MS: m/z 235(M+H).

Example 18

3-(2,4,6-trifluorobenzoyl)-6-{[(7-trifluoromethyl)imidazo[1,2-a]pyridin-2-yl]methyl}-1,6-dihydro-7H-pyrrolo[2,3-c]pyridin-7-one

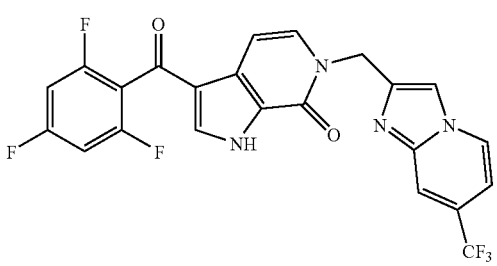

Step A: 1-(1,3-dioxolan-2-yl)-N-{[7-(trifluoromethyl)imidazo[1,2-a]pyridin-2-yl]methyl}methanamine

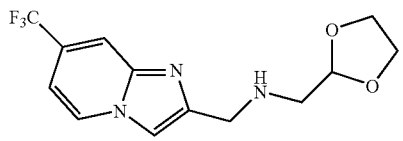

To a DCM 5 mL solution of 1-(1,3-dioxolan-2-yl)methanamine (814 mg, 7.89 mmol) was added 2-(chloromethyl)-7-(trifluoromethyl)imidazo[1,2-a]pyridine (Intermediate 19) (620 mg, 2.63 mmol). After heating to reflux for 1.5 hr, the reaction mixture (suspension) was cooled to room temperature and concentrated under reduced pressure. The residue was chromatographed on silica gel eluting with a gradient solvent mixture (5% MeOH-DCM to 15% MeOH-DCM) to give the title compound as solid (450 mg). LC/MS: m/z 302 (M+H).

Step B: N-(1,3-dioxolan-2-ylmethyl)-4-(2,4,6-trifluorobenzoyl)-N-{[7-(trifluoromethyl)imidazo[1,2-a]pyridin-2-yl]methyl}-1H-pyrrole-2-carboxamide

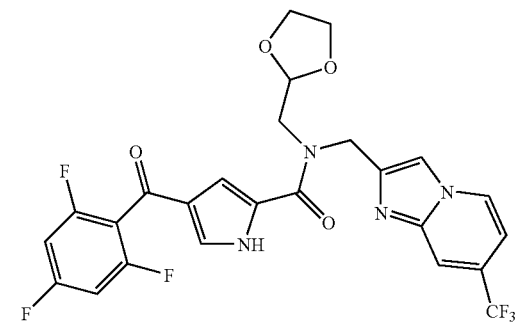

To a DMF 10 mL solution of 1-(1,3-dioxolan-2-yl)-N-{[7-(trifluoromethyl)imidazo[1,2-a]pyridin-2-yl]methyl}methanamine (1.13 g, 3.75 mmol) were added 4-(2,4,6-trifluorobenzoyl)-1H-pyrrole-2-carboxylic acid (1.06 g, 3.94 mmol), EDC (1.08 g, 5.63 mmol), HOBt (862 mg, 5.63 mmol) and triethyl amine (1.57 mL, 11.25 mmol). The mixture was stirred at room temperature overnight. The resulting suspension was diluted with EtOAc. The organic phase was washed with sat. ammonium chloride aq., sat. aq. sodium bicarbonate aq. and brine, dried over anhydrous Na$_2$SO$_4$, filtered, concentrated and chromatographed on silica gel eluting with a gradient solvent mixture (100% DCM to 5% MeOH-DCM) to give the title compound as foam (744 mg). LC/MS: m/z 533(M+H).

Step C: 3-(2,4,6-trifluorobenzoyl)-6-{[7-(trifluoromethyl)imidazo[1,2-a]pyridin-2-yl]methyl}-1,6-dihydro-7H-pyrrolo[2,3-c]pyridin-7-one

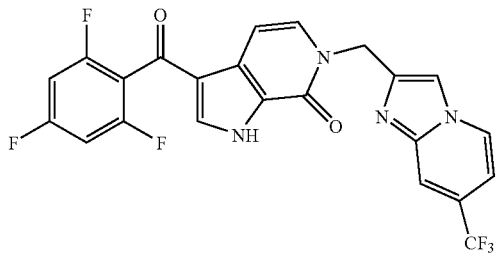

The product from Step B (744 mg, 1.40 mmol) was dissolved in methanesulfonic acid (6.0 mL) and heated to 85° C. for 50 min. After cooling in an ice-water bath, the reaction mixture was taken up in 2:3 MeCN—H₂O (10 mL) and purified by reverse phase HPLC (C-18 column) to give the title compound (430 mg). LC/MS: m/z 491(M+H). ¹H-NMR (d⁶-DMSO, 500 MHz): δ 5.40 (s, 2H), 6.96 (d, 1H), 7.20 (dd, 1H), 7.33 (t, 2H), 7.57 (d, 1H), 7.88 (d, 1H), 8.01 (s, 1H), 8.03 (s, 1H), 8.71 (d, 1H), 13.09 (s, 1H).

Examples in Table 2 were prepared following the procedures for Example 18 employing appropriate intermediates for Ar1 and Ar2 (Intermediates 1, 2, 3, 19 and commercially available material).

TABLE 2

| Example | Ar1 | Ar2 |
|---|---|---|
| 19 | 2,4,6-trifluorophenyl | 6-(trifluoromethyl)-3H-imidazo[4,5-b]pyridin-2-yl |
| 20 | 2,4-difluorophenyl | imidazo[1,2-a]pyridin-2-yl |
| 21 | 2,6-difluorophenyl | 6-(trifluoromethyl)-3H-imidazo[4,5-b]pyridin-2-yl |

Example 19

3-(2,4,6-trifluorobenzoyl)-6-{[6-(trifluoromethyl)-3H-imidazo[4,5-b]pyridin-2-yl]methyl}-1,6-dihydro-7H-pyrrolo[2,3-c]pyridin-7-one LC/MS: m/z 492(M+H). ¹H-NMR (500 MHz, d⁶-DMSO): δ 5.50 (s, 2H), 7.02 (d, 1H), 7.35 (t, 2H), 7.60 (d, 1H), 7.90 (d, 1H), 8.32 (br.s, 1H), 8.66 (s, 1H), 13.05 (d, 1H).

Example 20

3-(2,4-difluorobenzoyl)-6-(imidazo[1,2-a]pyridin-2-ylmethyl)-1,6-dihydro-7H-pyrrolo[2,3-c]pyridin-7-one LC/MS: m/z 405(M+H). ¹H-NMR (500 MHz, d⁶-DMSO): δ 5.46 (s, 2H), 7.04 (d, 1H), 7.20 (m, 1H), 7.37 (m, 2H), 7.57 (d, 1H), 7.64 (m, 1H), 7.75 (d, 1H), 7.82 (m, 2H), 8.14 (s, 1H), 8.74 (d, 1H), 12.98 (d, 1H).

Example 21

3-(2,6-difluorobenzoyl)-6-{[6-(trifluoromethyl)-3H-imidazo[4,5-b]pyridin-2-yl]methyl}-1,6-dihydro-7H-pyrrolo[2,3-c]pyridin-7-one ¹H-NMR (500 MHz, d⁶-DMSO): δ 8.58 (d, 1H, J=1.6 Hz), 8.21 (d, 1H, J=1.6 Hz); 7.76 (s, 1H), 7.61 (app. pent. 1H), 7.58 (d, 1H, J=7.1 Hz), 7.26 (t, 2H, J=7.8 Hz), 6.95 (d, 1H, J=7.1 Hz), 5.51 (s, 2H).

Example 22

2-{[7-oxo-3-(2,4,6-trifluorobenzoyl)-1,7-dihydro-6H-pyrrolo[2,3-c]pyridin-6-yl]methyl}imidazo[1,2-a]pyridine-7-carboxamide

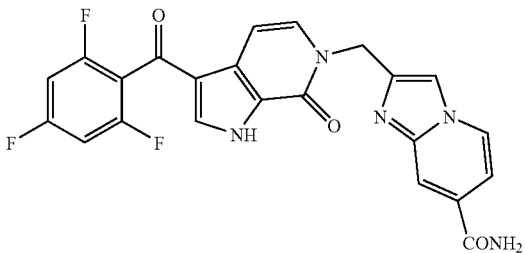

Step A: 2-{[(1,3-dioxolan-2-ylmethyl)-amino]-methyl}imidazo[1,2-a]pyridine-7-carbonitrile

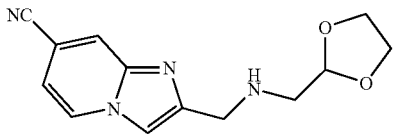

To a DCM solution of 1-(1,3-dioxolan-2-yl)methanamine (799 mg, 7.83 mmol) was added 2-(chloromethyl)imidazo[1,2-a]pyridine-7-carbonitrile hydrochloride (Intermediate 17) (500 mg, 2.61 mmol). After heating to reflux for 1 hr, the reaction mixture was cooled room temperature, concentrated under reduced pressure, chromatographed on silica gel eluting with a gradient solvent mixture (5% MeOH-DCM to 15% MeOH-DCM) to give the title compound as oil (410 mg). LC/MS: m/z 259(M+H).

Step B: N-[(7-cyanoimidazo[1,2-a]pyridine-2-yl)methyl]-N-(1,3-dioxolan-2-ylmethyl)-4-(2,4,6-trifluorobenzoyl)-1H-pyrrole-2-carboxamide

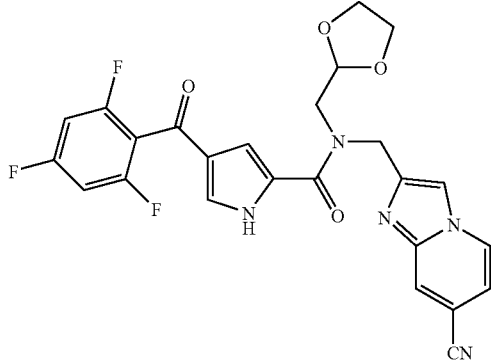

To a DMF 3 mL solution of product obtained in step A (410 mg, 1.58 mmol) were added 4-(2,4,6-trifluoro-benzoyl)-1H-pyrrole-2-carboxylic acid (427 mg, 1.58 mmol), EDC (396 mg, 2.06 mmol), HOBt (316 mg, 2.06 mmol) and triethylamine (0.443 mL, 3.17 mmol). The reaction mixture was stirred overnight at room temperature. The resulting suspension was filtered and diluted with EtOAc, washed with sat. ammonium chloride aq., sat. sodium bicarbonate aq. and brine, dried over anhydrous $Na_2SO_4$, filtered and concentrated to give the title compound as foam (430 mg). LC/MS: m/z 510(M+H).

Step C: 2-{[7-Oxo-3-(2,4,6-trifluorobenzoyl)-1,7-dihydro-6H-pyrrolo[2,3-c]pyridin-6-yl]methyl}imidazo[1,2-a]pyridine-7-carboxamide

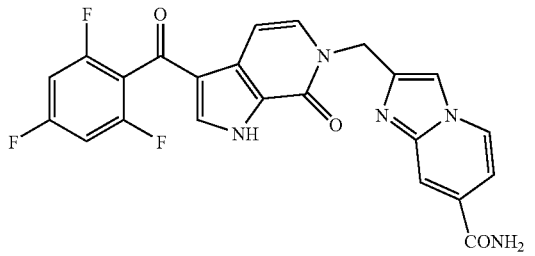

The product from step B (430 mg, 0.884 mmol) was dissolved in methanesulfonic acid (2.0 mL) and heated to 95° C. in an oil bath for 25 min. After cooling in an ice-water bath, the reaction mixture was diluted with 2:3 MeCN—$H_2O$ (3 mL) and purified by reverse phase HPLC (C-18 column) to give the title compound (174 mg). LC/MS: m/z 467(M+H). $^1$H-NMR ($d^6$-DMSO, 500 MHz): δ 5.46 (s, 2H), 7.01 (d, 1H), 7.33 (t, 2H), 7.58-7.59 (m, 2H), 7.61 (s, 1H), 7.79 (s, 1H), 7.91 (d, 1H) 8.12 (d, 1H), 8.33 (s, 1H), 8.72 (d, 1H), 13.12 (s, 1H).

Example 23

2-{[7-oxo-3-(2,4,6-trifluorobenzoyl)-1,7-dihydro-6H-pyrrolo[2,3-c]pyridin-6-yl]methyl}imidazo[1,2-a]pyridine-7-carboxylic acid

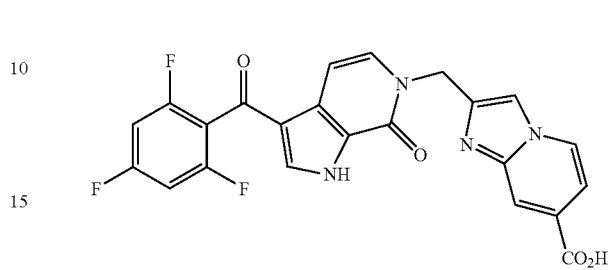

To the product obtained in example 22 (40 mg, 0.083 mmol) suspended in $H_2O$ (0.5 mL) was added conc. HCl (0.68 mL, 8.31 mmol). The mixture was placed in a microwave reactor and heated to 100° C. for 10 min. Resulting suspension was diluted with 3:1 MeCN:$H_2O$ (2 mL) along with DMSO (1 mL) and purified by reverse phase HPLC (C-18 column) to give the title compound (29 mg). LC/MS: m/z 468(M+H). $^1$H-NMR (600 MHz, $d^6$-DMSO): δ 5.45 (s, 2H), 6.98 (d, 1H), 7.32 (t, 2H), 7.53 (d, 1H), 7.61 (d, 1H), 7.88 (d, 1H), 8.15 (s, 1H), 8.17 (d, 1H), 8.71 (d, 1H).

Example 24

N,N-dimethyl-2-{[7-oxo-3-(2,4,6-trifluorobenzoyl)-1,7-dihydro-6H-pyrrolo[2,3-c]pyridin-6-yl]methyl}imidazo[1,2-a]pyridine-7-carboxamide

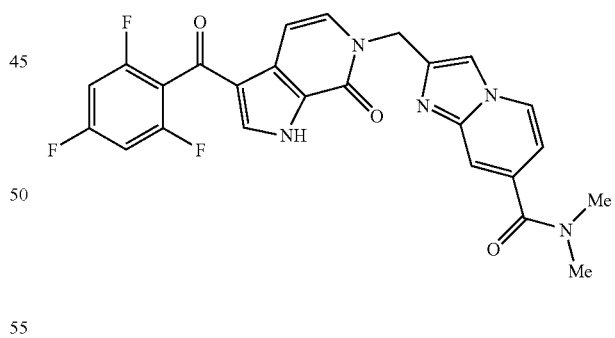

To the product obtained in Example 23 (4.7 mg, 0.010 mmol) in DMF were added EDC (2.51 mg, 0.013 mmol), HOBt (2.06 mg, 0.013 mmol) and dimethylamine (3.83 μL, 0.030 mmol). After stirring at room temperature overnight, the reaction mixture was diluted with 3:2 MeCN:$H_2O$ (2 mL) and purified by reverse phase HPLC (C-18 column) to give the title compound (3.1 mg). LC/MS: m/z 494(M+H). $^1$H-NMR (500 MHz, $d^6$-DMSO): δ 2.92 (s, 3H), 2.99 (s, 3H), 5.43 (s, 2H), 6.99 (d, 1H), 7.15 (d, 1H), 7.33 (t, 2H), 7.58 (d, 1H), 7.73 (s, 1H), 7.89 (d, 1H), 8.03 (s, 1H), 8.66 (d, 1H), 13.1 (d, 1H).

Example 25

N-methyl-2-{[7-oxo-3-(2,4,6-trifluorobenzoyl)-1,7-dihydro-6H-pyrrolo-[2,3-c]pyridin-6-yl]methyl}-imidazo[1,2-a]pyridine-7-carboxamide

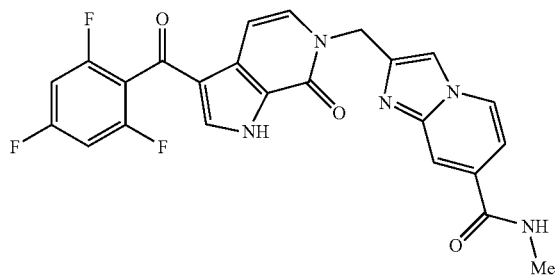

Following the procedure for Example 24, the titled compound was prepared employing methylamine in ethanol instead of dimethylamine. LC/MS: m/z 480(M+H). $^1$H-NMR (600 MHz, d$^6$-DMSO): δ 2.78 (d, 3H), 5.38 (s, 2H), 6.96 (d, 1H), 7.32 (t, 2H), 7.38 (d, 1H), 7.56 (d, 1H), 7.87 (d, 1H), 7.94 (s, 1H), 8.04 (s, 1H), 8.58 (d, 1H), 8.68 (d, 1H).

Example 26

2-{[7-oxo-3-(2,4,6-trifluorobenzoyl)-1,7-dihydro-6H-pyrrolo[2,3-c]pyridin-6-yl]methyl}-1H-benzimidazole-5-carboxylic Acid

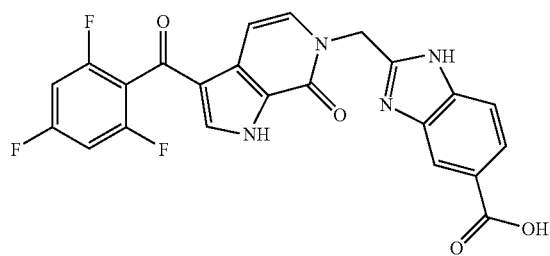

Upon cooling in an ice-water bath, to a methanesulfonic acid solution of the product obtained in example 4 was added H$_2$O (1 mL). The mixture was heated to 70° C. in an oil bath for 1.5 hr. After cooling to room temperature, the reaction mixture was diluted with 2:3 MeCN:H$_2$O (3 mL) and purified by reverse phase HPLC (C-18 column) to give the title compound. LC/MS: m/z 467(M+H).

Example 27

N-methyl-2-{[7-oxo-3-(2,4,6-trifluorobenzoyl)-1,7-dihydro-6H-pyrrolo[2,3-c]pyridin-6-yl]methyl}-1H-benzimidazole-5-carboxamide

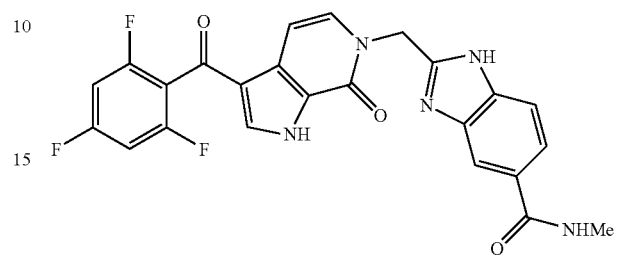

Following the procedure for example 24, the product obtained in Example 26 was treated with methylamine/ethanol instead of ethylamine to give the titled compound. LC/MS: m/z 480(M+H). $^1$H-NMR (500 MHz, d$^6$-DMSO). δ 2.78 (d, 3H), 5.55 (s, 2H), 7.04 (d, 1H), 7.35 (t, 2H), 7.58-7.62 (m, 2H), 7.75 (dd, 1H), 7.92 (d, 1H), 8.04 (s, 1H), 8.44 (d, 1H), 13.1 (d, 1H).

Example 28

3-[(2,4-difluorophenyl)(hydroxy)methyl]-6-(imidazo[1,2-a]pyridin-2-ylmethyl)-1,6-dihydro-7H-pyrrolo[2,3-c]pyridin-7-one

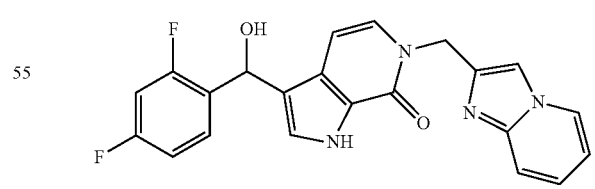

To a MeOH solution of the product obtained in Example 20 (10 mg) was added sodium boronhydride (4 mg) at room temperature. After stirring for 30 min, the mixture was diluted with MeCN/water (3/2) and purified by reverse phase HPLC (C-18 column) to give the title compound (4 mg). LC/MS: m/z 407(M+H).

Example 29

6-(1H-imidazo[4,5-b]pyridin-2-ylmethyl)-3-(2,4,6-trifluorobenzyl)-1,6-dihydro-7H-pyrrolo[2,3-c]pyridin-7-one

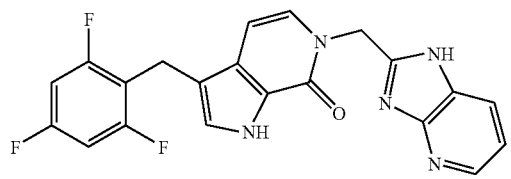

To a TFA 2.5 mL solution of the product obtained in example 6 (115 mg, 0.272 mmol) was added triethylsilane (103 mg, 0.68 mmol). After heating to 100° C. in an oil bath overnight, the reaction mixture was cooled to room temperature, diluted with 3:2 MeCN:H$_2$O (4 mL) and purified by reverse phase HPLC (C-18 column) to give the title compound (13.4 mg). LC/MS: m/z 410(M+H). $^1$H-NMR (500 MHz, d$^6$-DMSO): δ 3.91 (s, 2H), 5.46 (s, 2H), 6.51 (d, 1H), 7.06 (d, 1H), 7.15 (t, 2H), 7.34 (d, 1H), 8.04 (d, 1H), 8.38 (br.s, 1H), 11.83 (s, 1H).

Compounds 30-81 were prepared following the procedure in example 1-29 employing intermediates that are described in the examples, commercially available compounds, or compounds prepared following published procedure.

Structures of Compound 30-81 and Mass Spectrum Data

| Compound | Structure | Formula Weight | Observed m/z |
|---|---|---|---|
| 30 | 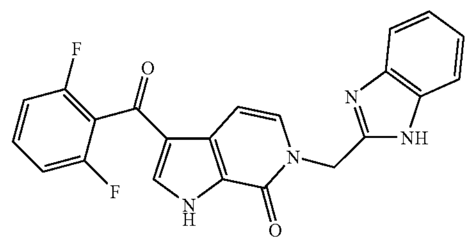 | 404.38 | 405 (M + H) |
| 31 | 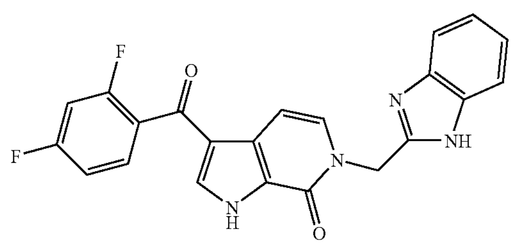 | 404.38 | 405 (M + H) |
| 32 | 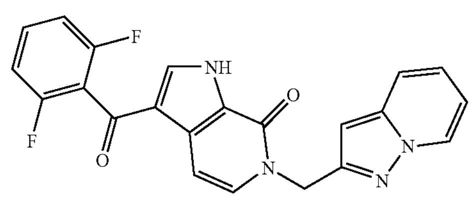 | 404.38 | 405 (M + H) |
| 33 | 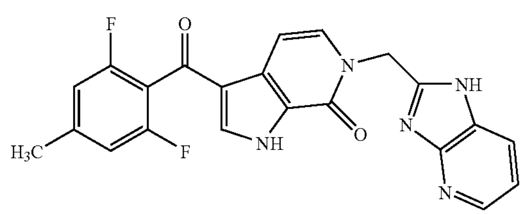 | 419.39 | 420 (M + H) |
| 34 | 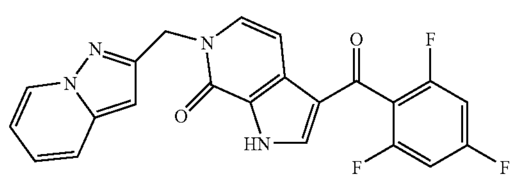 | 422.37 | 423 (M + H) |

-continued

| Compound | Structure | Formula Weight | Observed m/z |
|---|---|---|---|
| 35 | 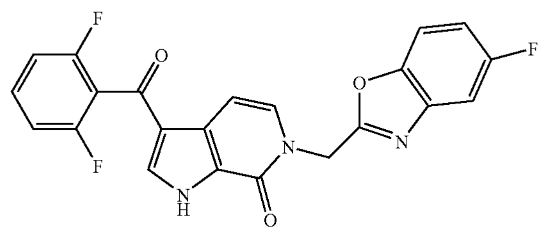 | 423.35 | 424 (M + H) |
| 36 | 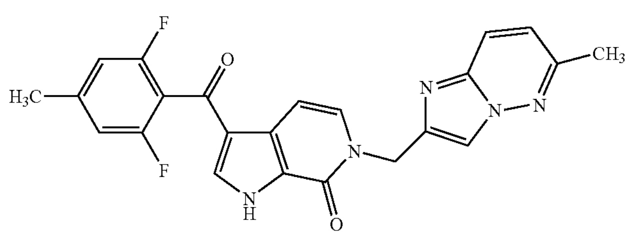 | 433.42 | 434 (M + H) |
| 37 | 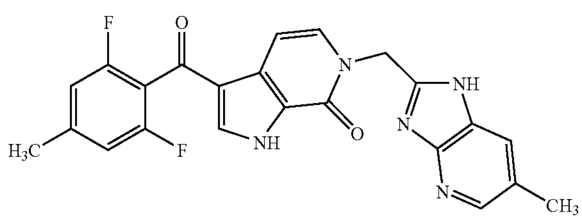 | 433.42 | 434 (M + H) |
| 38 | 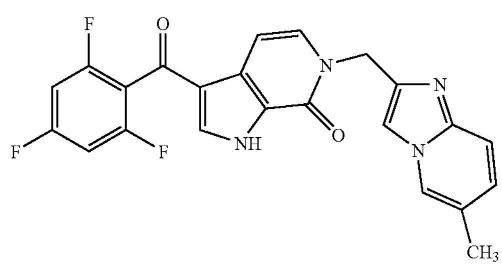 | 436.40 | 437 (M + H) |
| 39 | 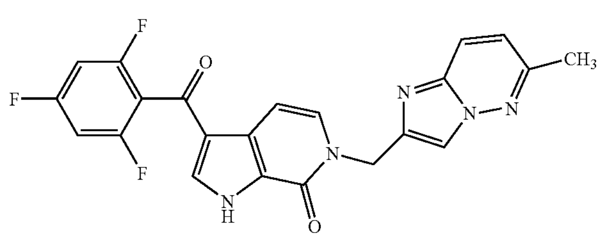 | 437.38 | 438 (M + H) |
| 40 | 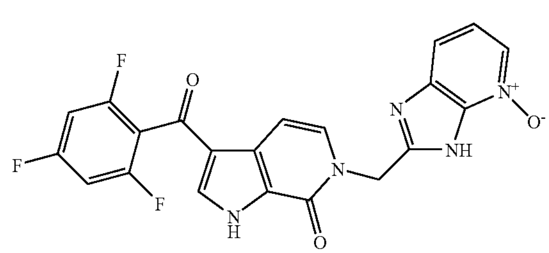 | 439.36 | 440 (M + H) |

-continued

| Compound | Structure | Formula Weight | Observed m/z |
|---|---|---|---|
| 41 | 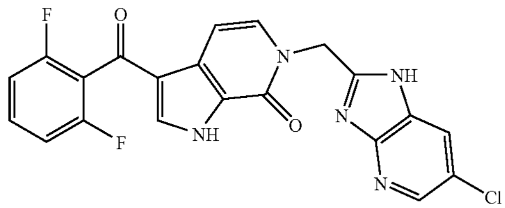 | 439.81 | 440 (M + H) |
| 42 | 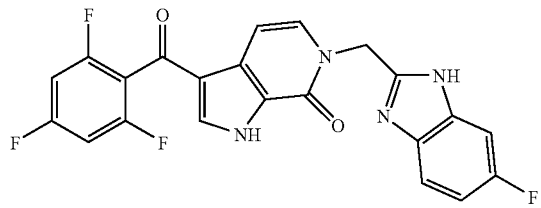 | 440.36 | 441 (M + H) |
| 43 | 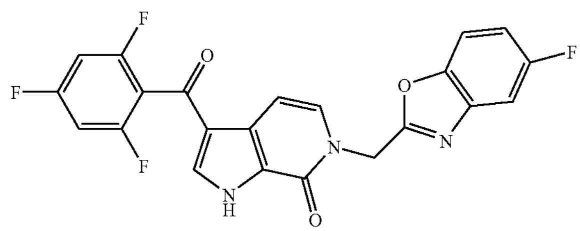 | 441.35 | 442 (M + H) |
| 44 | 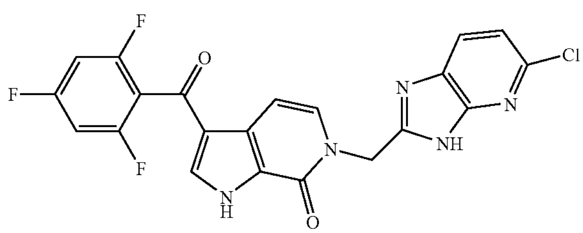 | 457.80 | 458 (M + H) |
| 45 | 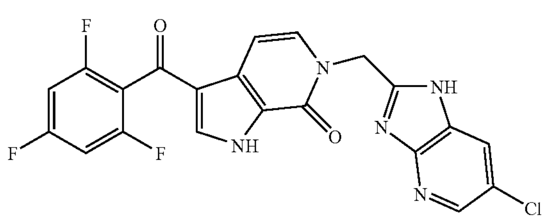 | 457.80 | 458 (M + H) |
| 46 | 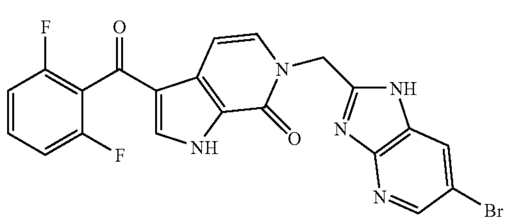 | 484.26 | 485 (M + H) |

-continued

| Compound | Structure | Formula Weight | Observed m/z |
|---|---|---|---|
| 47 | 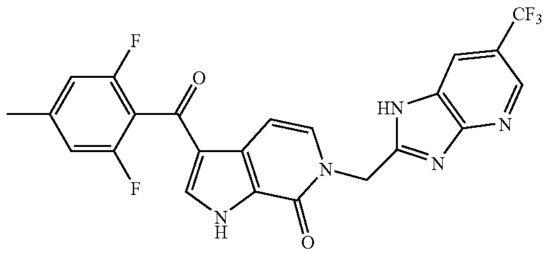 | 487.39 | 488 (M + H) |
| 48 | 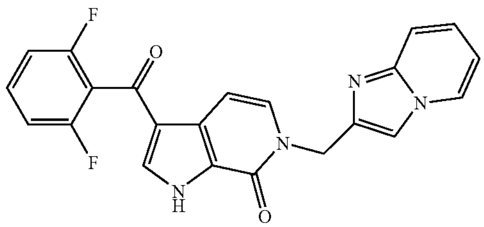 | 404.37 | 405 (M + H) |
| 49 | 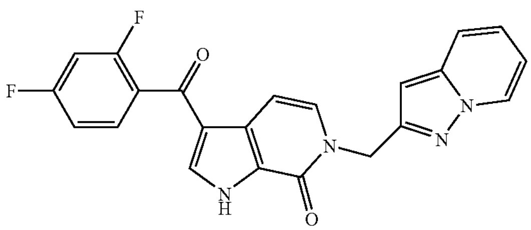 | 404.37 | 405 (M + H) |
| 50 | 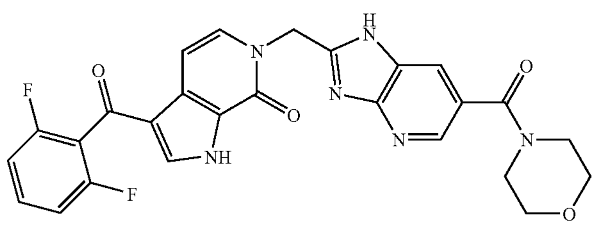 | 518.48 | 519 (M + H) |
| 51 | 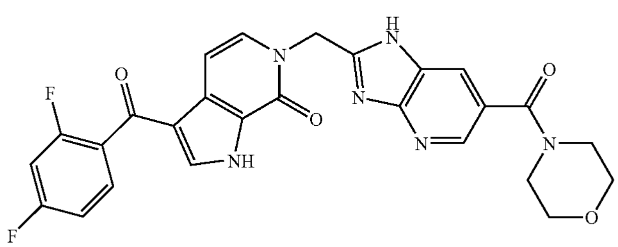 | 518.48 | 519 (M + H) |
| 52 | 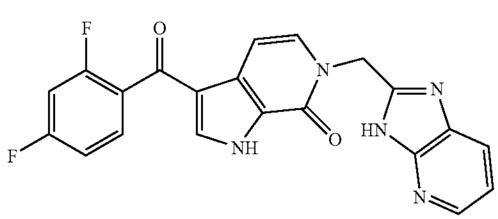 | 405.36 | 406 (M + H) |

-continued
| Compound | Structure | Formula Weight | Observed m/z |
|---|---|---|---|
| 53 | 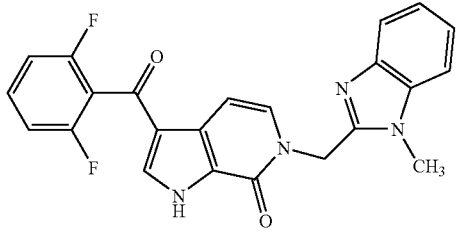 | 418.40 | 419 (M + H) |
| 54 | 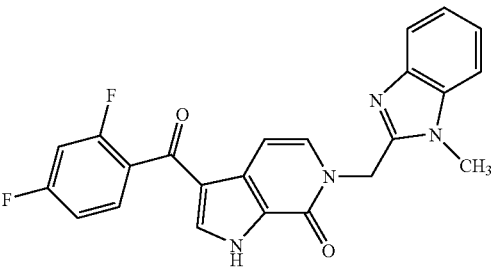 | 418.40 | 419 (M + H) |
| 55 | 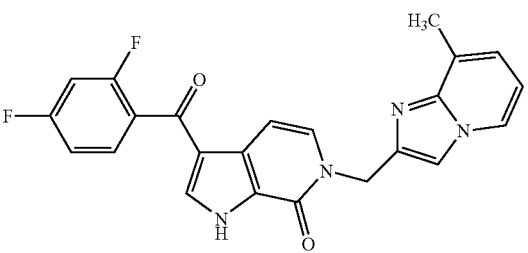 | 418.40 | 419 (M + H) |
| 56 | 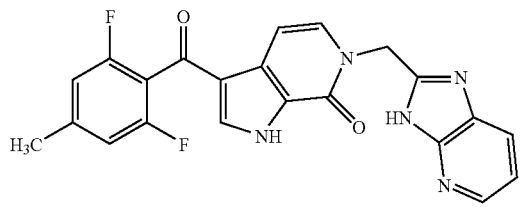 | 419.38 | 420 (M + H) |
| 57 | 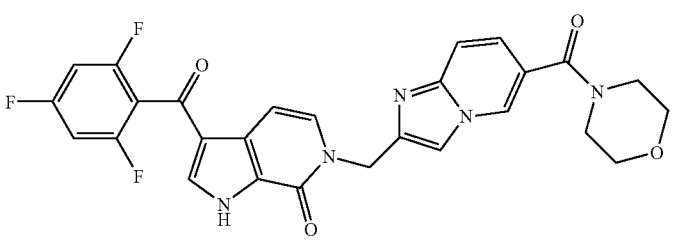 | 535.49 | 536 (M + H) |
| 58 | 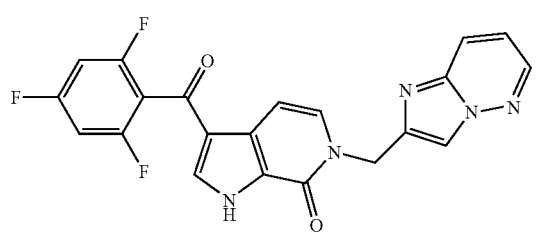 | 423.35 | 424 (M + H) |

-continued

| Compound | Structure | Formula Weight | Observed m/z |
|---|---|---|---|
| 59 | 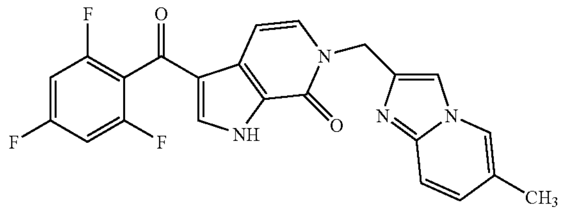 | 436.39 | 437 (M + H) |
| 60 | 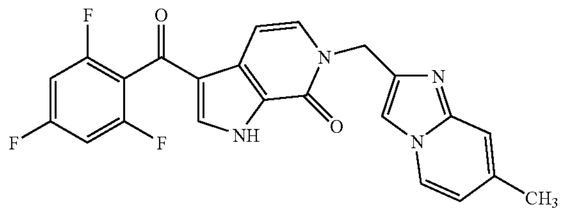 | 436.39 | 437 (M + H) |
| 61 | 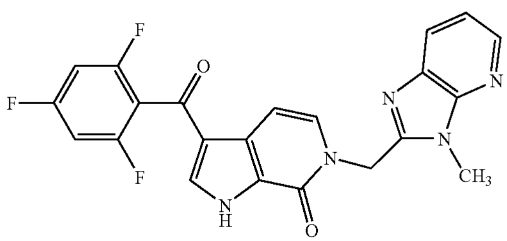 | 437.37 | 438 (M + H) |
| 62 | 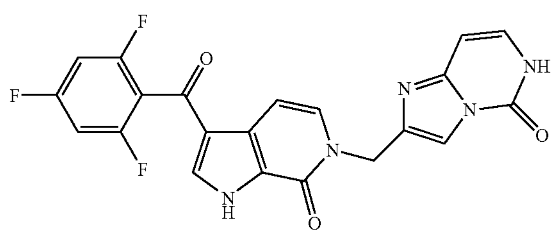 | 439.35 | 440 (M + H) |
| 63 | 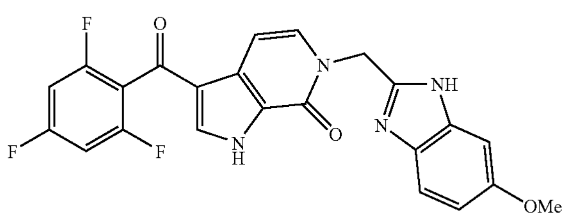 | 452.39 | 453 (M + H) |
| 64 | 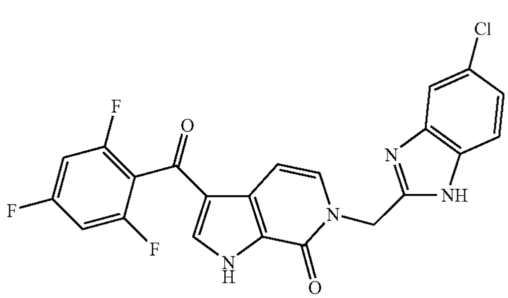 | 456.80 | 457 (M + H) |

-continued

| Compound | Structure | Formula Weight | Observed m/z |
|---|---|---|---|
| 65 | 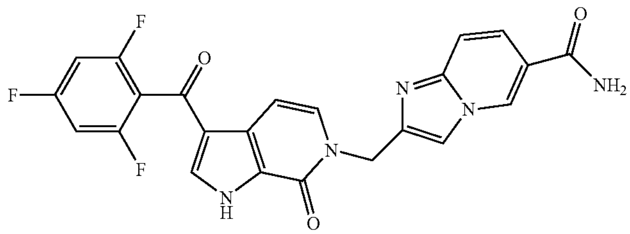 | 465.38 | 466 (M + H) |
| 66 | 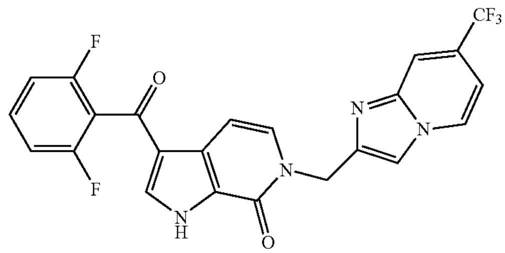 | 472.37 | 473 (M + H) |
| 67 | 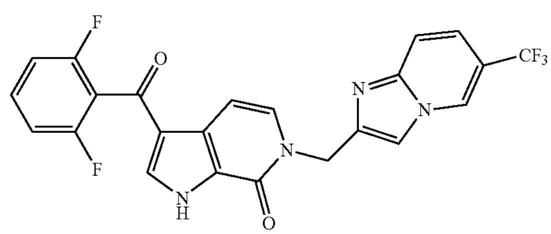 | 472.37 | 472 (M+) |
| 68 | 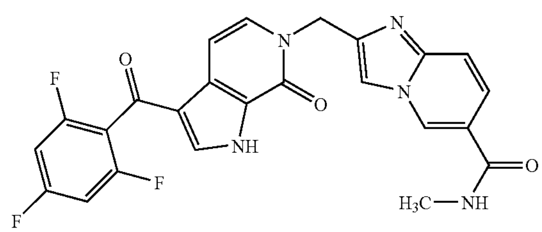 | 479.41 | 480 (M + H) |
| 69 | 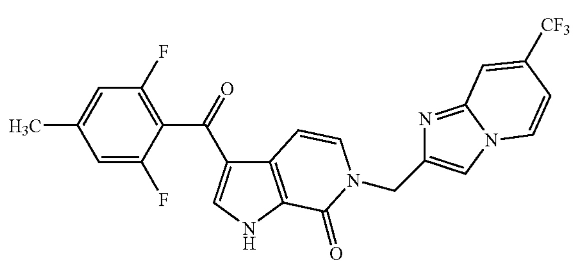 | 486.39 | 487 (M + H) |
| 70 | 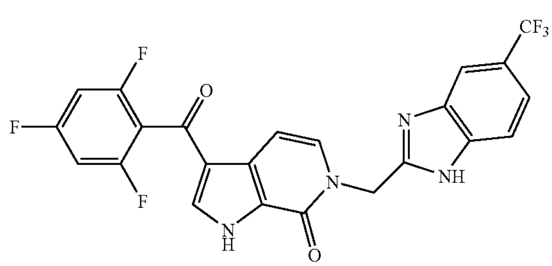 | 490.36 | 491 (M + H) |

-continued

| Compound | Structure | Formula Weight | Observed m/z |
|---|---|---|---|
| 71 | 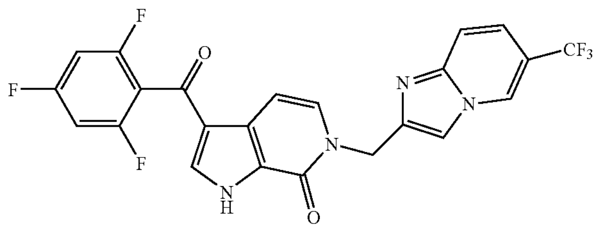 | 490.36 | 490 (M+) |
| 72 | 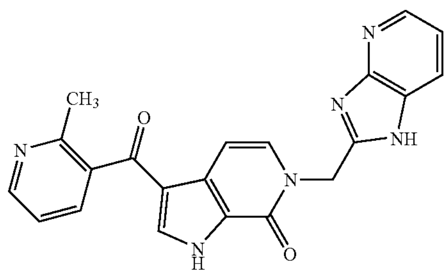 | 384.39 | 385 (M + H) |
| 73 | 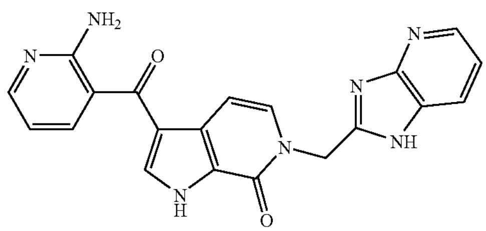 | 385.38 | 386 (M + H) |
| 74 | 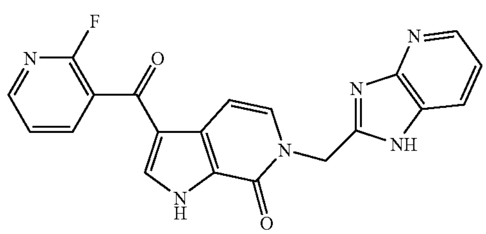 | 388.35 | 389 (M + H) |
| 75 | 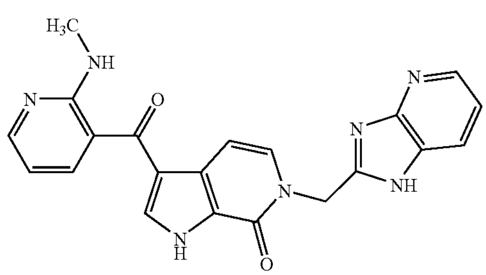 | 399.41 | 400 (M + H) |
| 76 | 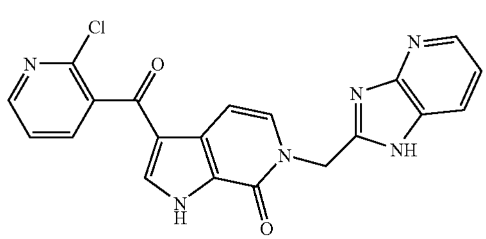 | 404.81 | 405 (M + H) |

| Compound | Structure | Formula Weight | Observed m/z |
|---|---|---|---|
| 77 | 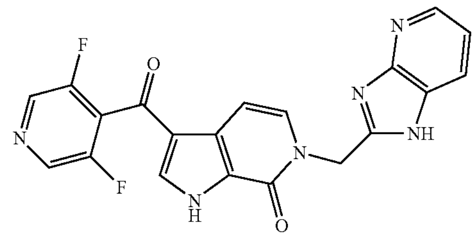 | 406.35 | 407 (M + H) |
| 78 | 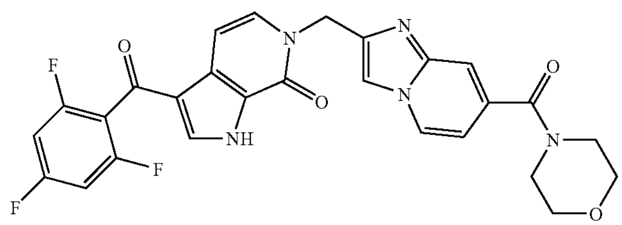 | 535.47 | 536 (M + H) |
| 79 | 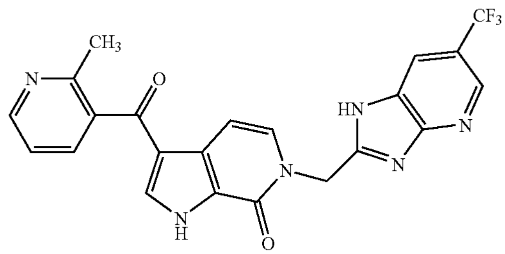 | 452.39 | 453 (M + H) |
| 80 | 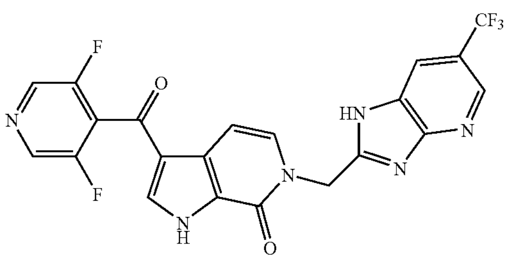 | 474.34 | 475 (M + H) |
| 81 | 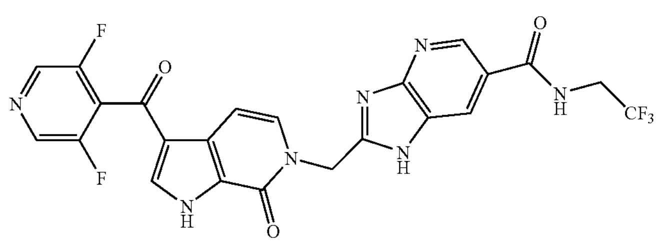 | 531.39 | 532 (M + H) |

Example 82

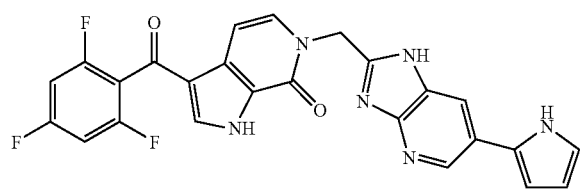

6-{[6-(1H-pyrrol-2-yl)-1H-imidazo[4,5-b]pyridin-2-yl]methyl}-3-(2,4,6-trifluorobenzoyl)-1,6-dihydro-7H-pyrrolo[2,3-c]pyridin-7-one A microwavable vial was charged with 6-[(6-bromo-1H-imidazo[4,5-b]pyridin-2-yl)methyl]-3-(2,4,6-trifluorobenzoyl)-1,6-dihydro-7H-pyrrolo[2,3-c]pyridin-7-one (20 mg, 0.04 mmol), [1-(tert-butoxycarbonyl)-1H-pyrrol-2-yl]boronic acid (12.6 mg, 0.06 mmol), cesium carbonate (39 mg, 0.119 mmol), bis(triphenylphosphine)palladium(II) chloride (2.8 mg, 3.98 umol) and acetonitril/water (0.6/0.2 ml). The vial was sealed, purged by 3 cycles of freeze-pump-thaw. The resultant suspension was heated to 135° C. by microwave irradiation for 15 min. LCMS showed complete consumption of the starting material and formation of the desired product. The reaction mixture was diluted with acetonitrile, and filtered through a 0.45 micron membrane filter and then concentrated to dryness under reduced pressure. The crude reaction mixture was purified by HPLC on Xbridge (C18 5u particle size, 30×75 mm) preparative column eluting with a linear gradient of 15-40% acetonitrile/water (0.01% NH4OH) at 70 ml/min. to give the title compound (1.6 mg, 8%). MS (ESI): m/z 489 (M+H). $^1$H-NMR (500 MHz, d$^6$-DMSO): δ 11.35 (br. s, 1H), 8.61 (s, 1H), 8.03 (s, 1H), 7.89 (s, 1H), 7.58 (d, 1H), 7.36 (m, 2H), 7.00 (d, 1H), 6.86 (s, 1H), 6.54 (s, 1H), 6.11 (s, 1H), 5.47 (s, 2H), Intermediate 20

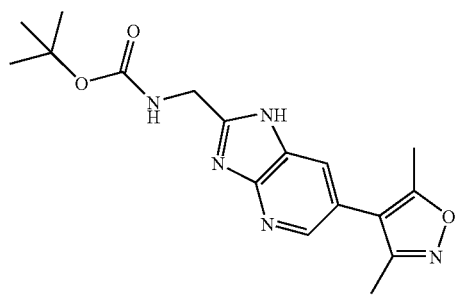

[6-(3,5-Dimethyl-isoxazol-4-yl)-1H-imidazo[4,5-b]pyridin-2-ylmethyl]-carbamic Acid tert-butyl Ester To a dry 20 mL microwave vessel equipped with a stir bar, 1,1'-bis(diphenylphosphino)ferrocene-palladium(II)dichloride dichloromethane complex (125 mg, 0.153 mmol) and LiOH (110 mg, 4.58 mmol) were combined. The vessel was capped with septa and purged three times with vacuum and nitrogen. The mixture was suspended into degassed, 10:1 dioxane: H2O (2.5 mL). To the suspension, (6-Bromo-1H-imidazo[4,5-b]pyridin-2-ylmethyl)-carbamic acid tert-butyl ester (500 mg, 1.528 mmol), 3,5-dimethylisoxazole-4-boronic acid (323 mg, 2.292 mmol) and pinacol (271 mg, 2.292 mmol) were added. The reaction mixture was purged again with vacuum and nitrogen three times and sealed using a microwave crimped septa. The reaction vessel was placed in a microwave reactor and heated at 120° C. for 2.5 hrs. The reaction was complete based on LC/MS (M+1=344). The resulting brown suspension was concentrated under reduced pressure to dryness and reconstituted with 20 mL of 10% MeOH-DCM. 30 g of 230-400 mesh SiO$_2$ was then added and the resulting slurry was stirred vigorously. Removed solvent under reduced pressure and packed compound absorbed on silica into a 40 g SIM cartridge. Purified crude using SiO2 flash chromatography (120 g ISCO cartridge; 230-400 mesh SiO$_2$) equilibrated with 10% MeOH-DCM containing 0.5% triethylamine to give 360 mg of the title compound as an amber oil (69%).

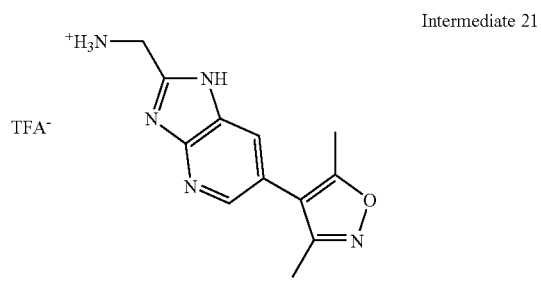

Intermediate 21

6-(3,5-Dimethyl-isoxazol-4-yl)-1H-imidazo[4,5-b]pyridin-2-ylmethyl-ammonium Trifluoroacetic Acid Salt To a DCM solution (4 mL) of [6-(3,5-Dimethyl-isoxazol-4-yl)-1H-imidazo[4,5-b]pyridin-2-ylmethyl]-carbamic acid tert-butyl ester (360 mg, 1.048 mmol) was added trifluoroacetic acid (4.0 mL, 51.9 mmol), in a nitrogen atmosphere.

The reaction was stirred for 1 hr. at room temperature and was determined to be complete based on LC/MS (M+1=244). Removed solvent under reduced pressure and reconstituted in 40% aq. MeCN. Purified mixture via RP C-18 HPLC (30× 100 mm column, 5μ particle size) using gradient conditions; 5-50% MeCN—H$_2$O containing 0.5% TFA. lyophilization afforded 205 mg of the title compound as a white solid (54%)

FURTHER EXAMPLES

Examples 83 through 89 in Table I can be prepared following the procedure of Additional Example 82 using appropriate Ar$^1$ and boronic acid. Examples 90 through 94 in Table 1 can be prepared following the procedure of Examples 82, step A, B and C using appropriate Ar$^1$ and boronic acid.

TABLE I

| Example | Ar1 | Het |
|---|---|---|
| 83 | 2,4,6-trifluorophenyl | 3,5-dimethylisoxazol-4-yl |
| 84 | 2,4,6-trifluorophenyl | 1H-pyrrol-3-yl |

TABLE I-continued (structure with Ar1—C(=O)— attached to pyrrolopyridinone with N-CH2-imidazo[4,5-b]pyridine-Het)

| Example | Ar1 | Het |
|---|---|---|
| 85 | 2,4,6-trifluorophenyl | pyrrole N-Si(tBu)2Bu(t) |
| 86 | 2,4,6-trifluorophenyl | 1H-pyrazol-3-yl |
| 87 | 2,4,6-trifluorophenyl | 1-methylpyrazol-3-yl |
| 88 | 2,4,6-trifluorophenyl | 3,5-dimethyl-1H-pyrazol-4-yl |
| 89 | 2,6-difluoro-4-methylphenyl | 3,5-dimethylisoxazol-4-yl |
| 90 | 2,6-difluorophenyl | 3,5-dimethylisoxazol-4-yl |
| 91 | 2,6-difluoro-4-methylphenyl | 3,5-dimethyl-1H-pyrazol-4-yl |

TABLE I-continued (structure with Ar1—C(=O)— attached to pyrrolopyridinone isomer with N-CH2-imidazo[4,5-b]pyridine-Het)

| Example | Ar1 | Het |
|---|---|---|
| 92 | 2,6-difluorophenyl | 1H-pyrazol-4-yl |
| 93 | 2,6-difluoro-4-methylphenyl | 1H-pyrazol-4-yl |
| 94 | 2,6-difluorophenyl | 1H-pyrazol-3-yl |

Example 83

6-{[6-(3,5-dimethylisoxazol-4-yl)-1H-imidazo[4,5-b]pyridin-2-yl]methyl}-3-(2,4,6-trifluorobenzoyl)-1,6-dihydro-7H-pyrrolo[2,3-c]pyridin-7-one $^1$H NMR (d$^4$-CD3OD, 500 Mhz) δ 8.28 (m, 1H), 7.89 (m, 1H), 7.77 (s, 1H), 7.56 (d, 2H, J=2.7 Hz), 7.26 (d, 1H, J=3.7 Hz), 7.05 (m, 2H), 5.60 (S, 2H), 3.65 (S, 1H), 3.35 (S, 1H), 2.42 (S, 3H), 2.25 (S, 3H).
LC/MS; M+1=518.

Example 84

6-{[6-(1H-pyrrol-3-yl)-1H-imidazo[4,5-b]pyridin-2-yl]methyl}-3-(2,4,6-trifluorobenzoyl)-1,6-dihydro-7H-pyrrolo[2,3-c]pyridin-7-one $^1$H NMR (d$^6$-DMSO, 500 Mhz) δ 8.57 (s, 1/2H), 8.49 (s, 1/2H), 7.90 (m, 2H), 7.59 (m, 2H), 7.36 (m, 3H), 7.00 (t, 1H, J=8.5 Hz), 6.79 (m, 1H), 6.48 (d, 1H, J=8.1 Hz), 5.47 (m, 3H).
LC/MS; M+1=489.

Example 85

6-[(6-methyl-1H-imidazo[4,5-b]pyridin-2-yl)methyl]-3-(2,4,6-trifluorobenzoyl)-1,6-dihydro-7H-pyrrolo[2,3-c]pyridin-7-one $^1$H NMR (d$^6$-DMSO, 500 Mhz) δ 13.15 (bs, 1H), 8.63 (m, 1/2H), 8.07 (m, 1/2H), 7.90 (m, 1H), 7.55 (m, 1H), 7.37 (m, 3H), 7.01-6.67 (m, 3H), 6.19 (S, 1H), 5.47 (S, 2H), 1.06-1.01 (m, 17H)
LC/MS; M+1=646.

Example 86

6-{[6-(1H-pyrrol-3-yl)-1H-imidazo[4,5-b]pyridin-2-yl]methyl}-3-(2,4,6-trifluorobenzoyl)-1,6-dihydro-7H-pyrrolo[2,3-c]pyridin-7-one $^1$H NMR (d$^6$-DMSO, 500 Mhz) δ 13.10 (m, 2H), 8.64 (s, 1/2H), 8.56 (s, 1/2H), 8.14 (s, 1/2H), 7.96 (s, 1/2H), 7.90 (s, 1H), 7.37 (m, 2H), 7.20 (m, 1H), 7.01 (m, 1H), 5.47 (m, 2H).
LC/MS; M+1=490.

Example 87

6-{[6-(1-methyl-1H-pyrazol-3-yl)-1H-imidazo[4,5-b]pyridin-2-yl]methyl}-3-(2,4,6-trifluorobenzoyl)-1,6-dihydro-7H-pyrrolo[2,3-c]pyridin-7-one $^1$H NMR(d$^6$-DMSO, 500 Mhz) δ 8.58 (s, 1/2H), 8.51 (s, 1/2H), 8.21-7.90 (m, 3H), 7.60 (m, 1H), 7.37 (m, 3H), 7.01 (m, 1H), 5.48 (s, 2H), 3.85 (S, 3H).
LC/MS; M+1=504.

Example 88

6-{[6-(3,5-dimethyl-1H-pyrazol-4-yl)-1H-imidazo[4,5-b]pyridin-2-yl]methyl}-3-(2,4,6-trifluorobenzoyl)-1,6-dihydro-7H-pyrrolo[2,3-c]pyridin-7-one $^1$H NMR (d$^6$-DMSO, 500 Mhz) δ 8.28 (s, 1H), 8.19 (s, 1H), 7.90 (s, 1H), 7.45 (m, 1H), 7.37 (m, 2H), 7.26 (m, 1H), 7.01 (m, 1H), 5.50 (S, 2H), 2.174 (S, 3H), 2.165 (S, 3H).
LC/MS; M+1=518.

Example 89

3-(2,6-Difluoro-4-methyl-benzoyl)-6-[6-(3,5-dimethyl-isoxazol-4-yl)-3-H-imidazo[4,5-b]pyridin-2-ylmethyl]-1,6-dihydro-pyrrolo[2,3-c]pyridin-7-one $^1$H NMR (500 Mhz, d$^6$-DMSO) δ: 13.10 (s, 1H), 8.33 (s, 1H), 7.99 (d, 1H), 7.76 (d, 1H), 7.58 (d, 1H), 7.06 (d, 1H), 6.97 (d, 1H), 5.53 (s, 2H), 2.39 (br.s, 6H), 2.20 (s, 3H).
LC/MS; M+1=515.

Example 90

3-(2,6-Difluoro-benzoyl)-6-[6-(3,5-dimethyl-isoxazol-4-yl)-3-H-imidazo[4,5-b]pyridin-2-ylmethyl]-1,6-dihydro-pyrrolo[2,3-c]pyridin-7-one $^1$H NMR (d$^6$-DMSO, 500 Mhz) δ: 13.10 (s, 1H), 8.34 (s, 1H), 7.99 (s, 1H), 7.78 (d, 1H), 7.58-7.64 (m, 2H), 7.26 (t, 2H), 6.98 (d, 1H), 5.53 (s, 2H), 2.39 (s, 3H), 2.21 (s, 3H).
LC/MS; M+1=501.

Example 91

3-(2,6-Difluoro-4-methyl-benzoyl)-6-[6-(3,5-dimethyl-1H-pyrazol-4-yl)-3H-imidazo[4,5-b]pyridin-2-ylmethyl]-1,6-dihydro-pyrrolo[2,3-c]pyridin-7-one $^1$H NMR (d$^4$-CD3OD, 500 Mhz) δ: 8.49 (br.s, 1H), 8.19 (br.s, 1H), 7.70 (s, 1H), 7.58 (d, 1H), 7.26 (d, 2H), 5.60 (s, 2H), 2.45 (s, 3H), 2.31 (s, 6H)
LC/MS; M+1=514. .

Example 92

3-(2,6-Difluoro-benzoyl)-6-[6-(1H-pyrazol-4-yl)-3H-imidazo[4,5-b]pyridin-2-ylmethyl]-1,6-dihydro-pyrrolo[2,3-c]pyridin-7-one $^1$H NMR (d$^4$-CD3OD, 500 Mhz) δ: 8.70 (br.s, 1H), 8.51 (br.s, 1H), 8.48 (br.s, 2H), 7.70 (s, 1H), 7.55-7.61 (m, 2H), 7.27 (d, 1H), 7.13 (t, 2H), 5.67 (bs, 2H).
LC/MS; M+1=472.

Example 93

3-(2,6-Difluoro-4-methyl-benzoyl)-6-[6-(1-H-pyrazol-4-yl)-3-H-imidazo[4,5-b]pyridin-2-ylmethyl]-1,6-dihydro-pyrrolo[2,3-c]pyridin-7-one $^1$H NMR (500 Mhz, d$^4$-CD$_3$OD) δ: 8.77 (br.s, 1H), 8.39 (br.s, 1H), 8.17 (br. S, 2H), 7.64 (s, 1H), 7.56 (d, 1H), 7.18 (d, 1H), 6.96 (d, 2H), 5.66 (br.s, 2H), 2.44 (s, 3H).
LC/MS; M+1=486.

Example 94

3-(2,6-Difluoro-benzoyl)-6-[6-(1H-pyrazol-3-yl)-3H-imidazo[4,5-b]pyridin-2-ylmethyl]-1,6-dihydro-pyrrolo[2,3-c]pyridin-7-one $^1$H NMR (500 Mhz, d$^6$-DMSO) δ: 13.10 (s, 1H), 8.78 (s, 1H), 8.23 (s, 1H), 7.78 (d, 1H), 7.74 (br.s, 1H), 7.59-7.63 (m, 2H), 7.24 (t, 2H), 6.97 (d, 1H), 6.78 (d, 1H), 5.50 (s, 2H).
LC/MS; M+1=472.

What is claimed is:
1. A compound represented by chemical formula (A)

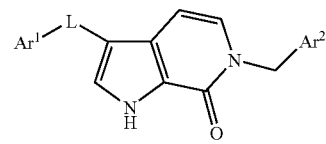

(A)

or a pharmaceutically acceptable salt thereof, wherein:
L is selected from the group consisting of:
 (a) —C(O)—,
 (b) —CH(OH)—,
 (c) —CH(NR$^3$R$^4$)—,
 (d) —C(=NOR$^3$)—,
 (e) —CH$_2$—, and
 (f) —S(O)$_n$—, wherein n is 0, 1 or 2;
Ar$^1$ is an optionally mono, di- or tri-substituted aromatic or heteroaromatic ring of 6 atoms, wherein the heteroaromatic ring may contain 1, 2 or 3 heteroatoms selected from N, S and O, wherein the substituents are independently selected from the group consisting of:
 (a) halo,
 (b) —C$_{1-4}$alkyl,
 (c) —O—C$_{1-4}$alkyl,
 (d) —CF$_3$,
 (e) —NH$_2$,
 (f) —NH—CH$_3$,
 (g) —CN,
 (h) —C(O)NH$_2$, and
 (i) —S(O)$_n$—CH$_3$;

Ar² is an optionally mono, di- or tri-substituted fused 5,6 bi-cyclic heterocyclic ring selected from the group consisting of

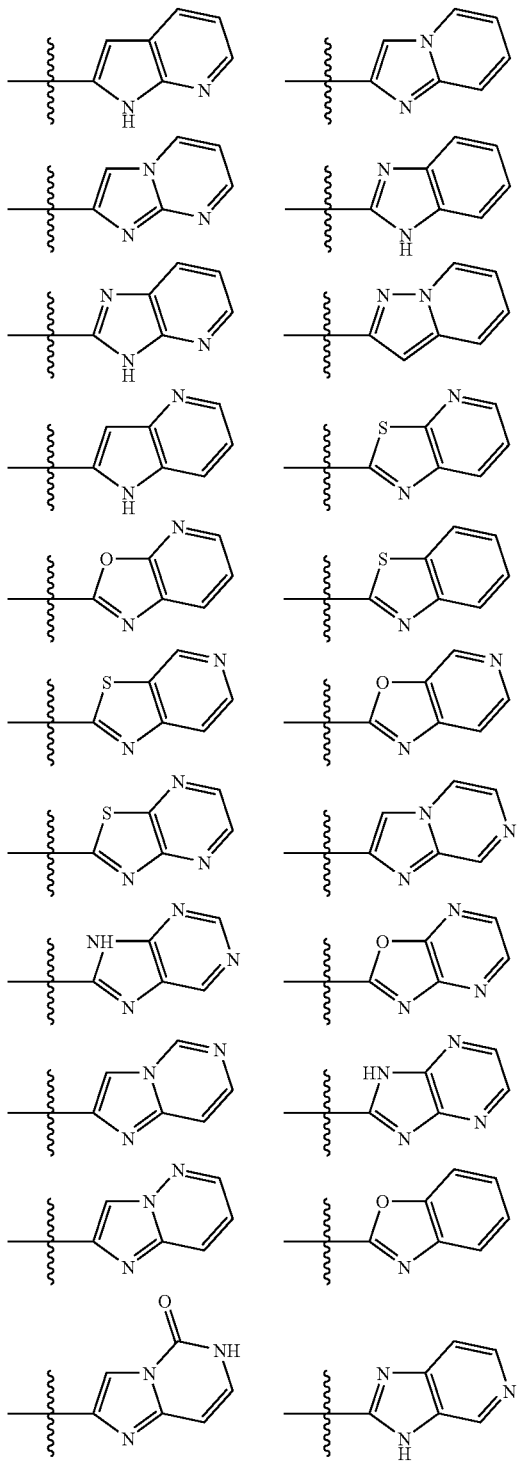

or N-oxide thereof, wherein the substituents are independently selected from the group consisting of
(a) halo,
(b) —C₁₋₄alkyl,
(c) —O—C₁₋₄alkyl,
(d) —CF₃,
(e) —NH₂, and
(f) —NH₂—CH₃,
(g) —NH₂—CH₂CF₃,
(h) —C(O)-morpholinyl,
(i) —C(O)—NR¹R²,
(j) —C(O)OH,
(k) —CN,
(l) a 5 or 6 membered heteroaromatic or heterocyclic ring containing 1, 2 or 3 hetero atoms selected from the group consisting of S, O and N;
R¹, R², R³ and R⁴ are independently selected from the group consisting of
(a) hydrogen, and
(b) C₁₋₄alkyl,
or R¹ and R² or R³ and R⁴ may be joined together to form a 5 or 6 membered saturated ring, said ring optionally containing a heteroatom selected from S, N and O.

2. The compound according to claim 1, wherein
L is selected from the group consisting of:
(a) —C(O)—, and
(b) —CH₂—.

3. The compound according to claim 2, wherein
L is —C(O)—.

4. The compound according to claim 1, wherein
Ar¹ is an optionally mono, di- or tri-substituted aromatic or heteroaromatic ring of 6 atoms, wherein the heteroaromatic ring may contain 1, 2 or 3 heteroatoms selected from N, S and O, wherein the substituents are independently selected from the group consisting of:
(a) halo,
(b) —C₁₋₄alkyl, and
(c) —O—C₁₋₄alkyl.

5. The compound according to claim 4, wherein
Ar¹ is an optionally mono, di- or tri-substituted phenyl or pyridyl, wherein the substituents are independently selected from the group consisting of
(a) fluoro,
(b) chloro, and
(c) —CH₃.

6. The compound according to claim 1 wherein in choice (1) of Ar², the 5 or 6 membered heteroaromatic or heterocyclic ring containing 1, 2 or 3 hetero atoms selected from the group consisting of S, O and N is selected from the group consisting of:
(a) pyridinyl,
(b) pyridazinyl,
(c) pyrimidinyl,
(d) pyrazinyl,
(e) thiazolyl,
(f) thiophenyl,
(g) pyrrolyl,
(h) oxazolyl,
(i) pyrrolidinyl,
(j) piperidinyl,
(k) piperazinyl, and
(l) morpholinyl.

7. The compound according to claim 1 wherein
Ar² is an optionally mono, di- or tri-substituted fused 5,6 bi-cyclic heterocyclic ring selected from the group consisting of:

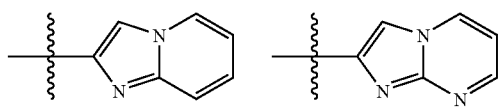

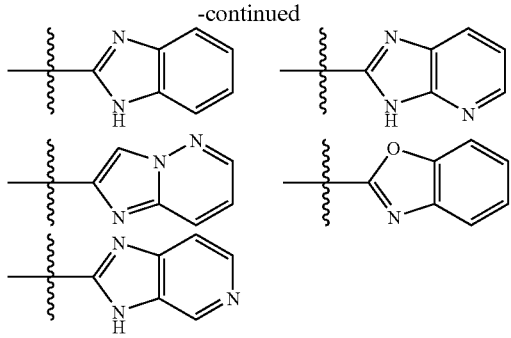

or N-oxide thereof wherein the substituents are independently selected from the group consisting of:
(a) halo,
(b) —$C_{1-4}$alkyl,
(c) —O—$C_{1-4}$alkyl,
(d) —$CF_3$,
(e) —C(O)-morpholinyl,
(f) —C(O)—$NR^1R^2$, and
(g) —C(O)OH.

8. The compound according to claim 7 wherein $A^2$ is an optionally mono, di- or tri-substituted fused 5,6 bi-cyclic heterocyclic ring selected from the group consisting of:

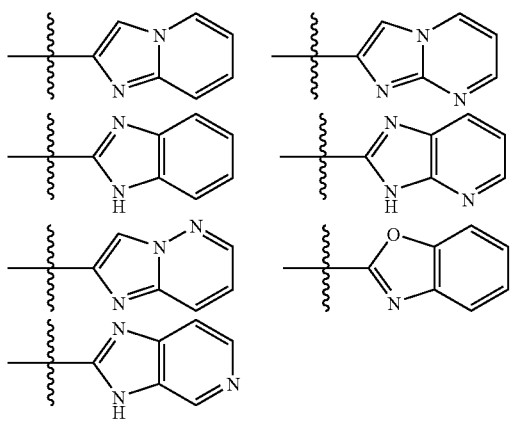

or N-oxide thereof, wherein the substituents are independently selected from the group consisting of:
(a) halo,
(b) —$CH_3$,
(c) —O—$CH_3$, and
(d) —$CF_3$.

9. The compound according to claim 1 wherein $R^1$, $R^2$, $R^3$ and $R^4$ are independently selected from the group consisting of
(a) hydrogen, and
(b) methyl, or $R^1$ and $R^2$ or $R^3$ and $R^4$ may be joined together to from a 5 or 6 membered saturated ring, said ring optionally containing a heteroatom selected from S, N and O.

10. A compound according to claim 1 of Formula I

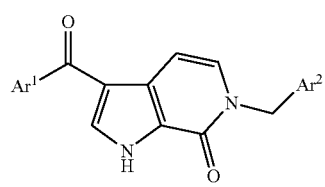

(I)

or a pharmaceutically acceptable salt thereof, wherein:

$Ar^1$ is an optionally mono, di- or tri-substituted aromatic or heteroaromatic ring of 6 atoms, wherein the heteroaromatic ring may contain 1, 2 or 3 heteroatoms selected from N, S and O, wherein the substituents are independently selected from the group consisting of:
(a) halo,
(b) —$C_{1-4}$alkyl, and
(c) —O—$C_{1-4}$alkyl;

$A^2$ is an optionally mono, di- or tri-substituted fused 5,6 bi-cyclic heterocyclic ring selected from the group consisting of

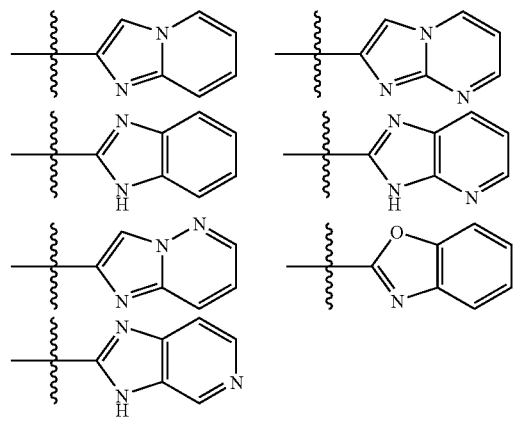

or N-oxide thereof, wherein the substituents are independently selected from the group consisting of
(a) halo,
(b) —$C_{1-4}$alkyl,
(c) —O—$C_{1-4}$alkyl,
(d) —$CF_3$,
(e) —C(O)-morpholinyl,
(f) —C(O)—$NR^1R^2$, and
(g) —C(O)OH; and $R^1$ and $R^2$ are independently selected from the group consisting of
(a) hydrogen, and
(b) $C_{1-4}$alkyl, or $R^1$ and $R^2$ may be joined together to from a 5 or 6 membered saturated ring, said ring optionally containing a heteroatom selected from S, N and O.

11. A compound according to claim 10 wherein $Ar^1$ is an optionally mono, di- or tri-substituted phenyl or pyridyl, wherein the substituents are independently selected from the group consisting of
(a) fluoro
(b) chloro, and
(c) —$CH_3$;

Ar² is an optionally mono, di- or tri-substituted fused 5,6 bi-cyclic heterocyclic ring selected from the group consisting of:

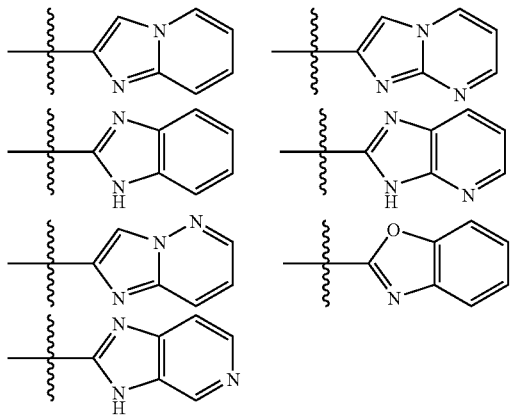

or N-oxide thereof, wherein the substituents are independently selected from the group consisting of
(a) halo,
(b) —CH₃,
(c) —O—CH₃,
(d) —C(O)—NR¹R², and
(e) —CF₃, and R¹ and R² are independently selected from the group consisting of
(a) hydrogen, and
(b) methyl,
or R¹ and R² may be joined together to from a 5 or 6 membered saturated ring, said ring optionally containing a heteroatom selected from S, N and O.

12. The compound according to claim 1, selected from the group consisting of:

6-(1H-benzimidazol-2-ylmethyl)-3-(2,4,6-trifluorobenzoyl)-1,6-dihydro-7H-pyrrolo[2,3-c]pyridin-7-one 6-[(4-fluoro-1H-benzimidazol-2-yl)methyl]-3-(2,4,6-trifluorobenzoyl)-1,6-dihydro-7H-pyrrolo[2,3-c]pyridin-7-one, 6-[(4,5-difluoro-1H-benzimidazol-2-yl)methyl]-3-(2,4,6-trifluorobenzoyl)-1,6-dihydro-7H-pyrrolo[2,3-c]pyridin-7-one, methyl 2-{[7-oxo-3-(2,4,6-trifluorobenzoyl)-1,7-dihydro-6H-pyrrolo[2,3-c]pyridin-6-yl]methyl}-1H-benzimidazole-6-carboxylate, 6-(imidazo[1,2-a]pyrimidin-2-ylmethyl)-3-(2,4,6-trifluorobenzoyl)-1,6-dihydro-7H-pyrrolo[2,3-c]pyridin-7-one, 6-(3H-imidazo[4,5-b]pyridin-2-ylmethyl)-3-(2,4,6-trifluorobenzoyl)-1,6-dihydro-7H-pyrrolo[2,3-c]pyridin-7-one, 3-(2,6-difluorobenzoyl)-6-(3H-imidazo[4,5-b]pyridin-2-ylmethyl)-1,6-dihydro-7H-pyrrolo[2,3-c]pyridin-7-one, 6-[(6-bromo-3H-imidazo[4,5-b]pyridin-2-yl)methyl]-3-(2,4,6-trifluorobenzoyl)-1,6-dihydro-7H-pyrrolo[2,3-c]pyridin-7-one, 3-(2,6-difluorobenzoyl)-6-[(6-methylimidazo[1,2-b]pyridazin-2-yl)methyl]-1,6-dihydro-7H-pyrrolo[2,3-c]pyridin-7-one, 6-(1,3-benzoxazol-2-ylmethyl)-3-(2,4,6-trifluorobenzoyl)-1,6-dihydro-7H-pyrrolo[2,3-c]pyridin-7-one, 6-[(6-methyl-3H-imidazo[4,5-b]pyridin-2-yl)methyl]-3-(2,4,6-trifluorobenzoyl)-1,6-dihydro-7H-pyrrolo[2,3-c]pyridin-7-one, 3-(2,6-difluorobenzoyl)-6-[(6-methyl-3H-imidazo[4,5-b]pyridin-2-yl)methyl]-1,6-dihydro-7H-pyrrolo[2,3-c]pyridin-7-one, 3-(3,5-difluoroisonicotinoyl)-6-(pyrazolo[1,5-a]pyridin-2-ylmethyl)-1,6-dihydro-7H-pyrrolo[2,3-c]pyridin-7-one, 3-(2,6-difluoro-4-methylbenzoyl)-6-(pyrazolo[1,5-a]pyridin-2-ylmethyl)-1,6-dihydro-7H-pyrrolo[2,3-c]pyridin-7-one, 2-{[7-oxo-3-(2,4,6-trifluorobenzoyl)-1,7-dihydro-6H-pyrrolo[2,3-c]pyridin-6-yl]methyl}-N-(2,2,2-trifluoroethyl)-3H-imidazo[4,5-b]pyridine-6-carboxamide, 6-{[6-(morpholin-4-ylcarbonyl)-1H-imidazo[4,5-b]pyridin-2-yl]methyl}-3-(2,4,6-trifluorobenzoyl)-1,6-dihydro-7H-pyrrolo[2,3-c]pyridin-7-one, 6-(3H-imidazo[4,5-c]pyridin-2-ylmethyl)-3-(2,4,6-trifluorobenzoyl)-1,6-dihydro-7H-pyrrolo[2,3-c]pyridin-7-one, 3-(2,4,6-trifluorobenzoyl)-6-{[(7-trifluoromethyl)imidazo[1,2-a]pyridin-2-yl]methyl}-1,6-dihydro-7H-pyrrolo[2,3-c]pyridin-7-one, 3-(2,4,6-trifluorobenzoyl)-6-{[6-(trifluoromethyl)-3H-imidazo[4,5-b]pyridin-2-yl]methyl}-1,6-dihydro-7H-pyrrolo[2,3-c]pyridin-7-one, 3-(2,4-difluorobenzoyl)-6-(imidazo[1,2-a]pyridin-2-ylmethyl)-1,6-dihydro-7H-pyrrolo[2,3-c]pyridin-7-one, 3-(2,6-difluorobenzoyl)-6-{[6-(trifluoromethyl)-3H-imidazo[4,5-b]pyridin-2-yl]methyl}-1,6-dihydro-7H-pyrrolo[2,3-c]pyridin-7-one, 2-{[7-oxo-3-(2,4,6-trifluorobenzoyl)-1,7-dihydro-6H-pyrrolo[2,3-c]pyridin-6-yl]methyl}imidazo[1,2-a]pyridine-7-carboxamide, 2-{[7-oxo-3-(2,4,6-trifluorobenzoyl)-1,7-dihydro-6H-pyrrolo[2,3-c]pyridin-6-yl]methyl}imidazo[1,2-a]pyridine-7-carboxylic acid, N,N-dimethyl-2-{[7-oxo-3-(2,4,6-trifluorobenzoyl)-1,7-dihydro-6H-pyrrolo[2,3-c]pyridin-6-yl]methyl}imidazo[1,2-a]pyridine-7-carboxamide, N-methyl-2-{[7-oxo-3-(2,4,6-trifluorobenzoyl)-1,7-dihydro-6H-pyrrolo-[2,3-c]pyridin-6-yl]methyl}-imidazo[1,2-a]pyridine-7-carboxamide, 2-{[7-oxo-3-(2,4,6-trifluorobenzoyl)-1,7-dihydro-6H-pyrrolo[2,3-c]pyridin-6-yl]methyl}-1H-benzimidazole-5-carboxylic acid, N-methyl-2-{[7-oxo-3-(2,4,6-trifluorobenzoyl)-1,7-dihydro-6H-pyrrolo[2,3-c]pyridin-6-yl]methyl}-1H-benzimidazole-5-carboxamide, 3-[(2,4-difluorophenyl)(hydroxy)methyl]-6-(imidazo[1,2-a]pyridin-2-ylmethyl)-1,6-dihydro-7H-pyrrolo[2,3-c]pyridin-7-one, and 6-(1H-imidazo[4,5-b]pyridin-2-ylmethyl)-3-(2,4,6-trifluorobenzyl)-1,6-dihydro-7H-pyrrolo[2,3-c]pyridin-7-one, or a pharmaceutically acceptable salt thereof.

13. The compound according to claim 1, selected from the group consisting of:
| Structure |
|---|
| 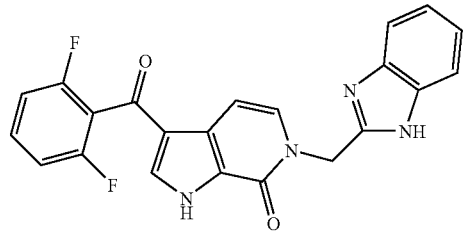 |
| 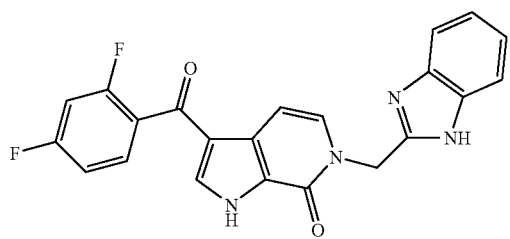 |
|  |
| 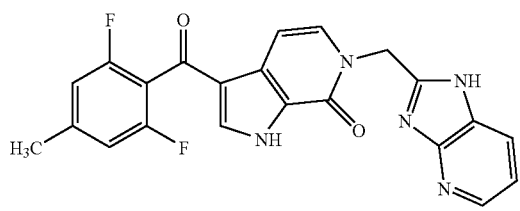 |
| 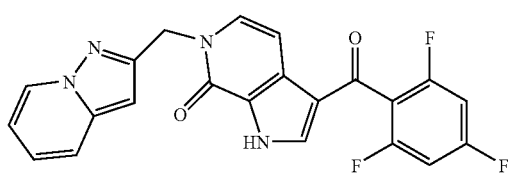 |
| 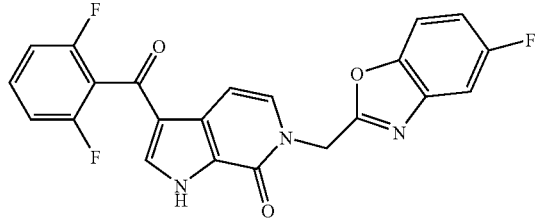 |
| 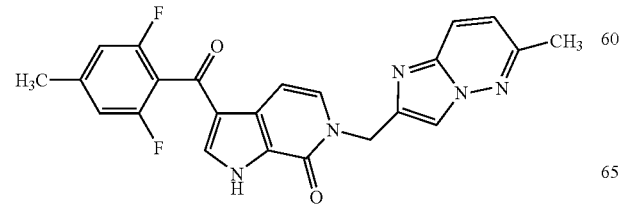 |
-continued
| Structure |
|---|
| 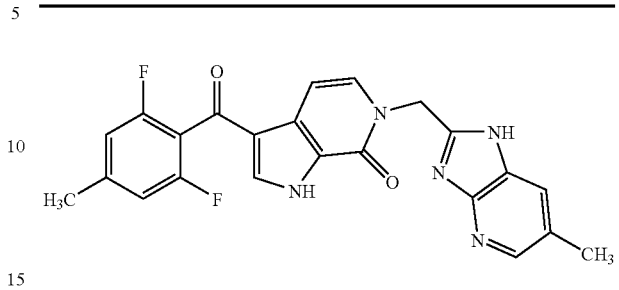 |
| 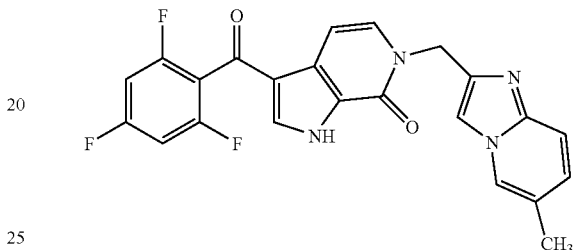 |
| 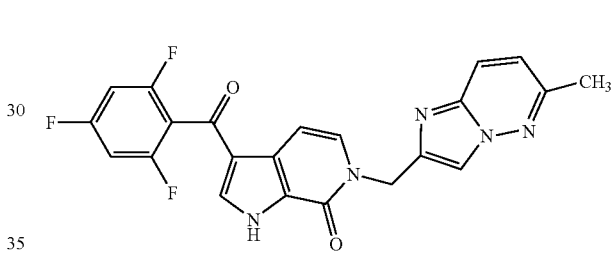 |
| 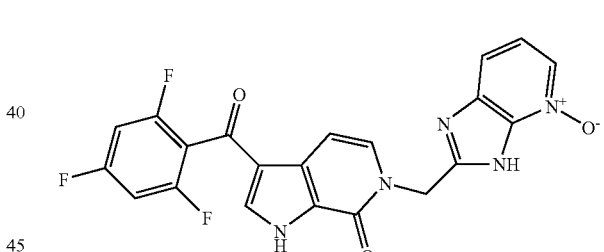 |
| 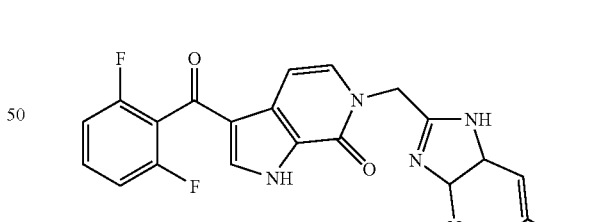 |
| 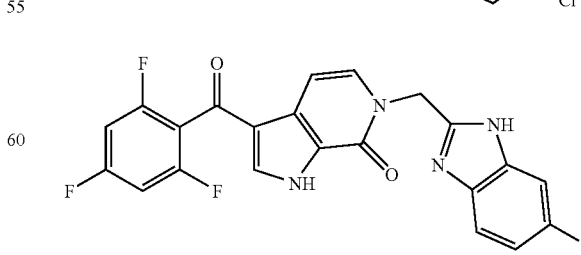 |

| 91 -continued | 92 -continued |
|---|---|
| Structure | Structure |
| 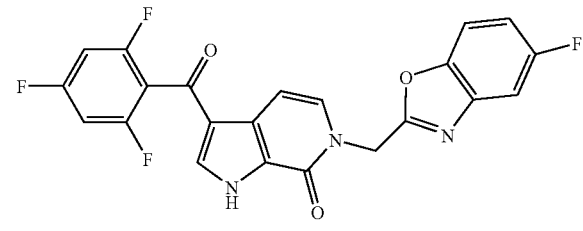 | 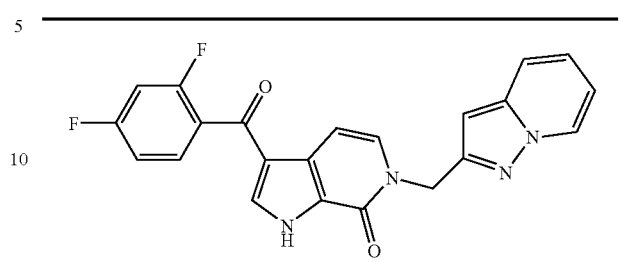 |
| 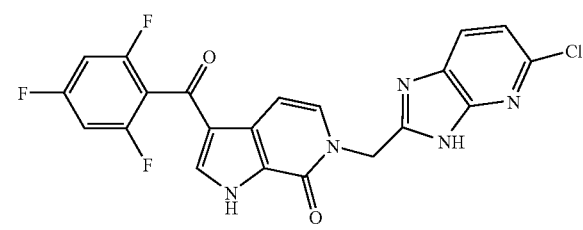 | 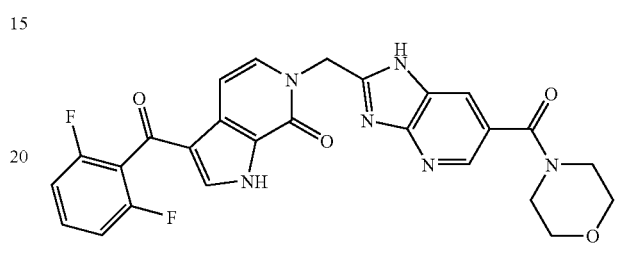 |
| 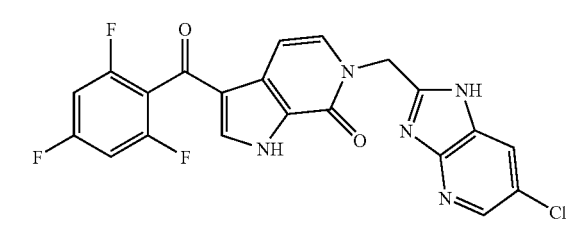 | 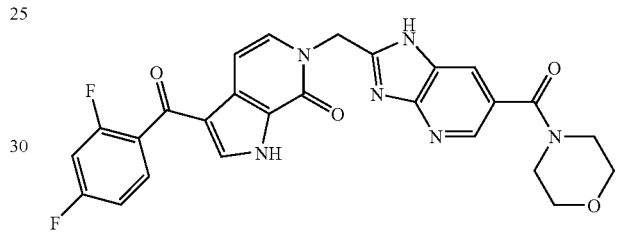 |
| 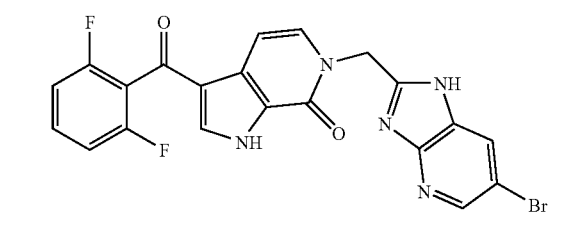 | 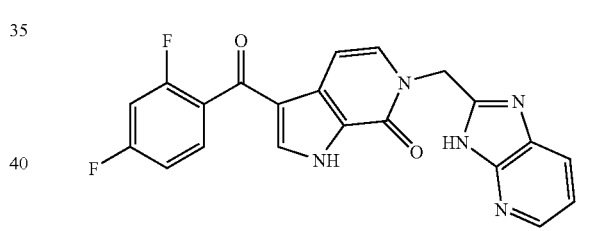 |
| 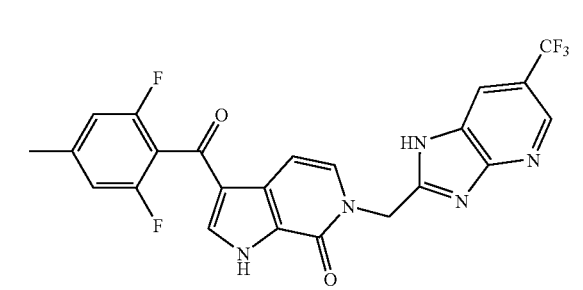 | 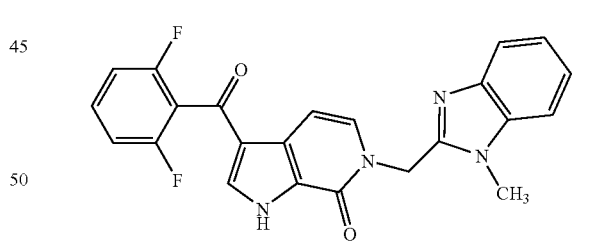 |
| 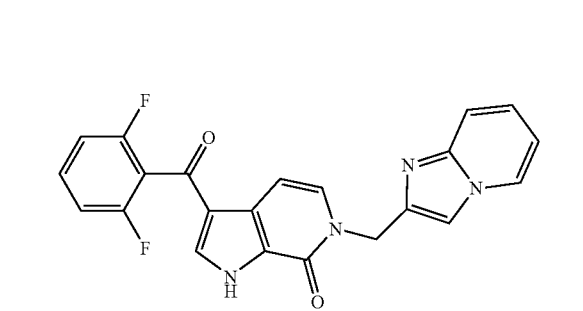 | 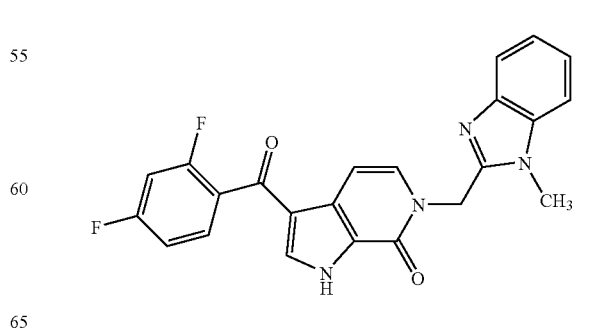 |

| 93 -continued | 94 -continued |
|---|---|
| Structure | Structure |
| 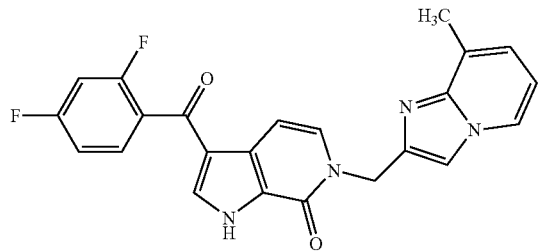 | 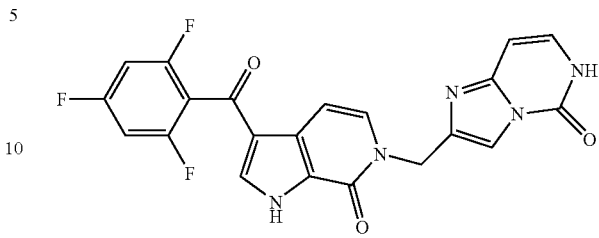 |
| 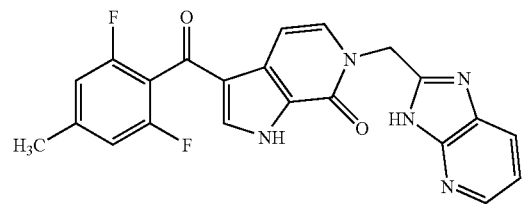 | 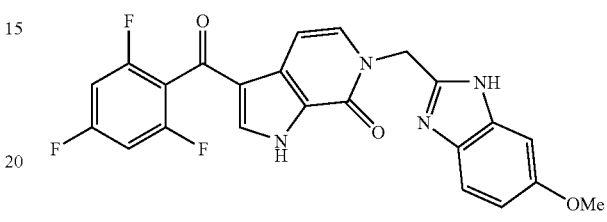 |
| 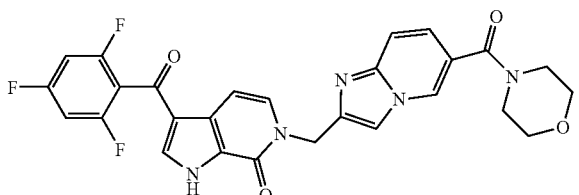 | 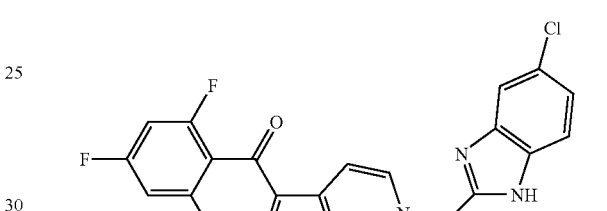 |
| 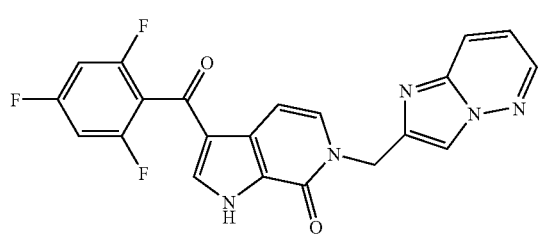 | 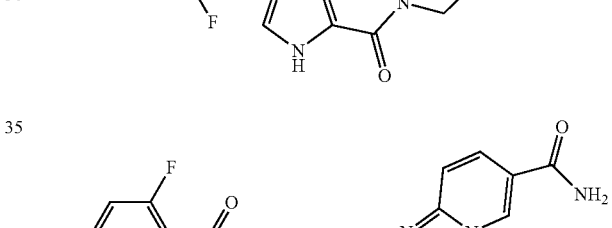 |
| 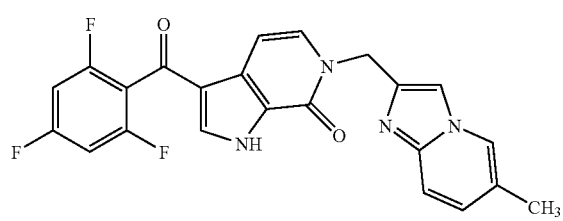 | 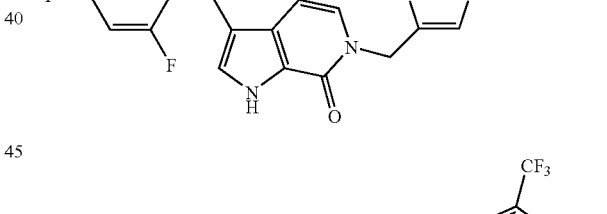 |
| 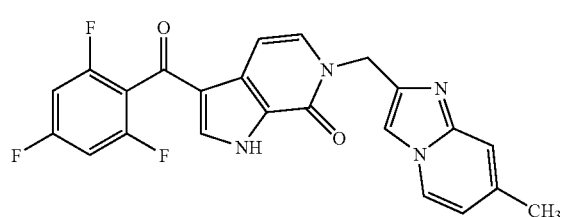 | 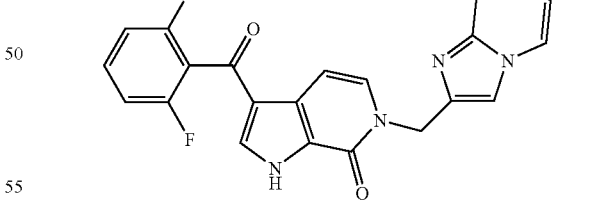 |
| 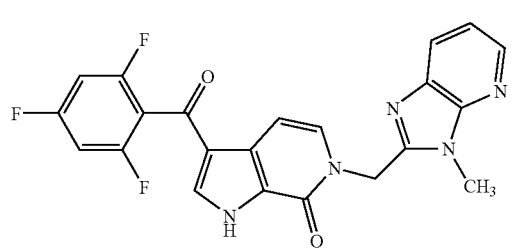 | 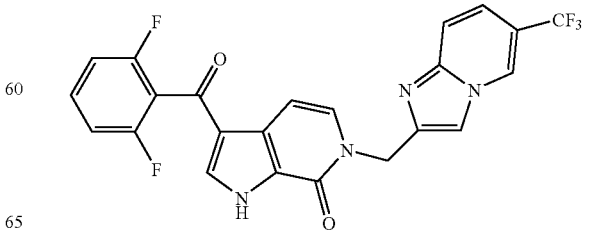 |

| 95 -continued | 96 -continued |
|---|---|
| Structure | Structure |
| 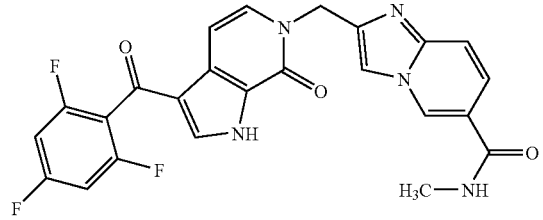 | 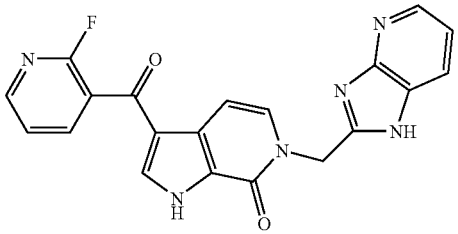 |
| 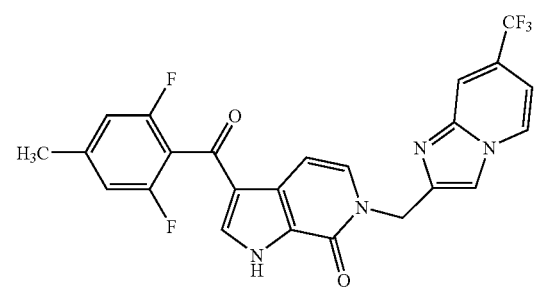 | 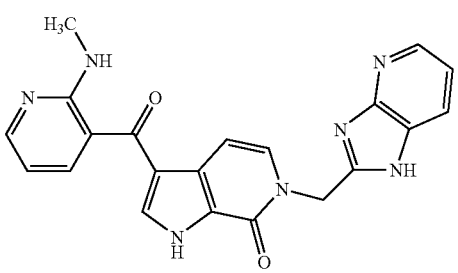 |
| 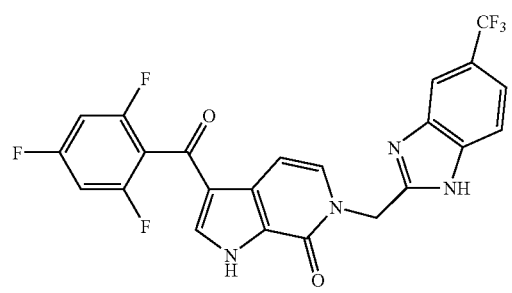 | 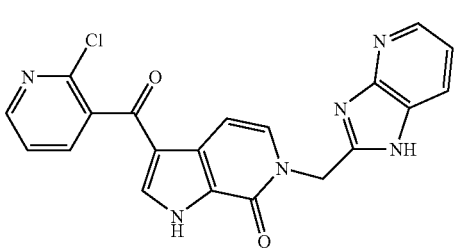 |
| 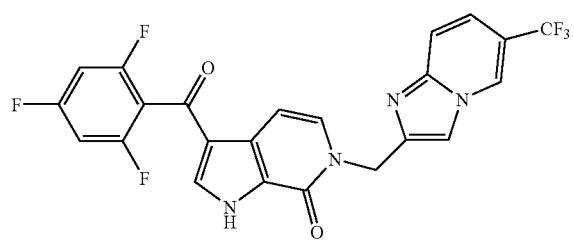 | 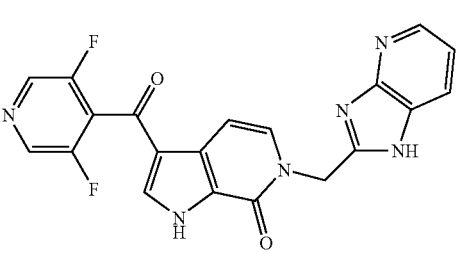 |
| 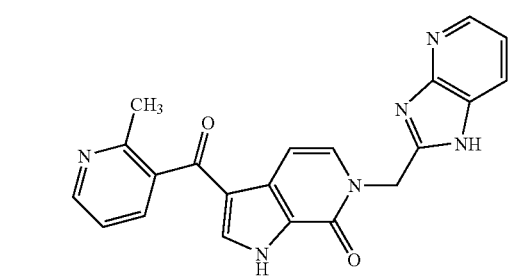 | 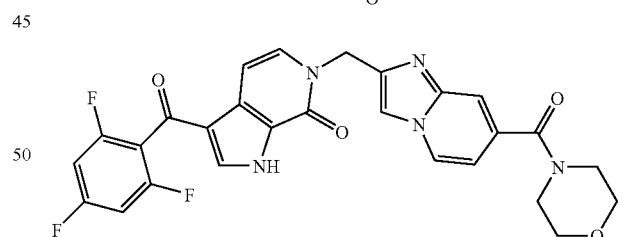 |
| 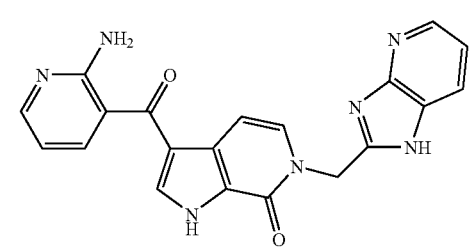 | 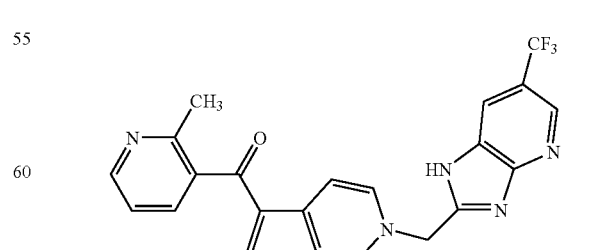 |

-continued

| Structure |
|---|
| 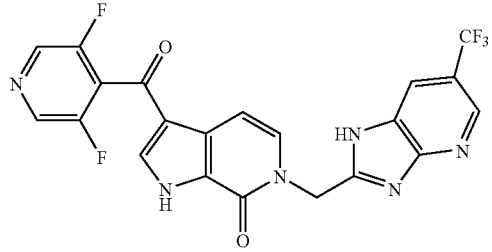 |
| 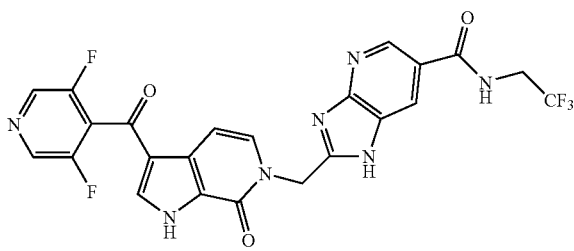 | or a Pharmaceutically acceptable slat thereof.

14. The compound according to claim 1, selected from the group consisting of:
- 6-{[6-(1H-pyrrol-2-yl)-1H-imidazo[4,5-b]pyridin-2-yl]methyl}-3-(2,4,6-trifluorobenzolyl)-1,6-dihydro-7H-pyrrolo[2,3-c]pyridin-7-one,
- 6-{[6-(3,5-dimethylisoxazol-4-yl)-1H-imidazo[4,5-b]pyridin-2-yl]methyl}-3-(2,4,6-trifluorobenzoyl)-1,6-dihydro-7H-pyrrolo[2,3-c]pyridin-7-one,
- 6-{[6-(1H-pyrrol-3-yl)-1H-imidazo[4,5-b]pyridin-2-yl]methyl}-3-(2,4,6-trifluorobenzoyl)-1,6-dihydro-7H-pyrrolo[2,3-c]pyridin-7-one,
- 6-[(6-methyl-1H-imidazo[4,5-b]pyridin-2-yl)methyl]-3-(2,4,6-trifluorobenzoyl)-1,6-dihydro-7H-pyrrolo[2,3-c]pyridin-7-one,
- 6-{[6-(1H-pyrrol-3-yl)-1H-imidazo[4,5-b]pyridin-2-yl]methyl}-3-(2,4,6-trifluorobenzoyl)-1,6-dihydro-7H-pyrrolo[2,3-c]pyridin-7-one,
- 6-{[6-(1-methyl-1H-pyrazol-3-yl)-1H-imidazo[4,5-b]pyridin-2-yl]methyl}-3-(2,4,6-trifluorobenzoyl)-1,6-dihydro-7H-pyrrolo[2,3-c]pyridin-7-one,
- 6-{[6-(3,5-dimethyl-1H-pyrazol-4-yl)-1H-imidazo[4,5-b]pyridin-2-yl]methyl}-3-(2,4,6-trifluorobenzoyl)-1,6-dihydro-7H-pyrrolo[2,3-c]pyridin-7-one
- 3-(2,6-Difluoro-4-methyl-benzoyl)-6-[6-(3,5-dimethyl-isoxazol-4-yl)-3-H-imidazo[4,5-b]pyridin-2-ylmethyl]-1,6-dihydro-pyrrolo[2,3-c]pyridin-7-one,
- 3-(2,6-Difluoro-benzoyl)-6-[6-(3,5-dimethyl-isoxazol-4-yl)-3-H-imidazo[4,5-b]pyridin-2-ylmethyl]-1,6-dihydro-pyrrolo[2,3-c]pyridin-7-one,
- 3-(2,6-Difluoro-4-methyl-benzoyl)-6-[6-(3,5-dimethyl-1H-pyrazol-4-yl)-3H-imidazo[4,5-b]pyridin-2-ylmethyl]-1,6-dihydro-pyrrolo[2,3-c]pyridin-7-one,
- 3-(2,6-Difluoro-benzoyl)-6-[6-(1H-pyrazol-4-yl)-3H-imidazo[4,5-b]pyridin-2-ylmethyl]-1,6-dihydro-pyrrolo[2,3-c]pyridin-7-one,
- 3-(2,6-Difluoro-4-methyl-benzoyl)-6-[6-(1-H-pyrazol-4-yl)-3-H-imidazo[4,5-b]pyridin-2-ylmethyl]-1,6-dihydro-pyrrolo[2,3-c]pyridin-7-one, and
- 3-(2,6-Difluoro-benzoyl)-6-[6-(1H-pyrazol-3-yl)-3H-imidazo[4,5-b]pyridin-2-ylmethyl]-1,6-dihydro-pyrrolo[2,3-c]pyridin-7-one, or a pharmaceutically acceptable salt thereof.

15. A compound according to claim 1 which is:

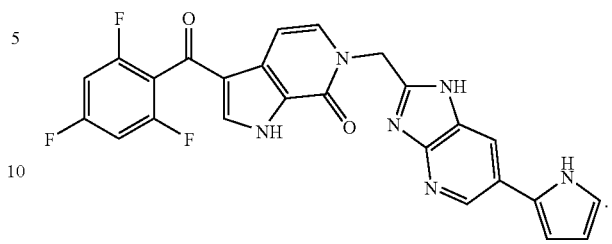

16. A compound according to claim 1 which is

TABLE I

| Example | Ar1 | Het |
|---|---|---|
| 83 | 2,4,6-trifluorophenyl | 3,5-dimethylisoxazol-4-yl |
| 84 | 2,4,6-trifluorophenyl | 1H-pyrrol-3-yl |
| 85 | 2,4,6-trifluorophenyl | 1-(tri-tert-butylsilyl)-1H-pyrrol-3-yl |
| 86 | 2,4,6-trifluorophenyl | 1H-pyrazol-3-yl |
| 87 | 2,4,6-trifluorophenyl | 1-methyl-1H-pyrazol-3-yl |
| 88 | 2,4,6-trifluorophenyl | 3,5-dimethyl-1H-pyrazol-4-yl |

TABLE I-continued
| Example | Ar1 | Het |
|---|---|---|
| 89 | | |
| 90 | | |
| 91 | | |
| 92 | | |
| 93 | | |
| 94 | | |
17. A pharmaceutical composition comprising an inert carrier and an effective amount of a compound according to claim 1.
18. A compound which is
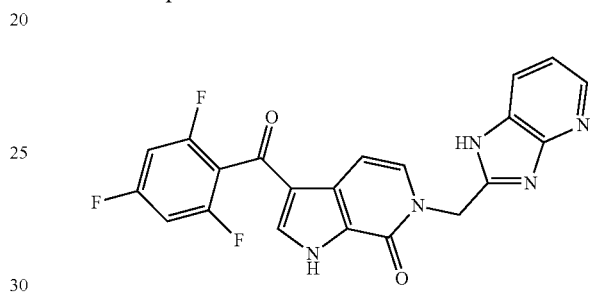
or a pharmaceutically acceptable salt thereof.
19. A pharmaceutical composition comprising an inert carrier and an effective amount of a compound according to claim 18.
* * * * *